United States Patent
Müller et al.

(10) Patent No.: US 12,208,145 B2
(45) Date of Patent: Jan. 28, 2025

(54) [161 TB]-BASED RADIOPEPTIDES

(71) Applicants: Universität Basel, Basel (CH); Paul Scherrer Institute, Villigen-PSI (CH)

(72) Inventors: Cristina Müller, Nussbaumen (CH); Roger Schibli, Baden (CH); Nicholas Philip Van Der Meulen, Schinznach-Dorf (CH); Francesca Borgna, Windisch (CH); Damian Wild, Basel (CH); Melpomeni Fani, Basel (CH)

(73) Assignees: Universität Basel, Basel (CH); Paul Scherrer Institute, Villigen-PSI (CH)

(*) Notice: Subject to any disclaimer, the term of this patent is extended or adjusted under 35 U.S.C. 154(b) by 0 days.

(21) Appl. No.: 18/172,094

(22) Filed: Feb. 21, 2023

(65) Prior Publication Data

US 2023/0293736 A1 Sep. 21, 2023

Related U.S. Application Data

(63) Continuation of application No. 17/955,923, filed on Sep. 29, 2022.

(60) Provisional application No. 63/250,621, filed on Sep. 30, 2021.

(51) Int. Cl.
| | |
|---|---|
| *A61K 51/08* | (2006.01) |
| *A61K 9/00* | (2006.01) |
| *A61K 9/08* | (2006.01) |
| *A61K 47/12* | (2006.01) |
| *A61K 47/22* | (2006.01) |
| *A61K 51/12* | (2006.01) |
| *A61P 35/00* | (2006.01) |

(52) U.S. Cl.
CPC .......... *A61K 51/083* (2013.01); *A61K 9/0019* (2013.01); *A61K 9/08* (2013.01); *A61K 47/12* (2013.01); *A61K 47/22* (2013.01); *A61K 51/088* (2013.01); *A61K 51/121* (2013.01); *A61P 35/00* (2018.01)

(58) Field of Classification Search
CPC ...... A61K 51/083; A61K 9/0019; A61K 9/08; A61K 47/12; A61K 47/22; A61K 51/121
See application file for complete search history.

(56) References Cited

U.S. PATENT DOCUMENTS 11,541,134 B1 * 1/2023 Kim ..................... A61K 51/121

OTHER PUBLICATIONS

Baum, R. et al., First-in-Humans Study of the SSTR Antagonist 177Lu-DOTA-LM3 for Peptide Receptor Radionuclide Therapy in Patients with Metastatic Neuroendocrine Neoplasms: Dosimetry, Safety, and Efficacy, The Journal of Nuclear Medicine, 62(11): 1571-1581, Mar. 5, 2021.
Borgna, F. et al., Simultaneous Visualization of 161Tb-and 177Lu-Labeled Somatostatin Analogues Using Dual-Isotope SPECT Imaging, Pharmaceutics, 13(4): 536, Apr. 12, 2021, 24 pages including Supplementary Material.
Borgna, F. et al., Combination of terbium-161 with somatostatin receptor antagonists—a potential paradigm shift for the treatment of neuroendocrine neoplasms, European Journal of Nuclear Medicine and Molecular Imaging, 49(4): 1113-1126, Oct. 8, 2021.
Zhang, J. et al., Successful Intra-arterial Peptide Receptor Radionuclide Therapy of DOTATOC-Negative High-Grade Liver Metastases of a Pancreatic Neuroendocrine Neoplasm Using 177Lu-DOTA-LM3: A Somatostatin Receptor Agonist, Clinical Nuclear Medicine, 45(3): e165-e168, Mar. 1, 2020.
Patent Cooperation Treaty No. PCT/EP2021/080220 International Search Report/Written Opinion, Jun. 30, 2022.
Schibli, R., et al. Simultaneous Auger e– and β--Particle Therapy of Metastasized NET Using 161-Tb DOTATOC, Center for Radiopharmaceutical Sciences, Virtual NETRF Research Symposium on Nov. 19-20, 2020, enlarged for legibility.

* cited by examiner

*Primary Examiner* — Robert S Cabral
(74) *Attorney, Agent, or Firm* — Julie K. Staple; Dinsmore & Shohl LLP

(57) ABSTRACT

A radiopeptide is provided which comprises (a) a radionuclide, wherein the radionuclide is terbium-161, (b) a chelator coordinating terbium-161, and (c) a peptide or peptide analogue, which is a somatostatin receptor (SSTR) antagonist. The radiopeptide is suitable for use in the treatment of tumor diseases.

20 Claims, 21 Drawing Sheets
Specification includes a Sequence Listing.

FIG. 2A
FIG. 2B
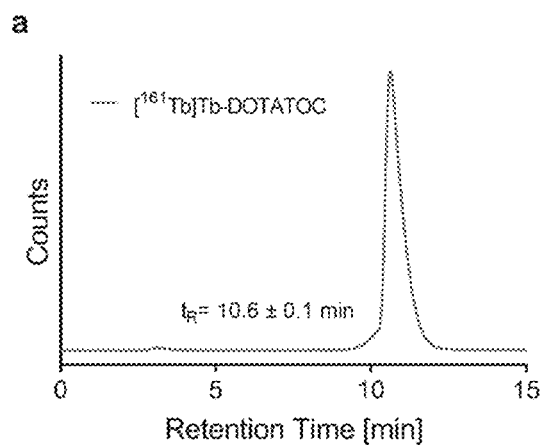
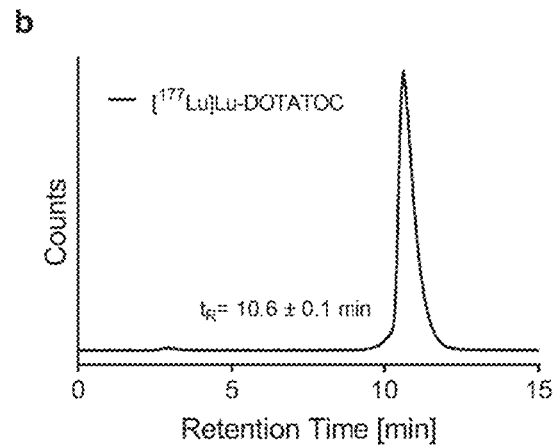
FIG. 2C
FIG. 2D
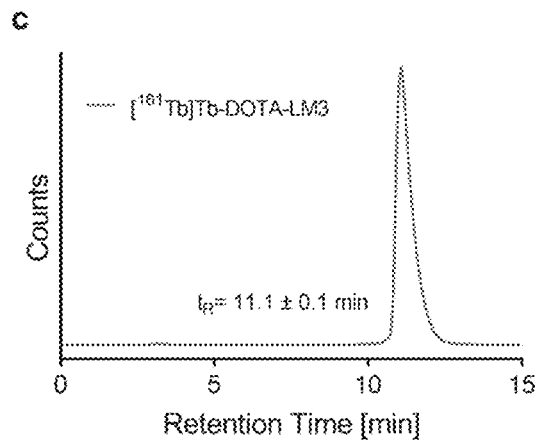
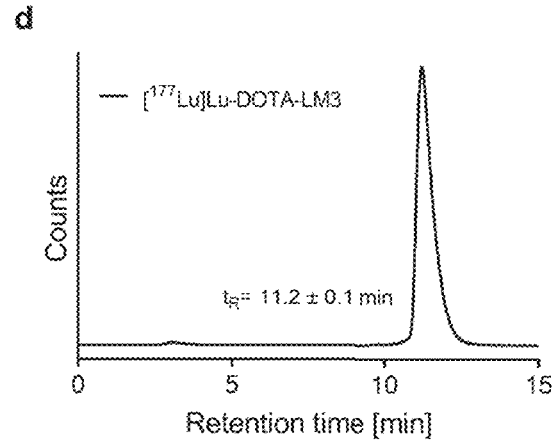

FIG. 4A
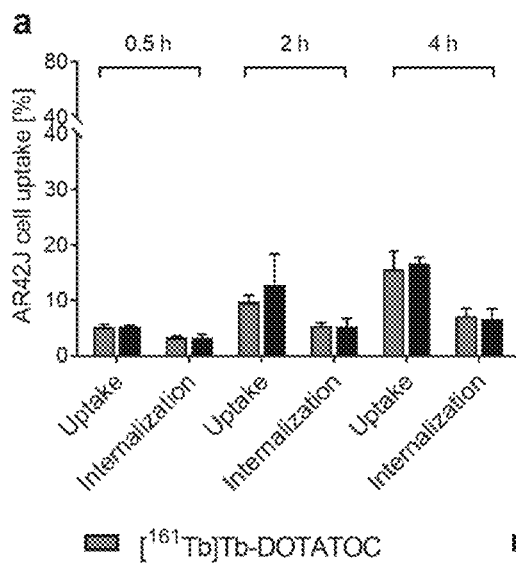
FIG. 4C
FIG. 4B
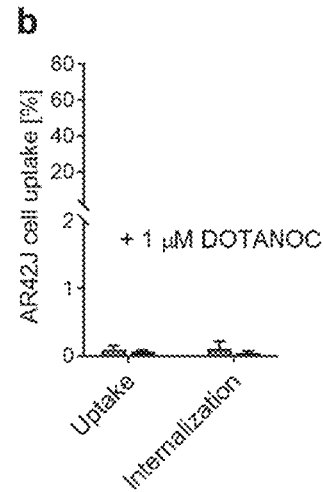
FIG. 4D
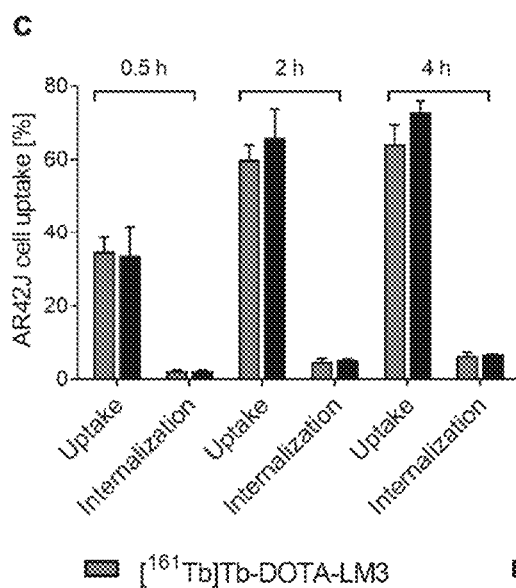
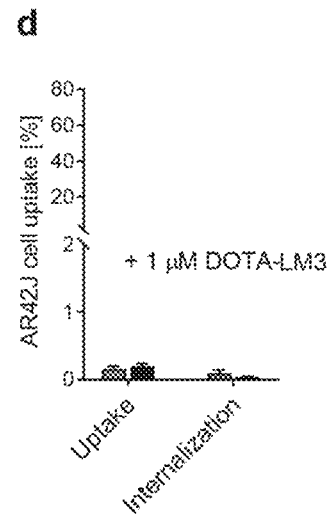

FIG. 13A
FIG. 13B
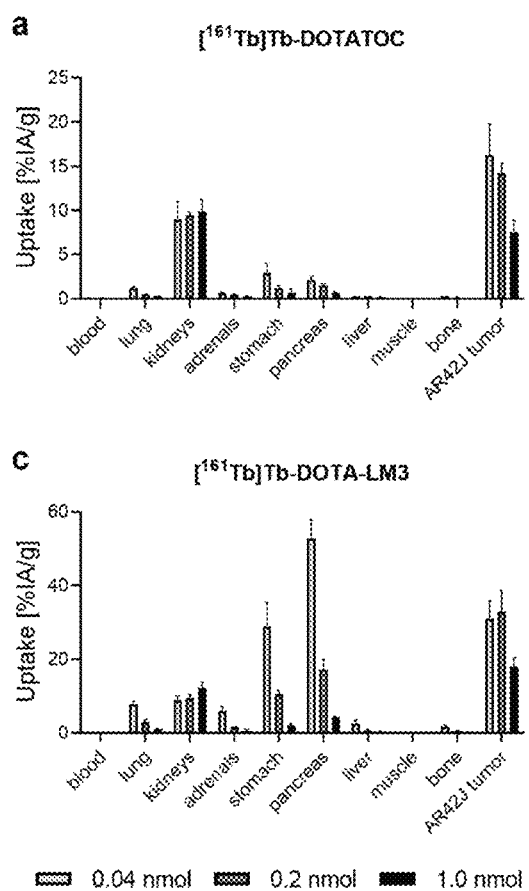
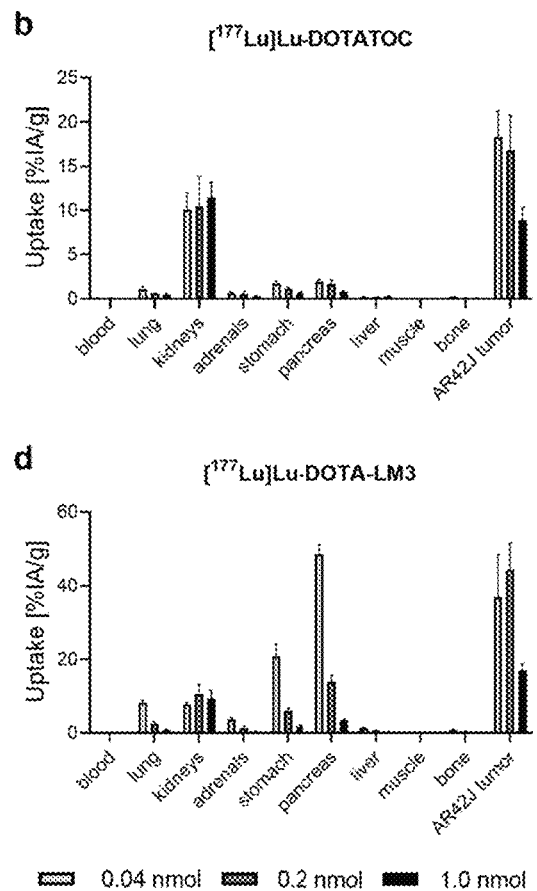
FIG. 13C
FIG. 13D

FIG. 14A
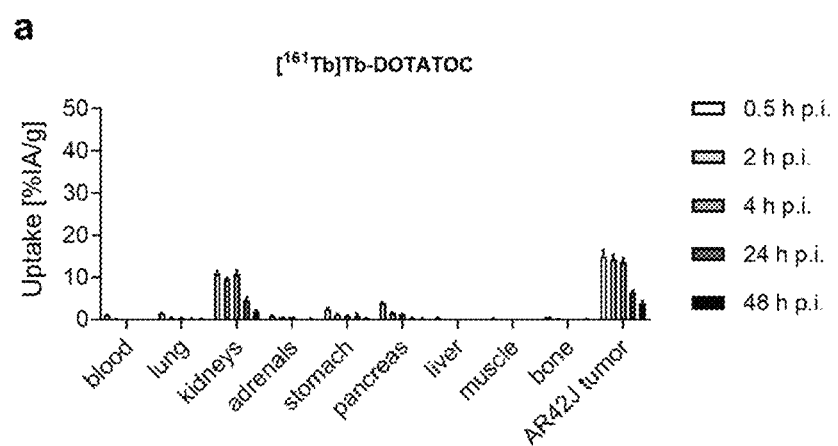
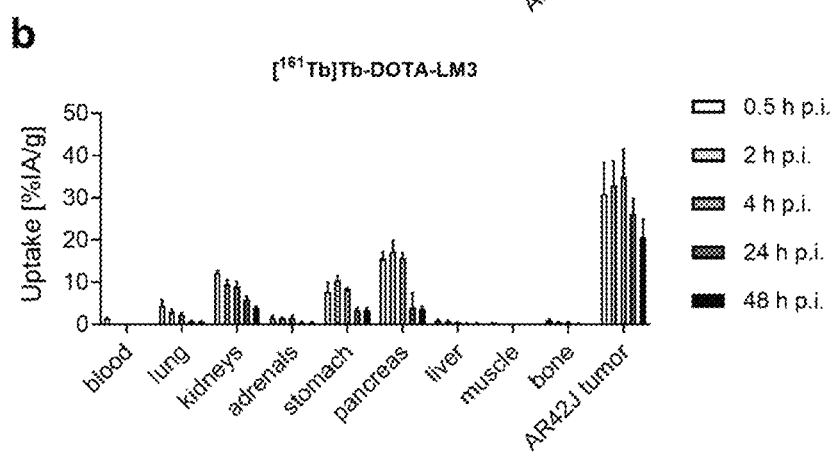
FIG. 14B

[161 TB]-BASED RADIOPEPTIDES

REFERENCE TO RELATED APPLICATIONS

This application is a continuation of U.S. patent application Ser. No. 17/955,923, filed Sep. 29, 2022, which claims priority to U.S. Provisional Patent Application Ser. No. 63/250,621, filed Sep. 30, 2021, the entire content of both of which is incorporated herein by reference.

SEQUENCE LISTING

The instant application contains a Sequence Listing which has been submitted electronically in XML, format and is hereby incorporated by reference in its entirety. Said Sequence Listing, created on Dec. 3, 2024, is named 12-3UBAS0001NA.xml and is 82,459 bytes in size.

FIELD OF THE INVENTION

According to aspects of the present disclosure, a radiopeptide is provided which comprises (a) a radionuclide, wherein the radionuclide is terbium-161, (b) a chelator coordinating terbium-161, and (c) a peptide or peptide analogue, which is a somatostatin receptor (SSTR) antagonist. The radiopeptide is suitable for use in the treatment of tumor diseases and aspects of methods of such treatment are disclosed herein.

BACKGROUND OF THE INVENTION

Neuroendocrine neoplasms (NENs) are a group of biologically and clinically heterogeneous malignancies, which originate in the diffuse neuroendocrine system mostly in the gastro-pancreatic or bronchopulmonary tract [1, 2]. Peptide receptor radionuclide therapy (PRRT) using radiolabeled somatostatin (SST) analogues has been employed for almost three decades to treat low- to intermediate-grade NENs that express the somatostatin receptor (SSTR) [1, 3, 4]. The initially used [$^{111}$In]In-octreotide was effective for symptom palliation, but induced rarely objective radiographic responses in NENs. The short tissue penetration range of Auger electrons (<1 μm) was not sufficient for an effective cancer therapy and a dose escalation was not feasible due to the emission of a substantial amount of γ-radiation by indium-111 (Eγ=171 keV, I=91%; 245 keV, I=94%) [5, 6]. The application of yttrium-90 (E$\beta_{average}$=934 keV, $T_{1/2}$=2.67 d) was more successful for PRRT [7]. It was recognized over time, however, that the high energy β$^-$-particles (tissue range up to 10 mm) are unfavorable, as they caused kidney toxicity [8, 9]. Lutetium-177, a medium energy β$^-$-particle emitter (E$\beta_{average}$=134 keV, $T_{1/2}$=6.65 d; tissue range <2 mm [10]) emerged as the preferred radionuclide for PRRT [11, 12]. $^{177}$Lu-labeled somatostatin analogues revealed to be effective to treat NENs with commonly favorable safety profiles [8]. The γ-ray emission of lutetium-177 has been used for γ-scintigraphy and SPECT imaging. Currently, lutetium-177 is the most often employed radiometal for PRRT using [$^{177}$Lu]Lu-DOTATATE (Lutathera™) [13, 14]) or [$^{177}$Lu]Lu-DOTATOC [15].

More recently, α-particle emitters (LET=50-230 keV/μm) have been proposed for targeted radionuclide therapy [16]. In the case of NENs, [$^{213}$Bi]Bi-DOTATOC/DOTATATE and [$^{225}$]Ac-DOTATOC/DOTATATE showed promising results in preclinical studies [17-20]. In the clinics, [213Bi]Bi-DOTATOC was used for the treatment of patients (n=7) with progressive advanced neuroendocrine liver metastases refractory to the treatment with [$^{90}$Y]Y-/[$^{177}$Lu]Lu-DOTA-TOC [21]. [$^{225}$Ac]Ac-DOTATATE was investigated in a prospective study in 32 patients with stable or progressive disease after [$^{177}$Lu]Lu-DOTATATE therapy resulting in partial remission or stable disease [22]. There are, however, a number of uncertainties regarding the application of actinium-225, among those the inability to use it for imaging and, finally, the difficult production scenarios which makes its availability generally challenging [23-25]. The complicated decay scheme of actinium-225 and the resulting increased risk for undesired side effects limits its application to fast internalizing radioligands (e.g. [$^{225}$Ac]Ac-based PSMA radioligands) and prevents its use with radiopharmaceuticals which localize on the cell surface, such as somatostatin antagonists.

The object of this study was to identify a radionuclide therapy which decays—as described for $^{177}$Lu—by the emission of medium energy β$^-$-particles and emits γ-radiation suitable for imaging purposes. It was a further object to enable a radionuclide therapy in combination with a suitable targeting agent which act in a well-coordinated manner.

The solution to that object is defined by the subject-matter of claim 1. The present invention is based on the finding that terbium-161 in combination with an antagonistic somatostatin analogue leads to an advanced PRRT. Terbium-161 exhibits decay characteristics for targeted radionuclide therapy similar to lutetium-177. It decays by the emission of medium energy β$^-$-particles (E$\beta_{average}$=154 keV; $T_{1/2}$=6.9 d [27]) and emits γ-radiation potentially suitable for imaging purposes (Eγ=48.9 keV, I=17% and 74.6 keV, I=10%) [28]. Advantageously, terbium-161 co-emits a substantial number of Auger and conversion electrons (due to their high linear energy transfer (LET: 4-26 keV/μm)) generating value in tumor therapies, particularly when envisaging the treatment of single cancer cells [26, 29]. Terbium-161 was found to be advantageously combined with an antagonistic somatostatin (SST) analogue as the targeting agent, even more so when the targeting agent was found to be dominantly localized on the cell surface rather than internalized by the cell. Such a combination was shown to benefit from the effect of the co-emitted conversion and Auger electrons (high LET electrons).

SUMMARY OF THE INVENTION

Radiopeptides are provided according to aspects of the present disclosure which include: (a) a radionuclide, wherein the radionuclide is terbium-161, (b) a chelator of terbium-161, and (c) a peptide or peptide analogue, which is a somatostatin receptor (SSTR) antagonist.

According to particular aspects of the disclosure, the somatostatin receptor (SSTR) antagonist is covalently coupled to (b).

According to particular aspects of the disclosure, the chelator is a cyclic chelator, in particular a macrocyclic chelator.

According to particular aspects of the disclosure, the chelator is a tetradentate chelator.

According to particular aspects of the disclosure, the chelator contains four nitrogen atoms.

According to particular aspects of the disclosure, the chelator is a 12-membered tetraaza ring system.

According to particular aspects of the disclosure, the chelator includes at least one substituent containing at least one carboxy function.

According to particular aspects of the disclosure, the chelator is DOTA or a DOTA derivative.

According to particular aspects of the disclosure, the DOTA derivative is selected from the group consisting of:

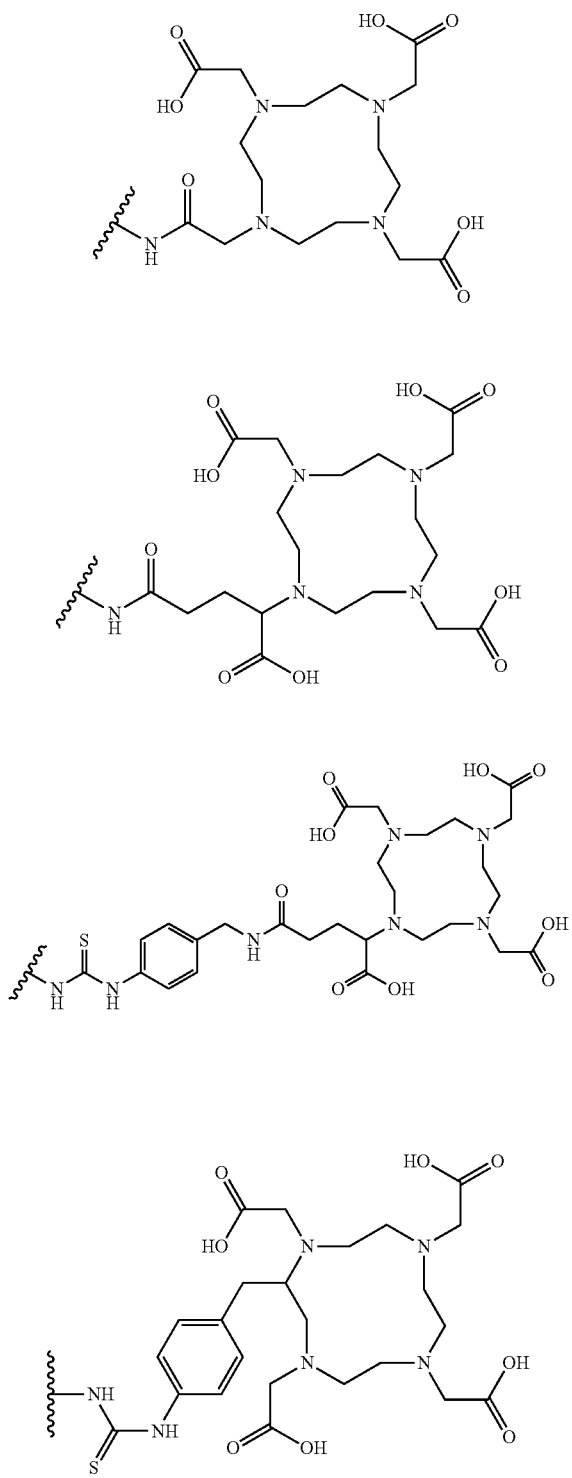

According to particular aspects of the disclosure, the chelator is DOTA (dodecane tetraacetic acid).

According to particular aspects of the disclosure, the somatostatin receptor antagonist is covalently coupled to the chelator via an amide linkage.

According to particular aspects of the disclosure, the somatostatin receptor antagonist binds to SSTR-2 (sst2) or is an SSTR-2 (sst2) selective antagonist.

According to particular aspects of the disclosure, less than 20% of the administered somatostatin receptor antagonist is internalized by cells.

According to particular aspects of the disclosure, the somatostatin receptor antagonist is a cyclic peptide.

According to particular aspects of the disclosure, the somatostatin receptor antagonist contains two cysteine residues, which preferably form a disulfide bridge.

According to particular aspects of the disclosure, the somatostatin receptor antagonist contains the two cysteine residues at peptide positions 2 and 7.

According to particular aspects of the disclosure, the somatostatin receptor antagonist comprises 8 to 14 amino acids, preferably 8 to 10, more preferably 8 amino acids.

According to particular aspects of the disclosure, the somatostatin receptor antagonist includes formula I: X1-cyclo[D-Cys-X3-X4-Lys-Thr-Cys]-D-Tyr-NH$_2$, (SEQ ID NO:1) wherein X1, X3, and X4 are selected from a naturally or a non-naturally occurring D- or L-amino acid.

According to particular aspects of the disclosure, (i) X1 is selected from the group consisting of naturally occurring Phe or a substituted Phe having one or more substitutions at the phenyl ring system and Cpa, (ii) X3 is selected from the group consisting of Aph(Hor), Leu, L-Agl(NMe.benzoyl), D-Agl(NMe.benzoyl), Aph(Cbm),Tyr, Aph(CONH—OCH$_3$), Tyr, Aph(CONH—OH), and/or (iii) X4 is selected from the group consisting of D-Trp and D-Aph(Cbm) (D-4-amino-Phe(carbamoyl)), wherein X1 is preferably selected from the group consisting of pNOs-Phe, pCl-Phe and Cpa, X3 is preferably selected from the group consisting of Tyr, Aph(Cbm), and Aph(Hor), and/or X4 is preferably selected from the group consisting of D-Trp and D-Aph(Cbm).

According to particular aspects of the disclosure, the somatostatin receptor antagonist is selected from the group consisting of LM3 ([p-Cl-Phe-cyclo[D-Cys-Tyr-D-Aph(Cbm)-Lys-Thr-Cys]D-Tyr-NH$_2$]) (SEQ ID NO:2), JR11 (Cpa-cyclo[D-Cys-Aph(Hor)-D-Aph(Cbm)-Lys-Thr-Cys]-D-Tyr-NH$_2$) (SEQ ID NO:3), and BASS (pNO$_2$-Phe-cyclo[D-Cys-Tyr-D-Trp-Lys-Thr-Cys]D-Tyr-NH$_2$) (SEQ ID NO:4).

According to particular aspects of the disclosure, terbium-161 is produced by neutron irradiation of gadolinium-160.

According to particular aspects of the disclosure, terbium-161 is a non-carrier-added terbium-161 (n.c.a. terbium-161).

According to particular aspects of the disclosure, the antagonist is preferentially taken up by tumors relative to other tissue.

According to particular aspects of the disclosure, the ratio of radiopeptide uptake in tumor cells to radiopeptide uptake in blood is at least 50.0, the ratio of radiopeptide uptake in tumor cells to radiopeptide uptake in liver cells is at least 10.0 and/or the ratio of radiopeptide uptake in tumor cells to radiopeptide uptake in kidney cells is at least 2.0, preferably measured 2 hours after administration.

According to particular aspects of the disclosure, the radiopeptide has the structure of the following formula:

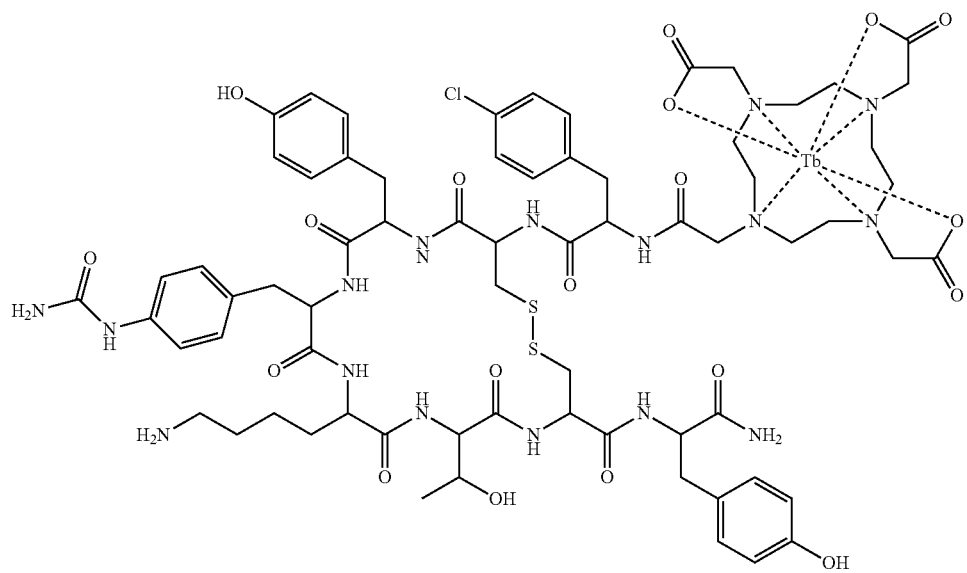

Pharmaceutical compositions are provided according to aspects of the present disclosure which include: (a) a radionuclide, wherein the radionuclide is terbium-161, (b) a chelator of terbium-161, and (c) a peptide or peptide analogue, which is a somatostatin receptor (SSTR) antagonist; and at least one pharmaceutically acceptable excipient. According to preferred aspects, the at least one pharmaceutically acceptable excipient is water.

According to particular aspects of the disclosure, the pharmaceutical composition includes 0.001 to 1 mg/ml radiopeptide, 0.01 to 1 mg/ml radiopeptide, or 0.05 to 0.5 mg/ml radiopeptide.

According to particular aspects of the disclosure, the pharmaceutical composition includes at least one of the group consisting of: gentisic acid, ethanol, acetate, NaCl, and ascorbate/ascorbic acid.

According to particular aspects of the disclosure, the pharmaceutical composition includes ascorbate.

According to particular aspects of the disclosure, the pharmaceutical composition includes 0.5 mM to 0.5 M ascorbate, in particular 1 mM to 100 mM ascorbate, or 10 mM to 100 mM ascorbate.

According to particular aspects of the disclosure, the pharmaceutical composition has a pH value from pH 3.5 to pH 6, or from pH 4 to pH 6.

Methods of treating a disease or a tumor disease are provided according to aspects of the present disclosure which include administering a radiopeptide including: (a) a radionuclide, wherein the radionuclide is terbium-161, (b) a chelator of terbium-161, and (c) a peptide or peptide analogue, which is a somatostatin receptor (SSTR) antagonist, to a subject in need of a disease treatment or tumor disease treatment. According to aspects of the present disclosure, the radiopeptide is administered systemically, preferably intravenously.

Methods of treating a neuroendocrine neoplasm and/or metastases thereof, in particular liver metastases, are provided according to aspects of the present disclosure which include administering a radiopeptide including: (a) a radionuclide, wherein the radionuclide is terbium-161, (b) a chelator of terbium-161, and (c) a peptide or peptide analogue, which is a somatostatin receptor (SSTR) antagonist, to a subject in need of a disease treatment or tumor disease treatment. According to aspects of the present disclosure, the neuroendocrine neoplasm is of Grade 1, Grade 2 or Grade 3. According to aspects of the present disclosure, the neuroendocrine neoplasm is stable or refractory to a therapy by Lutetium ($^{177}$Lu)-Oxodotreotid (Lutathera®) or other radiolabelled somatostatin analogues. According to aspects of the present disclosure, the radiopeptide is administered systemically, preferably intravenously.

Methods of treating a neuroendocrine neoplasm in the gastro-pancreatic, bronchopulmonary tract, thyroid, thymus, or pituitary gland and/or metastases thereof, are provided according to aspects of the present disclosure which include administering a radiopeptide including: (a) a radionuclide, wherein the radionuclide is terbium-161, (b) a chelator of terbium-161, and (c) a peptide or peptide analogue, which is a somatostatin receptor (SSTR) antagonist, to a subject in need of a disease treatment or tumor disease treatment. According to aspects of the present disclosure, the neuroendocrine neoplasm is of Grade 1, Grade 2 or Grade 3. According to aspects of the present disclosure, the neuroendocrine neoplasm is stable or refractory to a therapy by Lutetium ($^{177}$Lu)-Oxodotreotid (Lutathera®) or other radiolabelled somatostatin analogues. According to aspects of the present disclosure, the radiopeptide is administered systemically, preferably intravenously.

Methods of treating a neuroendocrine neoplasm selected from the group consisting of: gastroenteropancreatic neuroendocrine neoplasm, neuroendocrine tumor of the lung, neuroendocrine carcinoma of the lung, in particular small cell lung cancer, thymic neuroendocrine tumor, paraganglioma, pheochromocytoma, e.g. malignant pheochromocytoma, meningioma, medullary thyroid cancer, thyroid cancer, breast cancer, renal cell carcinoma, prostate cancer, and non-Hodgkin lymphoma, are provided according to aspects of the present disclosure which include administering a radiopeptide including: (a) a radionuclide, wherein the radionuclide is terbium-161, (b) a chelator of terbium-161, and (c) a peptide or peptide analogue, which is a somatostatin receptor (SSTR) antagonist, to a subject in need of a disease treatment or tumor disease treatment. According to aspects of the present disclosure, the neuroendocrine neoplasm is of Grade 1, Grade 2 or Grade 3. According to aspects of the present disclosure, the neuroendocrine neoplasm is stable or refractory to a therapy by Lutetium ($^{177}$Lu)-Oxodotreotid (Lutathera®) or other radiolabelled somatostatin analogues. According to aspects of the present disclosure, the radiopeptide is administered systemically, preferably intravenously.

Methods of treating a neuroendocrine neoplasm wherein the neuroendocrine neoplasm is a pancreatic tumor and/or metastases thereof, are provided according to aspects of the present disclosure which include administering a radiopeptide including: (a) a radionuclide, wherein the radionuclide is terbium-161, (b) a chelator of terbium-161, and (c) a peptide or peptide analogue, which is a somatostatin receptor (SSTR) antagonist, to a subject in need of a disease treatment or tumor disease treatment. According to aspects of the present disclosure, the neuroendocrine neoplasm is of Grade 1, Grade 2 or Grade 3. According to aspects of the present disclosure, the neuroendocrine neoplasm is stable or refractory to a therapy by Lutetium ($^{177}$Lu)-Oxodotreotid (Lutathera®) or other radiolabelled somatostatin analogues. According to aspects of the present disclosure, the radiopeptide is administered systemically, preferably intravenously.

BRIEF DESCRIPTION OF THE DRAWINGS

FIG. 1A shows DOTATOC (somatostatin receptor (SSTR) agonist) [15, 41], and FIG. 1B shows DOTA-LM3, (SSTR antagonist) [42];

FIGS. 2A-2D show graphs of representative HPLC chromatograms of the $^{161}$Tb- and $^{177}$Lu-labeled peptides; FIG. 2A shows [$^{161}$Tb]Tb-DOTATOC, FIG. 2B shows [$^{177}$Lu]Lu-DOTATOC, FIG. 2C shows [$^{161}$Tb]Tb-DOTA-LM3$^)$, and FIG. 2D shows $^{177}$Lu]Lu-DOTA-LM3. Traces of unreacted terbium-161 or lutetium-177 appeared with a retention time of ~2.5 min [44];

FIG. 3A shows percentage of intact [$^{161}$Tb]Tb-DOTA-TOC and [$^{177}$]Lu-Lu-DOTATOC in the absence and presence of L-ascorbic acid, and FIG. 3B shows percentage of intact [$^{161}$Tb]Tb-DOTA-LM3 and [$^{177}$]Lu-Lu-DOTA-LM3 in the absence and presence of L-ascorbic acid;

FIGS. 4A-4D show results of the in vitro tumor cell uptake and internalization of the radiopeptides in AR42J tumor cells after incubation for 0.5 h, 2 h and 4 h, respectively; FIG. 4A shows [$^{161}$Tb]Tb-DOTATOC and [$^{177}$Lu]Lu-DOTATOC, FIG. 4B shows [$^{161}$Tb]Tb-DOTATOC and [$^{177}$Lu]Lu-DOTATOC with excess peptide to block SSTR, FIG. 4C shows [$^{161}$Tb]Tb-DOTA-LM3 and [$^{177}$Lu]Lu-DOTA-LM3, and FIG. 4D shows [$^{161}$Tb]Tb-DOTA-LM3 and [$^{177}$Lu]Lu-DOTA-LM3 with excess peptide to block SSTR;

FIG. 5A shows [$^{177}$Lu]Lu-DOTATOC, and FIG. 5B shows [$^{177}$Lu]Lu-DOTA-LM3;

FIG. 6A shows cell localization of radiolabeled DOTATOC, and FIG. 6B shows cell localization of radiolabeled DOTA-LM3;

FIG. 7A shows the results of cells treated with [$^{161}$Tb]Tb-/[$^{177}$Lu]Lu-DOTATOC, and FIG. 7B shows the results of cells treated with [$^{161}$Tb]Tb-/[$^{177}$Lu]Lu-DOTA-LM3;

FIG. 8A shows the results of cells treated with [$^{161}$Tb]Tb-DOTATOC or [$^{177}$Lu]Lu-DOTATOC, and FIG. 8B shows the results of cells treated with [$^{161}$Tb]Tb-DOTA-LM3 or [$^{177}$Lu]Lu-DOTA-LM3;

FIG. 9A shows γ-H2AX-positive AR42J tumor cells after sham-treatment, FIG. 9B shows γ-H2AX-positive AR42J tumor cells after treatment with [$^{161}$Tb]Tb-DOTATOC or [$^{177}$Lu]Lu-DOTATOC, and FIG. 9C shows γ-H2AX-positive AR42J tumor cells after treatment [$^{161}$Tb]Tb-DOTA-LM3 or [$^{177}$Lu]Lu-DOTA-LM3 (2.5 and 10 MBq). The number of positive cells is expressed as percentage of the positive cases in sham-treated AR42J (set as 1.0);

FIGS. 12A and 12B show tissue distribution at 2 h after injection of the radiopeptides, and FIGS. 12C and 12D show tissue distribution at 24 h p.i. after injection of the radiopeptides. The results are presented as percentage of injected activity per tissue mass (% IA/g) (a/c) Data obtained with [$^{161}$Tb]Tb-DOTATOC and [$^{177}$Lu]Lu-DOTATOC (p>0.05); (b/d) Data obtained with [$^{161}$Tb]Tb-DOTA-LM3 and [$^{177}$Lu]Lu-DOTA-LM3 (p>0.05);

FIGS. 13A-13D show biodistribution data obtained in AR42J tumor-bearing mice 2 h after injection of the radiopeptides at different molar amounts; FIG. 13A shows tissue distribution of [$^{161}$Tb]Tb-DOTATOC, FIG. 13B shows tissue distribution of [$^{177}$Lu]Lu-DOTATOC, FIG. 13C shows tissue distribution of [$^{161}$Tb]Tb-DOTA-LM3, and FIG. 13D shows tissue distribution of [$^{177}$Lu]Lu-DOTA-LM3. The results are presented as percentage of injected activity per tissue mass (% IA/g);

FIGS. 14A and 14B show biodistribution data obtained in AR42J tumor-bearing mice after injection of the radiopeptides (0.2 nmol per mouse); FIG. 14A shows tissue distribution profile of the [$^{161}$Tb]Tb-DOTATOC, and FIG. 14B shows tissue distribution profile of [$^{161}$T]Tb-DOTA-LM3. The results are presented as percentage of injected activity per tissue mass (% IA/g);

FIG. 15A shows tumor growth curves relative to the tumor volume at Day 0 (set to 1) for mice that received sham treatment (Group A), [$^{161}$Tb]Tb-DOTATOC (10 MBq, 0.2 nmol, at Day 0 and Day 7) (Group B) and [$^{177}$Lu]Lu-DOTATOC (10 MBq, 0.2 nmol, at Day 0 and Day 7) (Group C), FIG. 15B shows tumor growth curves for mice that received sham treatment (Group A), [$^{161}$Tb]Tb-DOTA-LM3 (10 MBq, 0.2 nmol, at Day 0 and Day 7) (Group D) and [$^{177}$Lu]Lu-DOTA-LM3 (10 MBq, 0.2 nmol, at Day 0 and Day 7) (Group E). Data are shown until the first mouse of the respective group reached an endpoint, FIG. 15C shows Kaplan-Meier plots of Groups AB/C, and FIG. 15D shows Kaplan-Meier plots of Groups A/D/E;

FIG. 16A shows tumor growth delay of Group A-E, and FIG. 16B shows tumor doubling time of Groups A-E;

FIG. 17A shows RBWs of mice that received no treatment (Group A), [$^{161}$Tb]Tb-DOTATOC (Group B) and [$^{177}$Lu]Lu-DOTATOC (Group C), and FIG. 17B shows RBWs of mice that received no treatment (Group A), [$^{161}$Tb]Tb-DOTA-LM3 (Group D) and [$^{177}$Lu]Lu-DOTA-LM3 (Group E). Data are shown until the first mouse of the respective group reached an endpoint;

(FIG. 18B), 20 hours p.i. (FIG. 18C), and 113 hours p.i. (FIG. 18D) of $^{161}$Tb-DOTATOC in a 70-year-old male patient with a metastatic functional neuroendocrine neoplasm of the pancreatic tail. Early blood-pool activity was noticed in the heart (H) and blood vessels (BV). Physiological uptake was seen in the soft tissues, liver (Li), kidneys (Ki), and the bladder (Bl). Pathological uptake was demonstrated in the bilobar liver (thick gray arrows) and multifocal osseous metastases (black arrows); (FIG. 19A) Coronal section, (FIG. 19B) sagittal section, and (FIG. 19C) transverse section. Uptake of 161-DOTATOC was seen in bilobar hepatic metastases (white arrows), as well as multiple osteoblastic skeletal metastases in the vertebral column (black-filled arrows and the pelvis (thick white arrows).

DETAILED DESCRIPTION OF THE INVENTION

Figure 1A:
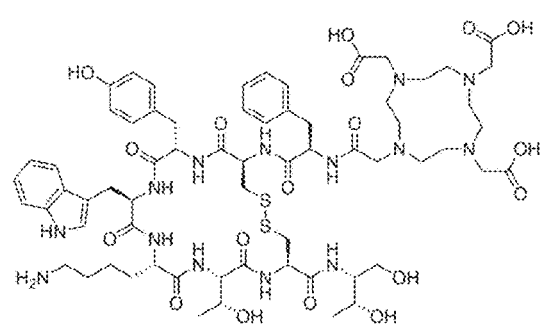
FIGS. 1A and 1B show chemical structures of the somatostatin (SST) analogues.

By a first aspect, the present invention solves the object by the provision of a radiopeptide comprising (a) a radioisotope/radionuclide, wherein the radioisotope/radionuclide is terbium-161, (b) a chelator of terbium-161, and (c) a peptide or peptide analogue, which is a somatostatin receptor (sstr) antagonist. The term "radiopeptide" is thus understood to mean that the claimed entity contains a radioisotope and peptide component. The terms "radionuclide" and "radioisotope" are used synonymously herein.

The present invention is based on the identification of terbium-161 as a trivalent radioactive metal isotope (i.e. a radioisotope) which is—in combination with other components of the inventive radiopeptide—an ideal radioactive candidate for β($^-$)-particle (tumor) therapy. Its decay properties of ($T_{1/2}$=6.89 d) are similar to $^{177}$Lu. Thus, its decay properties render terbium-161 suitable for PRRT. In addition, the co-emission of Auger electrons allows for a combined β$^-$/Auger electron therapy (~12 e$^-$/decay: Auger/conversion electrons). Experimental evidence of the present invention confirmed that a $^{161}$Tb-labeled somatostatin analogue as an sstr antagonist was more effective than its $^{177}$Lu-labeled counterparts, even though $^{161}$Tb and $^{177}$Lu are both trivalent radiolanthanides of considerable chemical similarity.

The production of $^{161}$Tb is advantageously carried out by using the $^{160}$Gd(n,γ)$^{161}$Gd→$^{161}$Tb nuclear reaction. Highly-enriched $^{160}$Gd targets may e.g. be irradiated for 2-3 weeks at the spallation-induced neutron source at the Paul Scherrer Institute (Switzerland) or for 1 week at the high neutron flux nuclear reactor, such as the reactor at the Institut Laue-Langevin, France or at Necsa (Pelindaba, South Africa). The product is separated from the Gd target material using ion exchange (resin) chromatographic methods to ensure provision of the final product in a small volume of dilute hydrochloric acid (e.g. less than 1 ml). The resulting quantities may be >10 GBq. The final product typically has a purity >98 or >99% (as $^{161}$TbCl$_2$). The radiopeptide's radionuclide terbium-161 may be specifically provided as non-carrier-added terbium-161 (n.c.a. terbium-161) defining that no non-radioactive terbium is present in the final product.

Terbium-161 is typically provided in stable coordination with a chelator according to the invention. The chelator is a molecule that binds to or coordinates the central radionuclide atom through the chelator's atoms. The chelator is typically a bifunctional molecule allowing to (i) form complexes with the radionuclide (a) and (ii) to link the chelator (b) to the peptidic component (c) of the inventive radiopeptide. In one embodiment, the chelator is of an open chain structure, e.g. DTPA (diethylenetriaminepentaacetic acid) or a DTPA derivative. In another preferred embodiment, the chelator is of cyclic structure. Particularly, the chelator may be a macrocyclic chelator. Further, the chelator may be a multidentate chelator, e.g. a tetradentate chelator.

The ring structure of the (macro)cyclic chelator may contain heteroatoms for coordination of the radioisotope, such as O or N, in particular N. In one embodiment, the macrocyclic chelator is based on a carbocyclic structure containing 4 to 6, in particular 4 heteroatoms, more specifically 4 N atoms, acting as atoms for binding to or coordinating the central radionuclide. Advantageously, the macro) cyclic basic structure of the chelator of the radiopeptide of the present invention is derived from cyclen (1,4,7,10-tetraazacyclododecane), which corresponds to a 12-membered tetraaza ring system. The tetraaza ring system may be further modified by substituents, e.g. substituents which bind to or coordinate the central radionuclide. Thereby, e.g. two such substituents may establish—in addition to the coordination by e.g. four N atoms of the cyclen ring system—an octahedral coordination geometry of the complex. One or more of the four, e.g. all four, secondary amine groups of cyclen's tetraaza ring system may be modified by replacement of the N—H centers with an N—X group with X being other than H. X may be $CH_2CO_2H$ or another substituent carrying a carboxy function. In this regard, the chelator may be, DOTAGA(-tetra) (2-[1,4,7,10-tetraazacyclododecane-4,7,10-tris(t-butylacetate)]-pentaedioic acid-1t-butylester), AAZTA (1,4-bis(carboxymethyl)-6-[bis(carboxymethyl)]amino-6-methylperhydro-1,4-diazepine), DOTA (dodecane tetraacetic acid) or a DOTAGA, AAZTA or DOTA derivative, e.g. CyAAZTA, DATA or AAZ3A. The DOTA derivative may exhibit a substitution pattern of the cyclen ring system other than the DOTA substitution pattern. Thus, a DOTA derivative may represent a substitution pattern, which is different from the acetic acids (characterizing DOTA) at at least one of the ring system's heteroatoms.

A DOTA derivative to be employed by the present invention may be selected from the group consisting of: DO3A, DO2A, HP-DO3A, BT-DO3A, PCTA, DO3AP, DO2A2P, DOA3P, DOTP, DOTPMB, DOTAMAE, DOTMA, TCE-DOTA, and DOTAMAP.

DOTA or one of its derivatives may be a preferred chelator for trivalent radiometals, as exemplified by terbium-161. The chelator of the inventive radiopeptide, in particular DOTA or a DOTA derivative may advantageously be complexed to terbium-161 by complex formation at elevated temperatures (e.g. between 70° C. and 95° C.) or by applying microwave irradiation or by using solvent mixtures or by a combination thereof in order to accelerate complex formation. In contrast, complex formation proceeds rather slowly at room temperature without applying more elaborate conditions. Once the radioisotope is inside the DOTA or DOTA derivative cavity, it remains therein stably at room temperature. Thus, the complex may be stored at room temperature without loss of activity by dissociation of the terbium-161 radioisotope from its chelator.

More specifically, DOTA is used as the chelator of the inventive radiopeptide.

In one embodiment of the invention, the radiopeptide is a conjugate compound characterized by coupling the (c) somatostatin receptor (SSTR) antagonist covalently to the (b) chelator. That coupling may involve the N-terminal amino group of the peptidic somatostatin receptor (SSTR) antagonist. Thereby, the peptidic somatostatin receptor (SSTR) antagonist and the chelator may form e.g. amide bond, in particular by reaction of the N-terminal amino group with a carboxy function of the chelator, e.g. the carboxy function of a substituent of the cyclen ring system. In this regard, e.g. the chelator's carboxy function, e.g. its N—$CH_2CO_2H$ group (with N being a nitrogen atom of the cyclen's ring system) may e.g. react with the N-terminal amino group of the peptidic component (c) to form a conjugate compound. The below formulae exemplify embodiments of the inventive radiopeptide comprising various chelators (DOTA or DOTA derivatives) being linked via an amide linkage to the peptidic component (c) (not shown by the below formulae) of the radiopeptide of the invention:

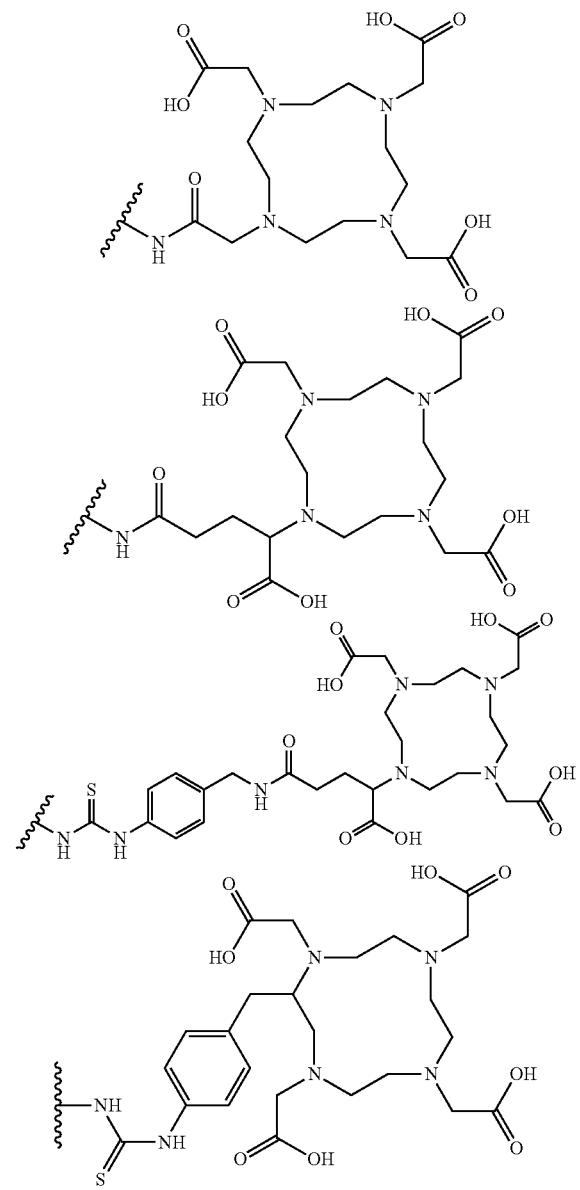

The radiopeptide of the present invention is further characterized by its component (c). Component (c) is a somatostatin receptor antagonist. Somatostatin receptor (sstr) targeting by sstr antagonists is a valuable therapy option for the treatment of e.g. neuroendocrine neoplasms. The sstr antagonist (c) advantageously forms a conjugate compound with the chelator (b), as described above. The sstr antagonist as defined for component (c) of the invention may bind to any sstr subtype. More specifically, however, it preferentially or exclusively binds to SSTR-2 (sst2). Somatostatin receptor 2 is a G-protein coupled receptor (GPCR) typically expressed in neuroendocrine tumors. SSTR2 is a receptor for somatostatin (SST)-14 and (SST)-28, respectively. Overexpression of SSTR2 in tumors can be exploited to selectively deliver radiopeptides to tumors. By their tumor cell binding, the radioactivity of the radioisotope or, rather, the radionuclide's particle emission (a) allows to damage and, finally, destroy tumor cells. The peptidic component (c) may thus, in particular, be an SSTR-2 (sst2) selective antagonist.

The somatostatin receptor (SSTR) antagonist thus allows the inventive radiopeptide to bind to tumor cells. Thereby, the selection of SSTR antagonists as component (c) advantageously supports the accumulation of the inventive radiopeptide on the tumor cells and, thereby, a significantly higher accumulation of radioactivity on the cell membrane of tumor cells, as SSTR antagonists recognize a much larger number of binding sites on the cell membrane-anchored SSTR than radiolabelled SSTR agonists Thereby, radiolabeled SSTR antagonists allow to present to tumor cells a significantly higher radioactivity than their agonistic counterparts.

Advantageously, the radiopeptide comprising the (peptide as the) antagonistic component (c) as the tumor cell binding entity is not significantly internalized by the tumor cell due to poor internalization rates, but remains on the tumor cell's surface. Thus, less than 30%, less than 25%, less than 20% or less than 10% of the administered radiopeptide may be internalized by the tumor cells under in vivo or in vitro conditions. Component (c) may thus advantageously represent an antagonistic somatostatin analogue (or an SSTR antagonist) which targets an sstr, more specifically sstr2, but is not or only in minor amounts (e.g. by less than 30% or less than 20%) internalized by the target tumor cells. The retention of a larger portion of the radiopeptide on the cell surface membrane upon binding to its target sstr may act in a therapeutically synergistic manner or may further contribute to the therapeutic effect due to the combined β−/Auger electron emission by terbium-161.

The radiopeptide's somatostatin receptor antagonist may be a peptide or peptide analogue comprising naturally or non-naturally occurring amino acids. The radiopeptides of the present invention may be in the form of a free peptide, or in the form of a salt, solvate or tautomer thereof. The term "peptide" defining the peptidic component of the "radiopeptide" as used herein refers to any sequence of amino acids, regardless of length or modification or the character of the amino acids. The naturally or non-naturally occurring amino acids may be D- or L-amino acids, i.e. in the D- or L-configuration. They are linked via amide bonds to one another. While any reactive side chain group of the somatostatin receptor antagonist may enable a covalent linkage to the chelator component for forming a conjugate compound, the antagonist's N-terminal free amino group may be specifically involved in its covalent linkage to the radiopeptide's chelator component. The peptidic antagonist may typically comprise at least 8 naturally or non-naturally occurring amino acids. More specifically, the number of amino acids is 8 to 14 amino acids or 8 to 10 or 8 amino acids.

In one embodiment, the antagonist as component (c) of the inventive radiopeptide is provided as a cyclic peptide. The cyclic structure may be introduced by a covalent linkage between two side chain moieties. In particular, ring closure by two side chain moieties may be realized by two cysteine residues forming a disulfide bridge by their free thiol groups. When forming a disulfide bridge based cyclic structure, the cysteine residues may be positioned within the antagonist's peptide sequence such that they are separated by at least 3, at least four or at least five amino acids, more specifically separated by 3, 4 or 5 amino acids in between. By a specific embodiment, the cysteine residues are separated from each other by 4 amino acids. The more N-terminal cysteine residue being involved in the disulfide bridge formation may be positioned at position 2 or 3 of the antagonist's peptide sequence. The more C-terminal cysteine residue being involved in the disulfide bridge formation may be positioned at position 7 or 8 of the antagonist's peptide sequence. In particular, the two disulfide bridge forming cysteine residues may be located at position 2 and 7, respectively, of the antagonist's peptide sequence.

The carboxy terminus of the peptide antagonist of the radiopeptide of the invention may be amidated, as e.g. shown in formula (I) below or for embodiments (i) to (xxv) below ("—NH$_2$").

Non-naturally occurring amino acids of the component (c) may be specifically selected from the group consisting of (4-amino-Phe(carbamoyl), (Aph(Cbm), D-Agl(NMe.benzoyl), Aph(Hor), Aph(CONH—OCH$_3$), substituted Phe, and Cpa. They may all be provided as D- or L-enantiomers. In addition, all naturally occurring amino acids may be used as their D-enantiomer as well.

According to one embodiment, the somatostatin receptor antagonist as component (c) of the inventive radiopeptide may comprise a sequence according to formula I:

(formula (I)
(SEQ ID NO: 1)
X1-cyclo[D-Cys-X3-X4-Lys-Thr-Cys]-D-Tyr-NH$_2$, or salts, solvates or tautomers thereof,
wherein X1, X3, and X4 may be selected from any naturally or a non-naturally occurring D- or L-amino acid.

More specifically, (i) X1 may be selected from the group consisting of naturally occurring Phe, a substituted Phe having one or more substitutions at the phenyl ring system and Cpa; (ii) X3 may be selected from the group consisting of Aph(Hor), Leu, L-Agl(NMe.benzoyl), D-Agl(NMe.benzoyl), Aph(Cbm), Tyr, Aph(CONH—OCH$_3$), Aph(CONH—OH); and/or (iii) X4 may be selected from the group consisting of D-Trp and D-Aph(Cbm) (D-4-amino-Phe(carbamoyl)). In particular, the peptidic antagonist of formula (I) may comprise an amino acid as defined above for X1 according to (i), for X3 according to (ii) and for X4 according to (iii).

When selecting a substituted Phe residue for X1, the at least one phenyl ring substituent may be positioned at an ortho (o), meta (m) or para (p) position of the phenyl ring system, more specifically at the para (p) ring position. The at least one substituent at the phenyl ring at position X1 may typically not represent a bulky substituent, but a sterically less prominent substituent, such as a halogen, amino, hydroxy or nitro group. Typically, the phenyl ring system of a substituted Phe residue may be substituted by one or two substituent(s), more specifically by one substituent. If the phenyl ring system is substituted by one substituent, the substituent may be specifically positioned at the para position of the Phe ring system. It may e.g. be chosen from a nitro group or halogen, such as Cl.

A more specific embodiment according to formula (I) may be based on: (i) X1 may be selected from the group consisting of pNO$_2$-Phe, pCl-Phe and Cpa; (ii) X3 may be selected from the group consisting of Tyr, Aph(Cbm), and Aph(Hor); and/or (iii) X4 may be selected from D-Trp and D-Aph(Cbm). In particular, the peptidic antagonist of formula (I) may comprise an amino acid as defined above for X1 according to (i), for X3 according to (ii) and for X4 according to (iii) as defined by this paragraph.

As a more specific embodiment, in particular of formula (I), the radiopeptide of the invention may comprise a somatostatin receptor antagonist, which is selected from the group consisting of LM3 ([p-Cl-Phe-cyclo[D-Cys-Tyr-D-Aph(Cbm)-Lys-Thr-Cys]-D-Tyr-NH$_2$]) (SEQ ID NO:2), JR11 (Cpa-cyclo[D-Cys-Aph(Hor)-D-Aph(Cbm)-Lys-Thr-Cys]-D-Tyr-NH$_2$) (SEQ ID NO:3), JR10 (p-NO$_2$-Phe-cyclo[D-Cys-Tyr-D-Aph(Cbm)-Lys-Thr-Cys]-D-Tyr-NH$_2$) (SEQ ID NO:5), and BASS (pNO$_2$-Phe-cyclo[D-Cys-Tyr-D-Trp-Lys-Thr-Cys]-D-Tyr-NH$_2$) (SEQ ID NO:4). All of the antagonists LM3, JR10, JR11, and BASS act as sstr-2 selective antagonists.

According to another embodiment, an antagonist as component (c) of the radiopeptide of the present invention may be selected from the group consisting of:

(i)
(SEQ ID NO: 4)
pNO2-Phe-cyclo[D-Cys-Tyr-D-Trp-Lys-Thr-Cys]-D-Tyr-NH$_2$;

(ii)
(SEQ ID NO: 5)
pNO2-Phe-cyclo[D-Cys-Tyr-D-Aph(Cbm)-Lys-Thr-Cys]-D-Tyr-NH$_2$;

(iii)
(SEQ ID NO: 6)
H2N-pNO$_2$-Phe-cyclo[D-Cys-Tyr-D-Aph(Cbm)-Lys-Thr-Cys]-2Nal-NH$_2$;

(iv)
(SEQ ID NO: 7)
pNO2-Phe-cyclo[D-Cys-Tyr-D-Aph(Cbm)-Lys-Thr-Cys]-2Nal-NH$_2$;

(v)
(SEQ ID NO: 8)
pNO2-Phe-cyclo[D-Cys-Aph(Hor)-D-Aph(Cbm)-Lys-Thr-Cys]-2Nal-NH$_2$;

(vi)
(SEQ ID NO: 9)
Cpa-cyclo[D-Cys-L-Agl(NMe.benzoyl)-D-Trp-Lys-Thr-Cys]-2Nal-NH$_2$;

(vii)
(SEQ ID NO: 10)
Cpa-cyclo[D-Cys-D-Agl(NMe.benzoyl)-D-Trp-Lys-Thr-Cys]-2Nal-NH$_2$;

(viii)
(SEQ ID NO: 11)
Cpa-cyclo[D-Cys-Leu-D-Trp-Lys-Thr-Cys]-2Nal-NH$_2$;

(ix)
(SEQ ID NO: 12)
Cpa-cyclo[D-Cys-Aph(Cbm)-D-Trp-Lys-Thr-Cys]-2Nal-NH$_2$;

(x)
(SEQ ID NO: 13)
Cbm-Cpa-cyclo[D-Cys-Aph(Cbm)-D-Trp-Lys-Thr-Cys]-2Nal-NH$_2$;

(xi)
(SEQ ID NO: 14)
[beta]Ala-Cpa-cyclo[D-Cys-Aph(Cbm)-D-Trp-Lys-Thr-Cys]-2Nal-NH$_2$;

(xii)
(SEQ ID NO: 15)
Cpa-cyclo[D-Cys-Aph(Cbm)-D-Trp-Lys-Thr-Cys]-2Nal-NH$_2$;

(xiii)
(SEQ ID NO: 16)
Cpa-cyclo[D-Cys-Aph(Cbm)-D-Trp-Lys-Thr-Cys]-NH$_2$;

(xiv)
(SEQ ID NO: 17)
Cpa-cyclo[D-Cys-Aph(Cbm)-D-Trp-Lys-Thr-Cys]-Cha-NH$_2$;

(xv)
(SEQ ID NO: 18)
Cpa-cyclo[D-Cys-Aph(Cbm)-D-Trp-Lys-Thr-Cys]-Aph(Hor)-NH$_2$;

(xvi)
(SEQ ID NO: 19)
Cpa-cyclo[D-Cys-Aph(Cbm)-D-Trp-Lys-Thr-Cys]-DAph(Cbm)-NH$_2$;

(xvii)
(SEQ ID NO: 20)
Cpa-cyclo[D-Cys-Aph(Cbm)-D-Trp-Lys-Thr-Cys]-Aph(Cbm)-NH$_2$;

(xviii)
(SEQ ID NO: 21)
Cpa-cyclo[D-Cys-Aph(Cbm)-D-Trp-Lys-Thr-Cys]-D-Aph(Cbm)-GlyOH;

(xix)
(SEQ ID NO: 22)
Cpa-cyclo[D-Cys-Aph(CONH-OCH3)-D-Trp-Lys-Thr-Cys]-2Nal-NH$_2$;

(xx)
(SEQ ID NO: 23)
Cpa-cyclo[D-Cys-Aph(CONH-OH)-D-Trp-Lys-Thr-Cys]-2Nal-NH$_2$;

(xxi)
(SEQ ID NO: 24)
Cpa-cyclo[D-Cys-Aph(Cbm)-5F-D-Trp-Lys-Thr-Cys]-2Nal-NH$_2$;

(xxii)
(SEQ ID NO: 25)
Cpa-cyclo[D-Cys-Aph(Cbm)-5F-Trp-Lys-Thr-Cys]-2Nal-NH$_2$;

(xxiii)
(SEQ ID NO: 26)
Cpa-cyclo[D-Cys-Tyr-D-Aph(Cbm)-Lys-Thr-Cys]-2Nal-NH$_2$;

-continued (xxiv)
(SEQ ID NO: 27)
Cpa-cyclo[D-Cys-Aph(Hor)-D-Aph(Cbm)-Lys-Thr-

Cys]-2Nal-NH$_2$;
and (xxv)
(SEQ ID NO: 3)
Cpa-cyclo[D-Cys-Aph(Hor)-D-Aph(Cbm)-Lys-Thr-Cys]-

D-Tyr-NH$_2$.

or salts, solvates or tautomers thereof.

The radiopeptide of the present invention may be selectively accumulated in the tumor tissue of a tumor patient in vivo. Thereby, the radiopeptide accumulates in a much less pronounced manner in tissue other than tumor tissue. Preferential accumulation within the tumor tissue may be expressed by the ratio of radiopeptide uptake in tumor cells to radiopeptide uptake in other tissues, e.g. kidney, liver, or blood. The tumor/blood uptake ratio characterizing an inventive radiopeptide may be at least 50.0 or at least 75 or at least 100. The tumor/liver uptake ratio of radiopeptide may be at least 10.0 or at least 20. The ratio may be determined as shown in the biodistribution in vivo studies (section III.) below. The tumor/kidney uptake ratio may be at least 2.0. That measurement may be carried at least 2 hours after administration of the radiopeptide to a subject, typically 2 or 4 hours after administration of the radiopeptide to the subject.

By a specific embodiment of the present invention, the inventive radiopeptide has the following structure:

includes peptides or peptide/chelator conjugates or radiopeptides of the present invention which are capable of existing in a state of equilibrium between two isomeric forms. Such compounds may differ in the bond connecting two atoms or groups and the position of these atoms or groups in the compound.

Radiopeptides of the invention may be administered in the form of pharmaceutically or veterinarily acceptable non-toxic salts, such as acid addition salts or metal complexes, e.g., with zinc, iron, calcium, barium, magnesium, aluminum or the like. Such non-toxic salts may be hydrochloride, hydrobromide, sulphate, phosphate, tannate, oxalate, fumarate, gluconate, alginate, maleate, acetate, citrate, benzoate, succinate, malate, ascorbate, tartrate and the like.

Another aspect of the present invention refers to a pharmaceutical composition, comprising the radiopeptide as described herein and at least one pharmaceutically acceptable excipient. More specifically, the pharmaceutical composition may be a liquid formulation. It may be an aqueous solution, optionally containing a buffer system. The aqueous pharmaceutical composition of the invention may comprise another water-miscible solvent, e.g. ethanol. Typically, the aqueous solution may not contain more than 10% of another solvent, e.g. ethanol, by volume. The pharmaceutical composition may have a pH in the range of pH 3 to pH 7, more specifically in the range of pH 3.5 to pH 6 or pH 4 to pH 6.

The pharmaceutical composition according to the invention comprises 0.001 to 1 mg/ml radiopeptide as defined herein, depending on the subject to be treated or the disease to be treated. Specifically, the concentration of the radiopeptide may be in the range of 0.01 to 1 or 0.5 mg/ml or 0.05 to 0.5 mg/ml.

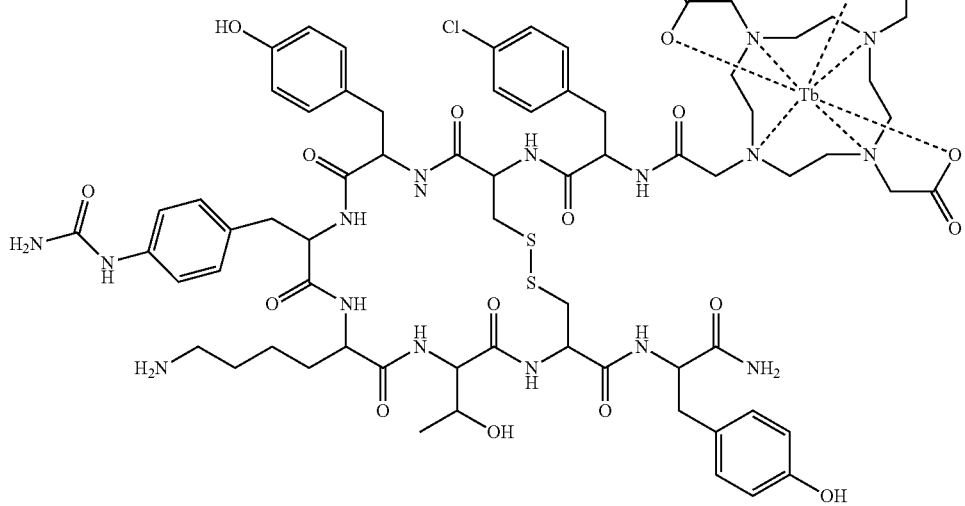

Therein, the radionuclide terbium-161 is complexed by the DOTA chelator establishing an octahedral coordination geometry of the complex. The DOTA chelator is covalently conjugated via an amide linker to the N-terminus of the sstr2 selective antagonist LM3. Its carboxy terminus is amidated.

More generally, peptide antagonists or peptide antagonist/chelator conjugates or radiopeptides as described herein above may form solvates with water (such as hydrates or hemihydrates) or common organic solvents. The term "tautomer" as used herein is used in its broadest sense and The pharmaceutical composition may contain at least one, e.g. 1, 2 or 3 of the additives of the group consisting of gentisic acid, ethanol, acetate, NaCl and ascorbic acid/ascorbate.

In one embodiment, the pharmaceutical composition comprises the antioxidant ascorbic acid/ascorbate as a stabilizer. The presence of ascorbic acid/ascorbate, which typically acts as scavengers, may stabilize the pharmaceutical composition, thereby enhancing the shelf life of the pharmaceutical composition, while maintaining the pharmaceutical composition as suitable for administration to a human, and other mammalian subjects. The pharmaceutical composition may thus comprise greater than about 5 mg of ascorbic acid per milliliter or greater than about 10 mg of ascorbic acid per milliliter or greater than about 20 mg of ascorbic acid per milliliter or greater than about 30 mg of ascorbic acid per milliliter or greater than about 40 mg of ascorbic acid per milliliter or greater than about 50 mg of ascorbic acid per milliliter or greater than about 100 mg of ascorbic acid per milliliter or greater than about 200 mg of ascorbic acid per milliliter. The pharmaceutical composition may thus contain 5 to 100 mg/ml of ascorbic acid/ascorbic acid or 25 to 500 mg/ml or 50 to 200 mg/ml. To put it differently, the pharmaceutical composition may comprise ascorbic acid/ascorbate in the range of 0.5 mM to 0.5 M, in particular 1 mM to 100 mM or 10 mM to 100 mM.

The pharmaceutical composition may exhibit a radioactivity in the range of 50 to 800 MBq/ml or 100 to 600 MBq/ml or 200 to 400 MBq/ml.

In another aspect, the present invention refers a method of treating a disease, in particular a tumor disease. The method of treatment may comprise administering a radiopeptide of the invention or a composition of the invention to a subject in need of a disease treatment, in particular in need of a neoplasm or tumor treatment. The subject may be mammal, in particular a human.

The radiopeptide of the invention or a nontoxic salt thereof, typically combined with a pharmaceutically or veterinarily acceptable carrier/excipient to form a pharmaceutical composition of the invention may be administered to animals, including humans and other mammals, either intravenously, subcutaneously, intramuscularly, percutaneously, e.g. intranasally, intracerebrospinally or orally. Specifically, the radiopeptide of the invention or the pharmaceutical composition of the invention may be administered systemically, preferably intravenously, e.g. through infusion drip. The pharmaceutical composition may be administered over an extended period of time, e.g. for 10 to 60 min, by infusion, e.g. by a catheter or heparin lock line to be prepared into the vein of a subject, and may be flush with the appropriate saline and or heparin solution. The dose may be administered via luer-lock into the catheter or heparin lock line. The site of administration may depend on the patient's tumor/metastases profile. One specific site of administration may be the arm vein.

The treatment protocol depends on the tumor disease, the severity of the tumor disease and the therapy progress, which is typically monitored by PET/CT or SPECT/CT scans after each treatment cycle. SPECT may preferably serve as a technology to study the distribution of the radiopeptide in the body. In one embodiment, the treatment protocol may comprise 2 to 10 treatment cycles, e.g. 4, 5, 6 or 7 treatment cycles. The treatment protocol may thus foresee two or more treatment cycles every 4 to 10 weeks, e.g. every 5 to 8 weeks or about every 6 weeks. In case of disease progression, retreatment may be envisaged after the initial treatment cycle protocol.

Such a pharmaceutical composition designed to be used for treating tumors, e.g. benign or malignant tumors, including the treatment of metastases thereof in other tissues, may be administered in a quantity sufficient for treating or controlling tumors. The radiopeptide should be at least about 90% pure and may preferably have a purity of at least about 98%; however, lower purities are effective and may well be used with mammals other than humans. This purity means that the intended peptide constitutes the stated weight % of all like peptides and peptide fragments present in the composition. The required dosage will vary with the particular condition being treated, with the severity of the condition and with the duration of envisaged treatment.

More specifically, the disease to be treated by the radiopeptide or the pharmaceutical composition of the invention is a neoplasm that arises from cells of the endocrine (hormonal) and (peripheral) nervous system. Abnormal cells of neoplasms or tumors to be treated typically express sstr2 at their cell surface. They may occur in a larger variety of tissues, most commonly they occur in the intestine. The neoplasm may thus be a neuroendocrine neoplasm in the gastroenteropancreatic (e.g. foregut, midgut, hindgut, or pancreas: pancreatic islet cells) or bronchopulmonary tract. It is understood that the inventive method may involve the treatment of a neuroendocrine neoplasm in a larger variety of tissues and/or of neuroendocrine tumor metastases, in particular liver metastases. The neuroendocrine neoplasm/tumor may be benign or malignant. Their histological grading may—according to the WHO's grading scheme—be graded as G1, G2 or G3. While differentiated neuroendocrine neoplasms of the gastroenteropancreatic system which are graded as G1, G2, and G3, are defined as neuroendocrine tumors, poorly differentiated neuroendocrine neoplasms of the gastroenteropancreatic system of G3 grade correspond to neuroendocrine carcinomas. The present invention provides a method of treating differentiated or poorly differentiated neuroendocrine tumors or carcinomas of the gastroenteropancreatic system, e.g. a pancreatic tumor or carcinoma.

Various other organs may be affected by a neuroendocrine neoplasm/tumor and its metastases. Thus, neuroendocrine tumors of the lung may be treated according to the invention, e.g. a neuroendocrine carcinoma of the lung or bronchial tract, including small cell lung cancer. Adrenal tumors, particularly adrenomedullary tumors, may be treated, e.g. pheochromocytoma as a tumor of the adrenal medulla as well by the inventive method. Tumors of the peripheral nervous system, e.g. paraganglioma, Schwannoma or neuroblastoma may be tumor diseases for a treatment by the inventive method. Tumors of the thymus, thyroid or pituitary gland may be treated as well, e.g. neuroendocrine thyroid tumors, particularly medullary thyroid carcinoma. Breast cancer or carcinoma of the genitourinary tract may be treated by the inventive method as well. Prostate cancer may be treated as well, in particular prostate cancer of neuroendocrine origin. Also, the inventive method may be applied for the treatment of meningioma, renal cell carcinoma, and non-Hodgkin lymphoma.

Advantageously, the therapy method as described herein may be preceded by an imaging step (e.g. PET/CT-scans and/or MRI) allowing to determine the uptake, e.g. by determining uptake values (SUV), of a tracer dose of the inventive radiopeptide by the abnormal cells of the neoplasm of tumor. Thereby, tumor patients with high level expression of somatostatin receptor, e.g. somatostatin receptor subtype 2 (sstr2), are selected which allow to be successfully treated by the inventive approach. Alternatively or additionally, the tumor cells may be analyzed by the methods of molecular biology or in vitro diagnostics for determining sstr-positive or sstr2-positive cells, i.e. their sstr expression level on the tumor cell surface.

The therapy approach is highly effective for the treatment of tumors with minimal side effects in other non-tumorigenic tissues. The radiopeptide accumulates with rapid kinetics at the tumor sites in the body. The radiopeptides radiation is essentially absorbed at the sites of the tumor, or excreted in the urine such that other tissues remain essentially unaffected by the radioisotope's (β⁻)-particle radiation. The terbium-161 labelled antagonistic somatostatin analogues bind to or enter into, preferably bind to tumor cells which are damaged by the radioisotope's radiation. The tumor cells are thereafter subject to apoptotic or necrotic events such that the subject's tumor load is reduced as a result of the therapy.

In a specific embodiment, the therapy approach of the invention is applied to patients which suffer from a primary endocrine neoplasm/tumor and, potentially, metastases thereof.

In another embodiment, the therapy method based on the inventive radiopeptide may be carried out in combination with concomitant treatments. In particular, renal protection may be envisaged by concomitant infusion of solutions containing amino acids, such as Arg or Lys. Concomitant treatment by such an amino acid solution may e.g. start 3 h to 0.2 h, typically about 1 to about 1.5 h before and may be continued for another 1 to 5 h after the end of the administration of the radiopeptide. Also, the patient may be pretreated by an antiemetic and/or corticosteroid prior to a treatment cycle with the radiopeptide of the invention.

In a specific embodiment, the present invention allows for the treatment of neuroendocrine neoplasms/tumors and other SSTR2-positive neoplasms, which are stable or refractory to a therapy by $^{90}$Y-DOTATOC, $^{177}$Lu-DOTATOC, ($^{177}$Lu)-Oxodotreotid (Lutathera®); $^{177}$Lu-DOTATATE) and other radiolabelled somatostain analogues, in particular $^{177}$Lu-DOTATOC or ($^{177}$Lu)-Oxodotreotid (Lutathera®); more particularly ($^{177}$Lu)-Oxodotreotid (Lutathera®); $^{177}$Lu-DOTATATE.

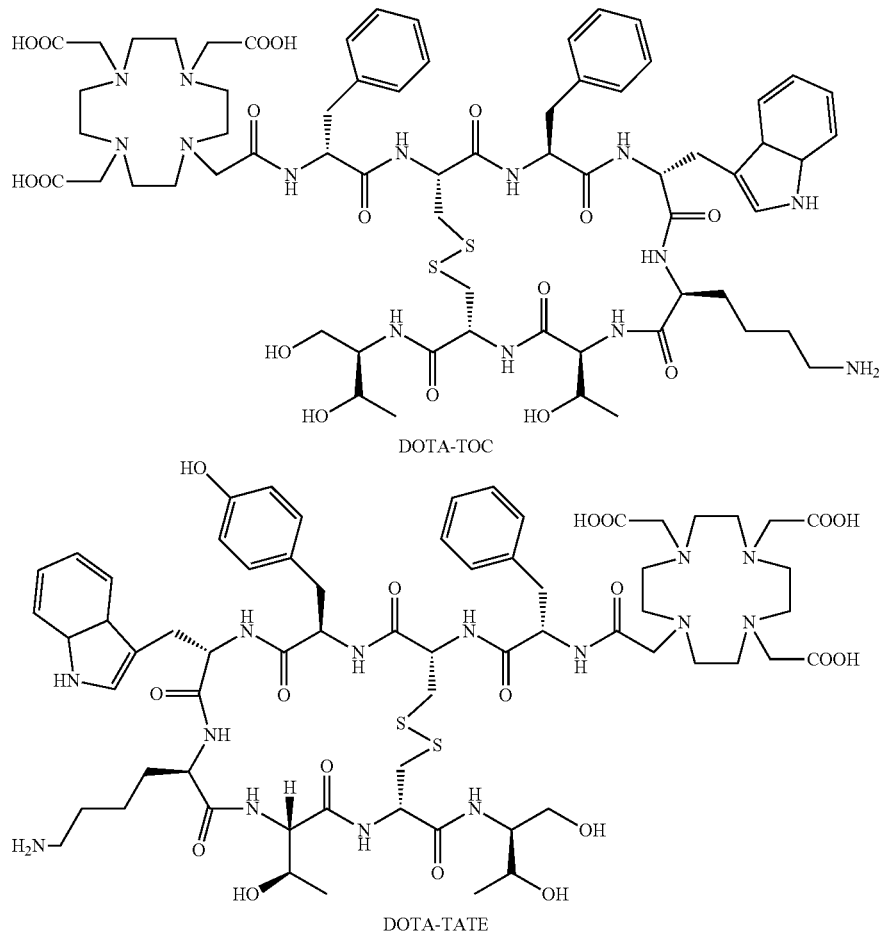

By another aspect, the present invention provides a kit or a kit of parts.

A labelling reaction with the radionuclide may be required to be carried out in a clinical hospital or laboratory setting prior to the treatment. In such instances, the various reaction ingredients may be provided to the user in the form of a "kit" or "kits". Accordingly, a kit for preparing a pharmaceutical composition according to the present invention may comprise (i) a somatostatin receptor (SSTR) antagonist as described herein conjugated to the radionuclide's chelator, (ii) an inert pharmaceutically acceptable carrier and/or formulating agent with optional adjuvants, (iii) a solution of a salt of a radioactive metal isotope terbium-161, typically in the form of its salt, and, optionally, (iv) instructions for use with a prescription for reacting the ingredients present in the kit, all of the above as parts of a kit. Components (i), (ii), (iii) and, optionally, (iv) are typically provided as separate parts by the kit. Alternatively, component (iii) may be provided by a first kit, whereas components (i) and (ii) may be provided as parts by a separate second kit. The first and the second kit may thus be delivered as separate entities to the site of use allowing "right on time" provision of the radionuclide for its further formulation and subsequent therapeutic usage.

The somatostatin antagonist (peptidic component (c) of the radiopeptide) may be conjugated by a reaction with a chelating agent (component (b) of the radiopeptide) as defined hereinbefore. The resulting peptide/chelator conjugate provides an advantageous entity for stably complexing the radioisotope terbium-161 (component (a) of the radiopeptide) in a straight-forward manner at the site of use. The peptide/chelator conjugate, e.g. in the form of its salt, may be provided in dry form or, more typically, in solution as part of a kit, e.g. in a buffered or non-buffered aqueous solution. When being provided in dry form, it may be delivered in lyophilized form, such that the lyophilized conjugate has to be dissolved in solution at the site of use. Due to its character as an injection liquid, it should be sterile. When the constituent is in the dry state, the user should preferably use a sterile physiological saline solution as a solvent, which is optionally buffered.

When the radionuclide/-isotope is present in the kit comprising all parts or in a separate kit comprising (iii) the radionuclide as the only chemical entity, the radionuclide or its salt is typically provided in an aqueous acidic solution, e.g. in a hydrochloric acid solution, exhibiting a pH of e.g. <2 or <1. As the radionuclide is provided as separate kit or a separate part of a kit, the radionuclide has to be prepared for binding to the peptide/chelator conjugate by a complex-forming reaction. Advantageously, both the solution containing the peptide/chelator conjugate and the solution containing the radionuclide are combined. The solution containing the peptide/chelator conjugate may advantageously contain a buffer buffering the pH in the acidic range, e.g. acetate, allowing the complexation reaction to occur under appropriate acidic conditions. For preventing precipitation of the radioactive metal (e.g. by the formation of its hydroxy salt), the complexation reaction should not proceed under alkaline conditions. Advantageously, the complexation reaction is carried under conditions shifting the equilibrium towards complexation, e.g. by heating, e.g. to a temperature close to the solution's boiling point, the combined solutions of the radionuclide and the peptide/chelator conjugate.

In addition, the resulting product may be finally re-formulated by adding stabilization additives. Thereby, the above-mentioned terbium-161 complexed peptide/chelator conjugate may be stabilized with suitable stabilizers, for example, ethanol, ascorbic acid, gentisic acid or salts of these acids.

Embodiments of inventive compositions and methods are illustrated in the following examples. These examples are provided for illustrative purposes and are not considered limitations on the scope of inventive compositions and methods.

Examples

The Examples of the present disclosure show the impact of the cellular localization on the therapeutic effect of terbium-161 vs. lutetium-177 in vitro and in vivo. DOTA-TOC and DOTA-LM3 were used. They were labeled with $^{161}$Tb-labeled and $^{177}$Lu, respectively. The labelled $^{161}$Tb radiopeptides were compared with their $^{177}$Lu-labeled counterparts, in order to study whether the effects of conversion and Auger electrons emitted by terbium-161 may depend on the radionuclide's cellular localization. A one-to-one comparison of the therapeutic effect of terbium-161 and lutetium-177 was feasible due to equal behavior of the $^{161}$Tb- and $^{177}$Lu-counterparts with regards to the in vitro cell uptake and in vivo biodistribution [44].

The cellular localization of the radiopeptide was found to have an impact for its therapeutic effect, which in turn, was dependent on the employed radionuclide.

The difference in efficacy between the $^{161}$Tb- and $^{177}$Lu-labeled peptides was evidenced. It was most pronounced in the case of DOTA-LM3. [$^{161}$Tb]Tb-DOTA-LM3 revealed to be 102-fold more effective to reduce cell viability in vitro than [$^{177}$Lu]Lu-DOTA-LM3.

The preclinical therapy study confirmed that the 161Tb-labeled somatostatin analogues were more effective than their $^{177}$Lu-labeled counterparts in vivo. The therapeutic effect of radiolabeled DOTA-LM3 was significantly more pronounced than the effect of radiolabeled DOTATOC, which can be ascribed to the higher tumor uptake of radiolabeled DOTA-LM3 as demonstrated by the biodistribution data. It was found that 161Tb-labeled somatostatin receptor antagonist (DOTA-LM3) that localize on the cell membrane benefit from the use of terbium-161 over lutetium-177, suggesting the cell membrane as a valid target for terbium-161 as an Auger electron emitter.

I. Production

Terbium-161 and lutetium-177 were used for comparing the effects based on the cellular localization of the targeting agent. In this regard two different peptides were used: (i) DOTATOC, which localizes primarily in the cell cytosol and (ii) DOTA-LM3, which stays mainly at the cell membrane.

A. Production Methods of Radionuclides and Peptides

Terbium-161 was produced using the $^{160}$Gd(n,γ) $^{161}$Gd→$^{161}$Tb nuclear reaction as previously reported [1, 2]. The target material was irradiated at the SAFARI-1 reactor at Necsa in Pelindaba, South Africa or at the RHF at Institut Laue-Langevin in Grenoble, France or at the spallation-induced neutron source SINQ, Villigen-PSI, Switzerland. The chemical separation of terbium-161 was performed at PSI as previously reported [2]. Terbium-161 was made available as no-carrier-added (n.c.a.) [$^{161}$Tb]TbCl$_3$ in 0.05 M HCl. Lutetium-177 was obtained as n.c.a. [$^{177}$Lu]LuCl$_3$ in 0.04 M HCl from ITM Medical Isotopes GmbH, Germany.

Figure 1B:
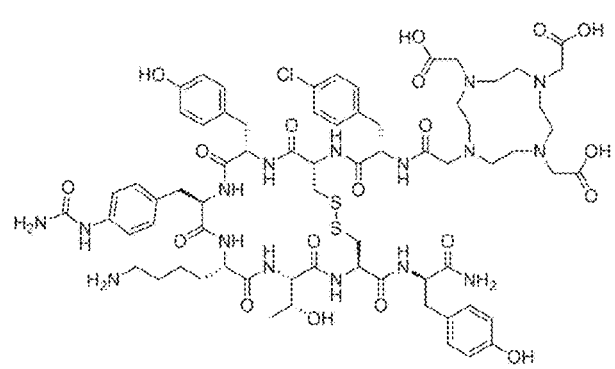

DOTA-[Tyr$^3$]-octreotide (DOTATOC) was provided by ITM GmbH, Germany (FIG. 1a). DOTA-LM3 was obtained as a custom synthesis by CSBio (Silicon Valley Menlo Park, California, U.S.A.) based on the structure published by Fani et al. (see FIG. 1b) [3, 4].

Terbium-161 was produced in high yields (average of >10 GBq up to 15 GBq/production at end of separation), at an activity concentration of 11-21 MBq/μL and ≥99% radionuclidic and radiochemical purity [43]. The radiolabeling of the peptides of up to 100 MBq/nmol was possible up to two weeks after chemical separation, enabling planning and performing the preclinical studies. The exact product specifications of terbium-161 were comparable to that of n.c.a. lutetium-177 as reported by Gracheva et al. [43].

B. Preparation of the Radiopeptides

[$^{161}$Tb]Tb-DOTATOC and [$^{161}$Tb]Tb-DOTA-LM3 as well as [$^{177}$Lu]Lu-DOTATOC and [$^{177}$Lu]Lu-DOTA-LM3 were prepared at high molar activity for the in vitro and in vivo evaluation and comparison of the radiopeptides.

The stock solutions of DOTATOC and DOTA-LM3 were prepared in Milli-Q water to obtain a final concentration of 1 mM. The somatostatin analogues were labeled with terbium-161 or lutetium-177 using a 1:5 (v/v) mixture of sodium acetate (0.5 M) and HCl (0.05 M) at pH ~4.5 at a molar activity up to 100 MBq/nmol, as previously reported [5]. The reaction mixture was incubated for 10 min at 95° C., followed by a quality control using HPLC. For this purpose, a Merck Hitachi LaChrom HPLC system, equipped with a D-7000 interface, a L-7200 autosampler, a radioactivity detector (LB 506 B; Berthold) and a L-7100 pump connected with a reversed-phase C18 column (Xterra™ MS, C18, 5 μm, 150×4.6 mm; Waters) was used. The mobile phase consisted of 0.1% (v/v) TFA in Milli-Q water (A) and acetonitrile (B). A linear gradient of solution A (95-20%) and solvent B (5-80%) over 15 min was used at a flow rate of 1.0 mL/min. The radiopeptides were diluted in Milli-Q water containing pentasodium diethylenetriaminepentaacetate (Nas-DTPA; 50 μM) prior to injection into HPLC.

[$^{161}$Tb]Tb-DOTATOC and [$^{177}$Lu]Lu-DOTATOC as well as [$^{161}$Tb]Tb-DOTA-LM3 and [$^{177}$Lu]Lu-DOTA-LM3 were obtained at radiochemical purity of ≥98% up to a molar activity of 100 MBq/nmol (see FIG. 2).

C. Radiolytic Stability of the Radiopeptides

The stability of the radiolabeled somatostatin analogues was tested to confirm their integrity during in vitro and in vivo evaluation.

Radiolytic stability of the radiolabeled somatostatin analogues was assessed over a period of 24 h (n=2). For this purpose, DOTATOC and DOTA-LM3 were labeled with terbium-161 or lutetium-177 at a molar activity of 50 MBq/nmol. After quality control using HPLC (t=0, radiochemical purity ≥98%, set as 100%), the labeling solutions were diluted with saline to a final volume of 250 μL and an activity concentration of 40 MBq/mL and incubated at room temperature (RT) with and without addition of L-ascorbic acid (120 μg/10 MBq in the final volume of 250 μL). Potential degradation of the radiopeptides was determined after 1 h, 4 h and 24 h by analyzing a sample using HPLC. A quantitative assessment of the chromatograms was performed by expressing the integrated peak area of the intact product as percentage of the sum of integrated peak areas of the entire chromatogram comprising released terbium-161 and lutetium-177 as well as degradation products of unknown structure.

Figures 3A, 3B:
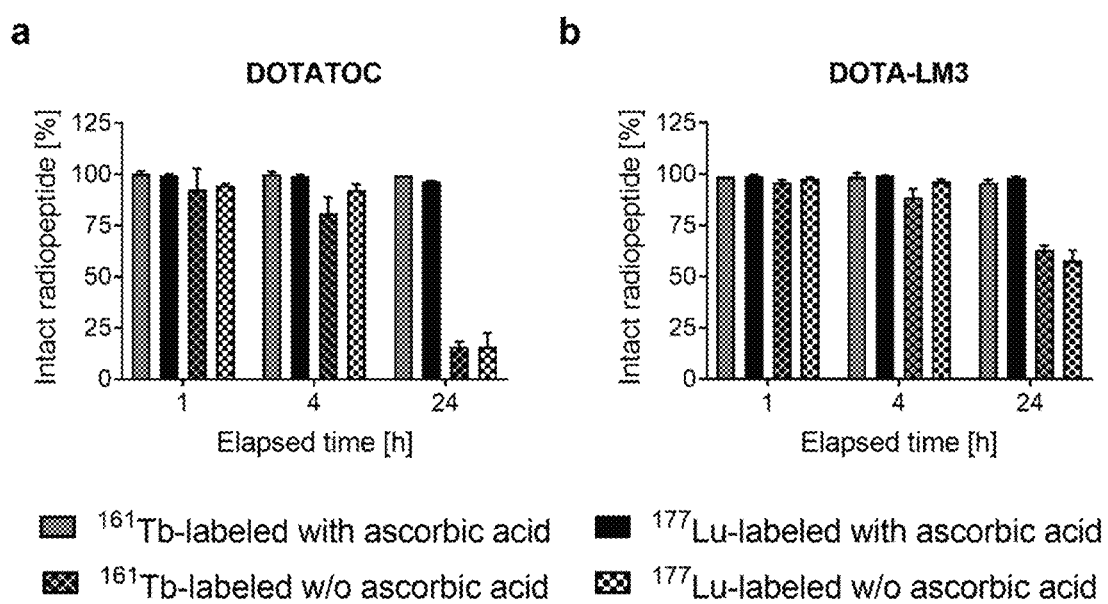
FIGS. 3A and 3B show graphs of bars representing the percentage of intact radiopeptide investigated at 1 h, 4 h and 24 h after preparation and dilution in saline (10 MBq/250 µL)

All radiopeptides, irrespective of whether labeled with terbium-161 or lutetium-177, were stable (>90% of intact radiopeptide) up to 1 h after preparation (see FIG. 3). The intact fraction was, however, reduced to ~90% and ~60% after 4 h and 24 h, respectively, due to radiolytic degradation. In line with published data [36, 43], the percentage of intact $^{161}$Tb- and $^{177}$Lu-labeled counterparts was identical, indicating that potential formation of additional reactive oxygen species (ROS) due to short-ranged conversion and Auger electrons [45] did not affect the radiopeptides' integrity. Stabilization of radiopeptides for clinical application is commonly achieved by the addition of ascorbic acid [46], which was also effective for the stabilization of the $^{161}$Tb- and $^{177}$Lu-labeled somatostatin analogues over longer periods (see FIG. 3).

If the radiopeptides were used at concentrations below 40 MBq/mL and/or immediately after preparation, the addition of L-ascorbic acid was not necessary. Dual-isotope SPECT/CT imaging studies were performed with activity concentrations above 40 MBq/mL (>4 MBq in 100 μL per mouse), which required the addition of L-ascorbic acid (~300 μg per 30 MBq in 100 μL) to ensure integrity of the radiopeptides.

D. Determination of n-Octanol/PBS Distribution Coefficients (Log D Values)

The n-octanol/PBS distribution coefficients (log D values) were assessed for each radiopeptide in order to investigate their hydrophilicity and enable comparison of the three analogues.

The log D values of the radiolabeled analogues (DOTATOC and DOTA-LM3; 30 MBq/nmol) were determined by a shake-flask method as previously reported [47]. An aliquot of the radiolabeled peptide (0.5 MBq, 25 μL) was added to a mixture of 1475 μL PBS pH 7.4 and 1500 μL n-octanol. The respective tubes were vortexed for 60 sec and centrifuged for 6 min at 2500 rpm followed by the measurement of the activity concentration in a defined volume of each layer using a γ-counter (Perkin Elmer, Wallac Wizard 1480). The log D values were calculated as the logarithm of the ratio of counts per minute (cpm) measured in the n-octanol phase relative to the cpm measured in the PBS pH 7.4 phase. The experiments were performed three times with five replicates for each radiopeptide and the log D value was expressed as the average±standard deviation (SD) of the values obtained in each experiment. The data were analyzed for significance using a two-way ANOVA with Tukey's multiple comparisons test. A p value <0.05 was considered statistically significant.

The radiopeptides showed a hydrophilic character as demonstrated by the low log D values. Importantly, the $^{161}$Tb- and $^{177}$Lu-labeled counterparts revealed similar log D values (p>0.05) (Table 1).

TABLE 1

LogD values of the radiopeptides presented as the average of 3 independent experiments performed in quintuplicate

| Radiopeptide | LogD | Radiopeptide | LogD | Significance |
|---|---|---|---|---|
| [$^{161}$Tb]Tb-DOTATOC | -3.3 ± 0.2 | [$^{177}$Lu]Lu-DOTATOC | -3.1 ± 0.2 | p > 0.05 |
| [$^{161}$Tb]Tb-DOTA-LM3 | 2.5 ± 0.1 | [$^{177}$Lu]Lu-DOTA-LM3 | -2.5 ± 0.1 | p > 0.05 |

II. In Vitro Studies

A. Cell Culture

AR42J tumor cells, a SSTR-positive exocrine rat pancreatic cancer cell line [48], was used for the in vitro and in vivo investigations in this study.

AR42J tumor cells (ECACC 93100618; Health Protection Agency Culture Collections, Salisbury, U.K.) were kept in RPMI 1640 culture medium supplemented with glutamine, antibiotics and 20% fetal calf serum as previously reported [44]. Cell culture medium containing glutamine and antibiotics but only 1% FCS (referred herein as "assay medium") was used for all in vitro assays. Incubation of cells always referred to standard culture conditions of a humidified atmosphere at 37° C. and 5% $CO_2$ if not otherwise indicated. Phosphate buffered saline (PBS) at the pH of 7.2 was used for the in vitro experiments if not otherwise indicated. Polystyrene well plates were coated with poly-L-lysine (0.5 mg/mL) for all in vitro experiments to facilitate cell adhesion and prevent adherence of the radiopeptides to the well-plate material.

B. Cell Uptake and Internalization: Comparison of $^{161}$Tb- and $^{177}$Lu-Labeled Peptides Cell uptake and internalization studies were performed with the $^{161}$Tb- and $^{177}$Lu-labeled counterparts of each radiopeptide.

The cell uptake and internalization studies were performed in AR42J tumor cells according to a previously published procedure [5]. AR42J tumor cells ($10^6$ cells/2 mL) were seeded in poly-L-lysine-coated 12-well-plates in RPMI medium with supplements and incubated overnight. After washing the cells with PBS (pH 7.4), assay medium (975 μL) and 25 μL radiopeptide solution (~15 kBq, ~0.75 pmol per well) were added to each well resulting in a radioligand concentration of 0.75 nM. The well-plates were incubated under standard cell culture conditions for 0.5 h, 2 h or 4 h. SSTR-blocking experiments were performed using 1 μM DOTANOC or 1 µM DOTA-LM3. The total uptake and the internalized fractions were determined using a γ-counter (Perkin Elmer, Wallac Wizard 1480). The activity of the samples was standardized to the average protein concentration in each well (~0.3 mg) using a Micro BCA Protein Assay kit (Pierce, Thermo Scientific). Experiments were performed twice or three times in triplicate. Statistical analysis was performed using a two-way ANOVA with Tukey's multiple comparisons post-test. A p value <0.05 was considered statistically significant.

The AR42J tumor cell uptake and internalization were equal for the respective $^{161}$Tb- and $^{177}$Lu-labeled SSTR analogues (p>0.05) (see FIG. 4). The uptake of [$^{161}$Tb]Tb-/[$^{177}$Lu]Lu-DOTATOC into AR42J cells was highest (~15% of total added activity) after 4 h incubation. Acid-washed cells retained 40-50% of the total uptake, which indicated efficient internalization of the radiopeptide-receptor complex as previously reported [49]. [$^{161}$Tb]Tb-/[$^{177}$Lu]Lu-DOTA-LM3 showed a AR42J cell uptake at all investigated time points and reached almost 70% after an incubation period of 4 h. The internalized fraction of radiolabeled DOTA-LM3 was, however, almost negligible (<10% of the total uptake) which is a characteristic feature of SSTR antagonists that were previously investigated [42]. The addition of excess DOTANOC prevented the cell uptake of [$^{161}$Tb]Tb-/[$^{177}$Lu]Lu-DOTATOC, which confirmed SSTR-specific binding of the radiopeptides. DOTANOC was, however, not effective to block the uptake of radiolabeled DOTA-LM3 completely (data not shown), because SSTR-antagonists can access more binding sites on the cell membrane (up to 14-fold) compared to SSTR-agonists [50]. The blocking was achieved using excess of unlabeled DOTA-LM3.

C. Cell Uptake and Internalization at Increasing Molar Amounts of Peptide

The aim of this in vitro studies was to determine the peptide amount which resulted in SSTR saturation in AR42J tumor cells after addition of the radiopeptides using variable amounts of DOTATOC and DOTA-LM3.

The uptake and internalized fraction of the peptides in AR42J tumor cells was determined using the same method described above, but the radiopeptides were applied using variable molar amounts of peptides. After washing the AR42J tumor cells with PBS (pH 7.4), they were incubated with 0.375-75 pmol of [$^{177}$Lu]Lu-DOTATOC or [$^{177}$Lu]Lu-DOTA-LM3 (25 µL, ~15 kBq). The cell uptake and internalized fraction were determined after an incubation period of 2 hours at 37° C. and the activity of the samples standardized to the average protein concentration in each well (~0.3 mg). Experiments were performed twice in triplicate.

Figures 5A, 5B:
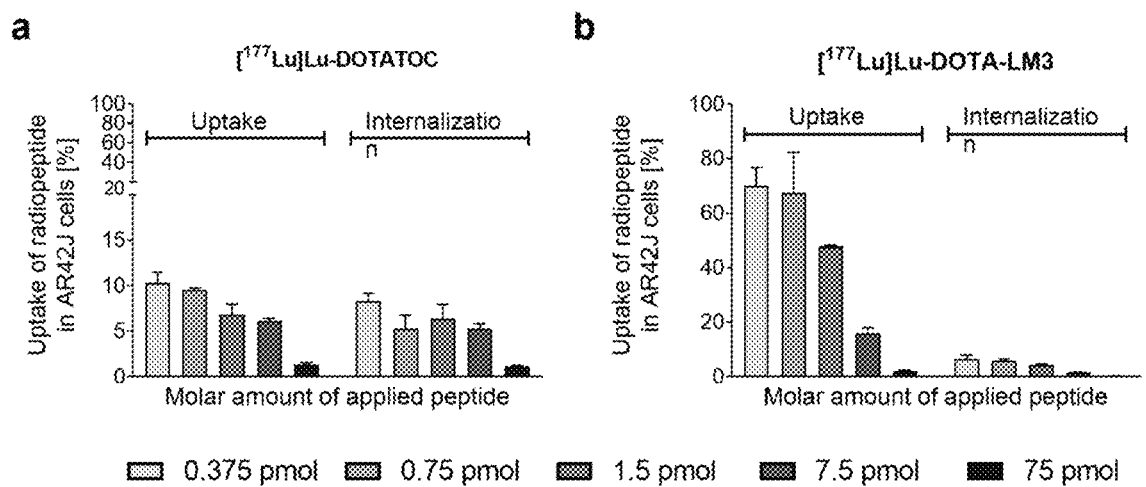
FIGS. 5A and 5B show graphs representing the uptake and internalized fraction of the radiopeptides applied at variable molar amounts of peptide using AR42J tumor cells. The AR42J tumor cells were incubated with the respective radiopeptide for a period of 2 h.

In all instances, the uptake and internalization of the respective radiopeptide decreased while increasing the molar amount of non-labeled peptide (see FIG. 5). Saturation of the SSTR was not observed at a peptide amount of 0.375 pmol and 0.75 pmol, but the uptake and internalization of [$^{177}$Lu]Lu-DOTATOC was decreased by ~30% when the peptide amount was 1.5 pmol and 7.5 pmol. At the highest applied molar amount of peptide (75 pmol), the uptake and internalization of [$^{177}$Lu]Lu-DOTATOC dropped by ~90%. The uptake of [$^{177}$Lu]Lu-DOTA-LM3 dropped by ~30%, if 1.5 pmol of peptide were applied, similarly to [$^{177}$Lu]Lu-DOTATOC. The uptake of [$^{177}$Lu]Lu-DOTA-LM3 dropped by ~80% at the molar amount of 7.5 pmol, whereas on these same conditions the uptake of $^{177}$Lu]Lu-DOTATOC decreased only by 30%.

D. Nuclear Localization of the Radiopeptides

AR42J tumor cells were incubated with the respective radiopeptide followed by isolation of the cellular nucleus in order to determine the fraction of radiopeptides that localized in the nucleus.

AR42J tumor cells (10×10$^6$) were seeded in PLL-coated Petri dishes using 15 mL of cell culture medium with supplements and incubated overnight at 37° C. and 5% $CO_2$. The next day, the medium was removed, the tumor cells were washed with PBS (pH 7.4) and 19.5 mL of assay medium was added. The radiopeptides were added in a volume of 0.5 mL (2.5 MBq, 125 pmol) and the tumor cells incubated for 2 h at 37° C. Afterwards, the cells were washed several times with PBS (pH 7.4) to completely remove excess of radiopeptides. Subsequently, the cell nuclei and cytoplasm/membrane fractions were harvested according to the manufacturer's protocol using the Nucli EZ Prep Nuclei Isolation Kit (Sigma Aldrich, USA). Ice-cold Nuclei EZ lysis buffer (4 mL) were added to each Petri dish to lyse the tumor cells followed by transfer of the cell suspension into Eppendorf tube for centrifugation for 5 min at 500 rcf at 4° C. The supernatant containing cytoplasm/membrane fractions was transferred to a tube for counting activity in a γ-counter. The pellet was resuspended in 4 mL ice-cold Nuclei EZ lysis buffer followed by additional centrifugation for 5 min at 500 rcf at 4° C. The supernatant containing residual cytoplasm/membrane fractions was collected for counting activity and the pellet was suspended in 200 µL Nuclei EZ storage buffer before transferring into a tube for activity measurement in the γ-counter. The measured activity of nuclei and cytoplasm/cell membrane fractions was defined as 100% of the cellular uptake. Nuclear localization was expressed as percentage of total cellular uptake. The collected fractions were stained with 0.4% trypan blue solution and analyzed using a microscope in order to confirm that the nuclei were properly separated from other cell fragments.

Figures 6A, 6B:
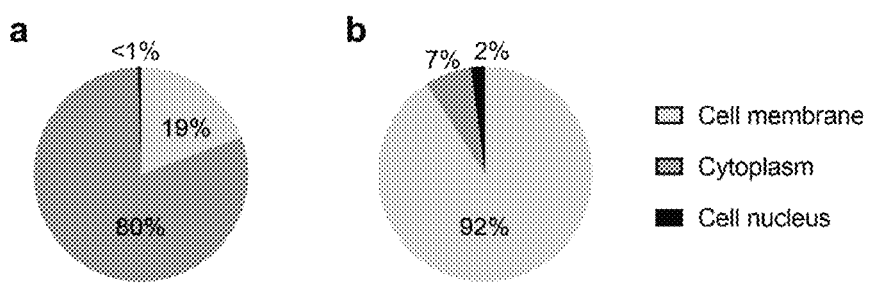
FIGS. 6A and 6B show graphs representing cell uptake and localization studies of the radiopeptides.

The nuclear uptake of [$^{177}$Lu]Lu-DOTATOC and [$^{177}$Lu]Lu-DOTA-LM3 was <1% and ~2% of total cellular uptake. Combining these results with the uptake and internalization data presented (see FIG. 5), the cellular distribution of the single radiopeptides was calculated and presented in pie graphs (see FIG. 6). The internalized fraction of [$^{177}$Lu]Lu-DOTA-LM3 was ~9% of total uptake which was much lower than the internalized fraction of radiolabeled DOTA-TOC (~81% of total uptake). The fraction localized in the nucleus was below 2% (see FIG. 6).

E. Cell Viability Assay

Cell viability studies were performed using AR42J tumor cells to assess potentially different effects of $^{161}$Tb- and $^{177}$Lu-labeled DOTATOC and DOTA-LM3.

A total of 7500 AR42J tumor cells were seeded in 200 µL cell culture medium with supplements in PLL-coated 96-well plates. After incubation overnight to allow cell adhesion, the medium was removed and the cells were incubated with DOTATOC or DOTA-LM3 diluted in assay medium and radiolabeled with either terbium-161 or lutetium-177 at a molar activity of 100 MBq/nmol. The applied activity concentrations per well ranged from 0.001 MBq/mL to 40 MBq/mL (0.01-400 pmol/mL). After an incubation period of 2 h at 37° C., the cells were washed once with PBS followed by addition of fresh cell culture medium with supplements. The tumor cells were allowed to grow for 6 d at 37° C. without changing cell culture medium and the cell viability analyzed as previously described using a 3-(4,5-dimethylthiazol-2-yl)-2,5-diphenyltetrazolium bromide (MTT) assay [51]. After incubation of the cells with the MTT reagent for 2 h, the formed formazan crystals were dissolved in dimethyl sulfoxide. The absorption was measured at 560 nm with a microplate reader (560 nm, Victor™ X3, Perkin Elmer, Waltham, MA, U.S.A.). The absorbance measured for untreated control cells was defined as 100% tumor cell viability. The viability of treated tumor cells (n=12 per concentration) was expressed as percentage of the absorbance of control cells. The cell viability was plotted against the concentration of applied activity (transformed in logarithmic scale) and fitted with a dose-response curve. The cell viability inhibition was calculated as the activity concentration which was necessary to reduce AR42J tumor cell viability to 50% of untreated control cells ($EC_{50}$). $EC_{50}$ values were determined in at least four independent experiments.

Figure 7A:
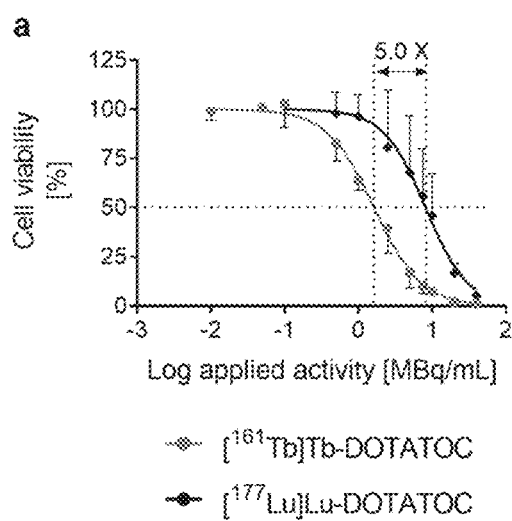
FIGS. 7A and 7B show graphs representing the AR42J tumor cell viability assay (MTT)
Figure 7B:
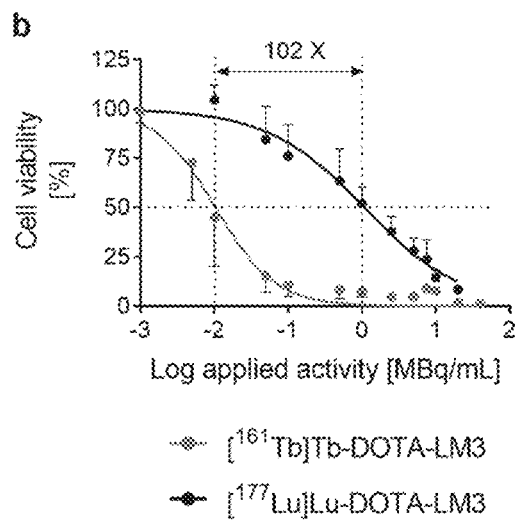

Reduction of AR42J cell viability to less than 10% as compared to the viability of untreated control cells (set as 100%) was achieved at variable activity concentrations dependent on the employed somatostatin analogue and radionuclide, respectively. It was observed that in all cases the $^{161}$Tb-labeled somatostatin analogue was more potent than the $^{177}$Lu-labeled counterpart (see FIG. 7). [$^{161}$Tb]Tb-DOTATOC was ~5-fold more potent than [$^{177}$Lu]Lu-DOTATOC. [$^{161}$Tb]Tb-DOTA-LM3 was, however, 102-fold more potent than [$^{177}$Lu]Lu-DOTA-LM3.

Comparison of the $EC_{50}$ of each $^{161}$Tb-labeled somatostatin analogue revealed a 157-fold higher potency for [$^{161}$Tb]Tb-DOTA-LM3 than for [$^{161}$Tb]Tb-DOTATOC (Table 2). The situation was different for [$^{177}$Lu]Lu-DOTA-LM3 which was 7.7-fold more potent than [$^{177}$Lu]Lu-DOTATOC (Table 2).

TABLE 2

Results of cell viability experiments expressed as half-maximum inhibitory concentration ($EC_{50}$ values).

| Radiopeptide | $EC_{50}$ [MBq/mL] (95% Confidence Interval) | Potency relative to radiolabeled DO-TATOC |
|---|---|---|
| [$^{161}$Tb]Tb-DOTATOC | 1.6 (1.4.1.9) | 1.0 |
| [$^{161}$Tb]Tb-DOTA-LM3 | 0.010 (0.008-0.014) | 157 |
| [$^{177}$Lu]Lu-DOTATOC | 8.2 (6.4-10) | 1.0 |
| [$^{177}$Lu]Lu-DOTA-LM3 | 1.1 (0.8-1.5) | 7.7 |

F. Cell Survival (Clonogenic Assay)

Capability of a single AR42J tumor cell to grow into a colony upon exposure to $^{161}$Tb- and $^{177}$Lu-radiolabeled DOTATOC or DOTA-LM3 was determined by performing clonogenic assays [8].

In order to allow proper formation of colonies, 300 μL Matrigel (Growth Factor Reduced Basement Membrane Matrix, Corning Inc., New York, U.S.A; 2 mg/mL) diluted in RPMI cell medium without additives were added to each well of PPL-coated 6-well plates. AR42J tumor cells were seeded on the solidified Matrigel at a density of 2000 cells per well in 2 mL cell culture medium with supplements and incubated overnight. The next day, the medium was removed and the cells were incubated with $^{161}$Tb- and $^{177}$Lu-radiolabeled somatostatin analogues (30 MBq/nmol) at activity concentrations of 0.01 MBq/mL to 0.5 MBq/mL (0.3-15 pmol/mL) for 2 h at 37° C. and 5% $CO_2$. The same procedure was applied to untreated control cells. After incubation, the supernatant was discarded and the tumor cells were washed with PBS before fresh cell culture medium was added. After two weeks incubation time at 37° C. and 5% $CO_2$, the culture medium was removed and the wells were washed once with PBS. The colonies were stained using crystal violet solution (0.5% crystal violet, 6% glutaraldehyde in water, 800 μL). The number of colonies (>0.1 mm) was determined visually using a grid of 0.5 cm×0.5 cm in five selected squares under the microscope. The plating efficiency (PE) and survived fraction (SF) were calculated according to the following formulas: PE=([number of colonies formed (untreated)]/[number of cells seeded])*100; SF=([number of colonies formed after treatment]/[number of cells seeded*PE])*100 [52].

The SF upon exposure to various radioactivity concentrations of the radioligands was determined in at least three independent experiments using triplicates in each experiment. The data were analyzed with a two-way ANOVA with Sidak's multiple comparison post-tests. A p value <0.05 was considered statistically significant.

Figure 8A:
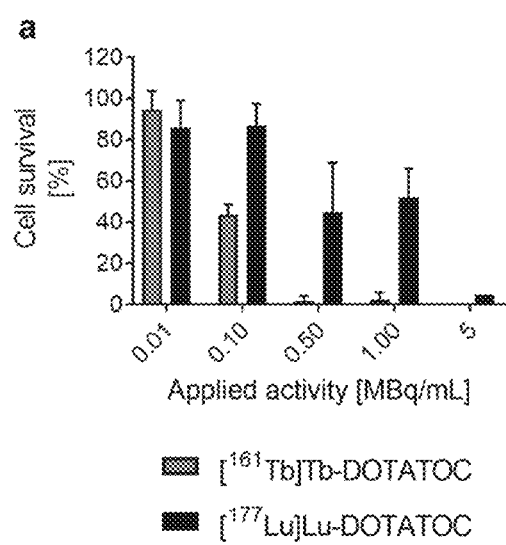
FIGS. 8A and 8B show graphs representing the AR42J tumor cell survival (clonogenic assay)
Figure 8B:
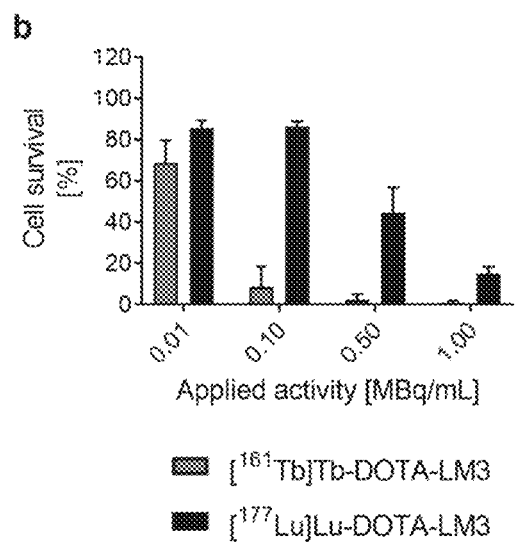

Colony forming assays confirmed that the $^{161}$Tb-labeled peptides were more effective to reduce cell survival than the respective $^{177}$Lu-labeled counterparts (see FIG. 8). Compared to untreated control cells, less than 3% of cells treated with 0.50 MBq/mL [$^{161}$Tb]Tb-DOTATOC survived. To have a similar effect of [$^{177}$Lu]Lu-DOTATOC, a 10-fold higher activity concentration (5 MBq/mL) had to be applied (n=1). [$^{161}$Tb]Tb-DOTA-LM3 reduced the cell survival to <5% at the activity concentration of 0.1 MBq/mL, while [$^{177}$Lu]Lu-DOTA-LM3 applied at a 10-fold higher concentration (1 MBq/mL) reduced the survival to only ~15%.

G. Evaluation of DNA Damage

Experiments were performed with AR42J tumor cells treated with [$^{161}$Tb]Tb-DOTATOC and [$^{177}$Lu]Lu-DOTATOC or [$^{161}$Tb]Tb DOTA-LM3 and [$^{177}$Lu]Lu-DOTA-LM3 to investigate the number of induced double strand breaks (DSBs) in each case.

The number of DNA DSBs was assessed by immunostaining of γ-H2AX in AR42J cells treated with either 2.5 MBq/mL or 10 MBq/mL of each radiopeptide. The cells seeded (5×10$^6$ cells/Petri dish) and let grown overnight. The following day, the medium was removed and the cells were treated with the radiopeptides diluted in assay medium for 2 h. The supernatant was removed and the AR42J tumor cells washed with PBS prior to the addition of fresh culture medium. After 24 h of incubation, cells were washed with PBS and detached by scraping using 1.5 mL PBS, and centrifuged in 1.5-mL Eppendorf tubes. The cell pellets were fixed by addition of 1 mL 4% neutral buffered formalin for 24 h at RT followed by exchanging it with PBS. After paraffin embedding, sections of 4 μm thickness were prepared. In brief, antigen retrieval was performed after deparaffination using a solution containing EDTA (pH 9) at 98° C. for 20 min and followed by incubation with REAL Antibody Diluent (Agilent) for 30 min at RT and hydrogen peroxide (Agilent) for 10 min at RT. The sections were incubated with the primary antibody (Cell signaling rabbit monoclonal antibody (Ser139); dilution 1:200) for 1 h at RT. Envision horseradish peroxidase rabbit (Agilent Technologies, Inc) detection system was used with DAB substrate buffer (Agilent). Immunostained sections were scanned using a digital slide scanner (NanoZoomer-XR C12000; Hamamatsu, Japan) and the total of positive and negative cells quantified with the pathology image analysis software VIS (Visiopharm Integrator System, Version 208 2019.02.2.6239, Visiopharm, Hoersholm, Denmark). First, the decision forest classification method was used to outline the tissue cell pellets as regions of interest (ROIs). Subsequently, the cell classification method was used for the detection of cell nuclei within each ROI and classify them as positive (brown) and negative (blue). Separation of the nucleus type was done by training the software with the predetermined options "Standard positive nuclei" and "Standard negative nuclei". The results were expressed as total positive cells and total negative cells. Data were analyzed with a one-way ANOVA with Dunnet's multiple comparison post-tests. A p value <0.05 was considered statistically significant.

Figure 9A:
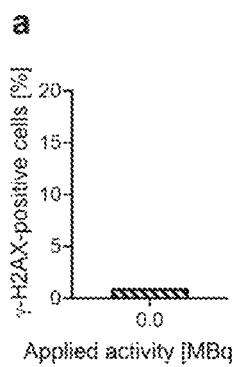
FIGS. 9A-9C show quantification of γ-H2AX-positive AR42J tumor cells, representative for DNA DSBs after cell exposure to the radiopeptides (2.5 MBq and 10 MBq)
Figure 9B:
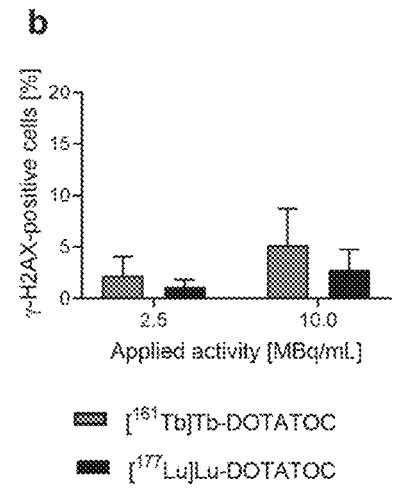
Figure 9C:
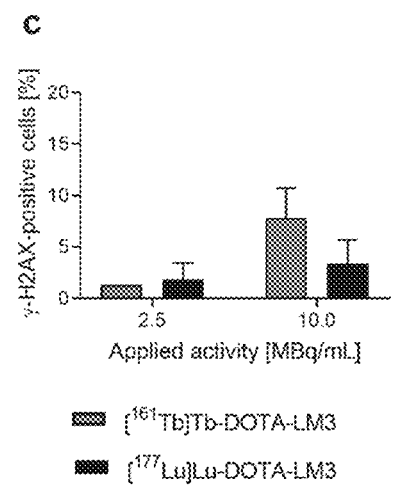

At high activity concentration (10 MBq/mL) an increased number of γ-H2AX-positive foci was determined in all $^{161}$Tb-treated samples as compared to controls, but without reaching a significance level (p<0.05). $^{177}$Lu-labeled somatostatin analogues led to only modest increase of γ-H2AX-positive foci, which was only obvious at high activity concentrations (p>0.05). The results are presented in FIG. 9.

III. In Vivo Studies

In vivo studies were performed to evaluate the tissue distribution of the radiopeptides and optimize the molar amount of injected peptide. Moreover, the therapeutic effect of the radiopeptides and early side effects were assessed.

All applicable international, national, and/or institutional guidelines for the care and use of animals were followed. In particular, all animal experiments were carried out according to the guidelines of Swiss Regulations for Animal Welfare. The preclinical studies were ethically approved by the Cantonal Committee of Animal Experimentation and permitted by the responsible cantonal authorities (license No 75721 and 79692). Five-week-old female, athymic nude mice (CD-1 Foxn-1/nu) were obtained from Charles River Laboratories (Sulzfeld, Germany). Mice were subcutaneously inoculated with AR42J tumor cells ($5×10^6$ cells in 100 μL PBS) for SPECT/CT imaging, biodistribution and therapy studies. The SPECT/CT and biodistribution studies were performed 10-14 days after tumor cell inoculation when the tumor size reached a volume of ~250 mm$^3$.

A. Dual-Isotope SPECT/CT Imaging Studies

The purpose was to demonstrate that the $^{161}$Tb- and $^{177}$Lu-labeled somatostatin counterparts have the same in vivo distribution and that the tumor uptake is SSTR-specific. A second objective was to compare the tissue distribution of the three somatostatin analogues.

Dual-isotope SPECT/CT scans were performed with a dedicated small-animal SPECT/CT scanner (NanoSPECT/CT, Mediso Medical Imaging Systems, Budapest, Hungary; Supplementary Material) as previously reported [44]. The scans were acquired using Nucline software (version 1.02, Mediso Ltd., Budapest, Hungary). Simultaneous acquisition of counts stemming from terbium-161 and lutetium-177, respectively, was performed by the selection of distinct energy windows for the two radionuclides. The two energy windows chosen for terbium-161 were set at 47.7 keV±10%, which enabled the detection of X-rays and γ-rays (46.0 keV, 48.9 keV and 52.0 keV), and at 74.6 keV±10%, enabling the detection of the γ-rays at 74.6 keV. For lutetium-177, the windows were set at 208.4±10% and 112.9 keV±10% to detect the γ-rays at 208.4 keV and 112.9 keV, respectively. SPECT data were reconstructed iteratively using HiSPECT software (version 1.4.3049, Scivis GmbH, Gottingen, Germany). The CT was reconstructed in real time using a cone-beam filtered backprojection. The fused datasets of SPECT and CT scans were analyzed using the VivoQuant postprocessing software (version 3.5, inviCRO Imaging Services and Software, Boston, USA). A Gauss post-reconstruction filter (FWHM=1.0 mm) was applied.

Mice were i.v. injected with a mixture of [$^{161}$Tb]Tb-DOTATOC (~15 MBq, 0.5 nmol/mouse) and [$^{177}$Lu]Lu-DOTATOC (~15 MBq, 0.5 nmol/mouse) or a mixture of [$^{161}$Tb]Tb-DOTA-LM3 and [$^{177}$Lu]Lu-DOTA-LM3 in PBS (pH 7.4) containing 0.05% BSA and ascorbic acid (~300 μg/30 MBq). Blocking studies were performed under the same experimental conditions, however, in this case, an excess (20 nmol/mouse) of unlabeled DOTATOC or DOTA-LM3 was added to the injection solution. SPECT/CT scans were acquired 2 h, 4 h and 24 h after injection of the radiopeptides using the dual-isotope SPECT acquisition protocol with a frame time of 60 sec resulting in a scan time of 45 min. During the in vivo scans, mice were anesthetized by inhalation of a mixture of isoflurane and oxygen.

Figure 10A:
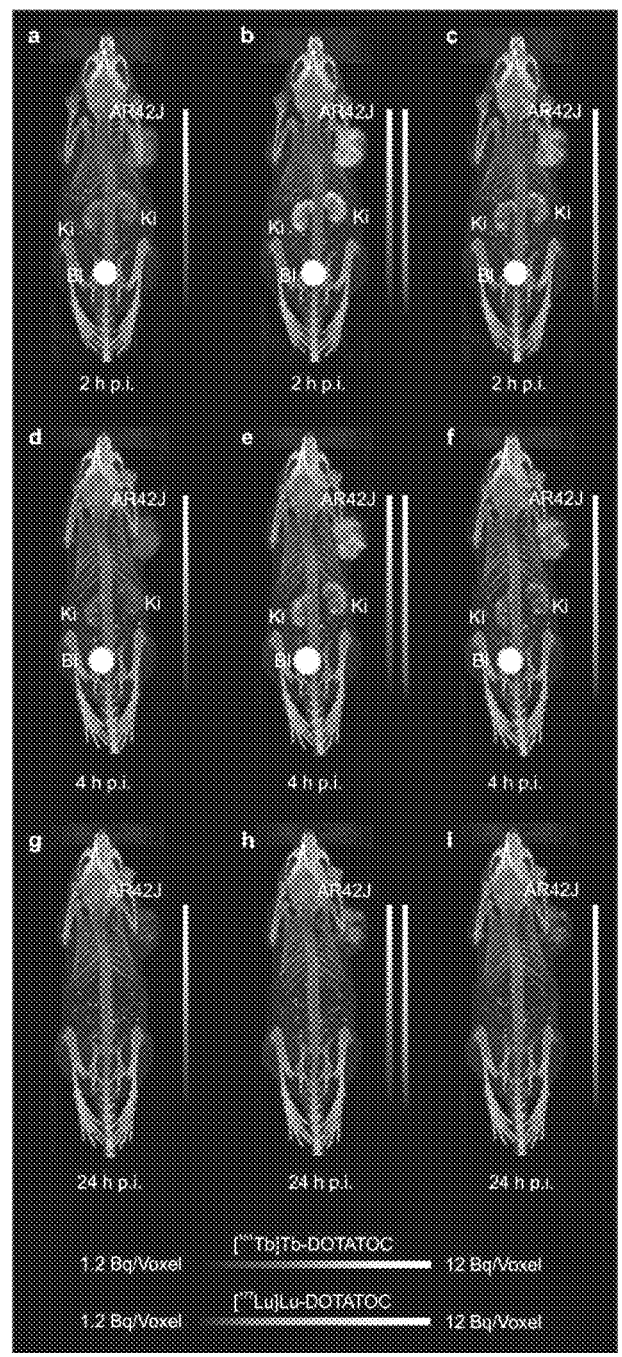
FIG. 10A shows dual-isotope SPECT/CT images of AR42J tumor-bearing mice shown as maximum intensity projections (MIPs) 2 h, 4 h and 24 h after injection of [$^{161}$Tb]Tb-DOTATOC (15 MBq, 0.5 nmol/mouse) and [$^{177}$Lu]Lu-DOTATOC (15 MBq, 0.5 nmol/mouse). (a/b/c) Scans acquired 2 h p.i. of the radiopeptides; (d/e/f) Scans acquired 4 h p.i. of the radiopeptides and (g/h/i) Scans acquired 24 h p.i. of the radiopeptides. (a/d/g) Reconstructions based on the X-rays and γ-lines of terbium-161; (b/e/h) Reconstructions based on the X-rays and γ-lines of terbium-161 and the γ-lines of lutetium-177; (c/f/i) Reconstructions based on the γ-lines of lutetium-177. AR42J=SSTR-positive tumor xenograft; Ki=kidney; Bl=urinary bladder.

The SPECT/CT images of AR42J tumor-bearing mice demonstrated equal in vivo distribution of simultaneously injected [$^{161}$Tb]Tb-DOTATOC and [$^{177}$Lu]Lu-DOTATOC (see FIG. 10). The same observation was made for [$^{161}$Tb]Tb-DOTA-LM3 and [$^{177}$Lu]Lu-DOTA-LM3 (see FIG. 11) [44].

The SPECT/CT images showed activity accumulation in the AR42J xenografts, which was higher for the [$^{161}$Tb]Tb-DOTA-LM3 and [$^{177}$Lu]Lu-DOTA-LM3 than for the [$^{161}$Tb]Tb-DOTATOC and [$^{177}$Lu]Lu-DOTATOC at all investigated time points. The activity was efficiently cleared through the kidneys over time and almost entirely excreted after 24 h. Due to the favorable uptake of radiolabeled DOTA-LM3 in the tumor tissue, the tumor-to-kidney ratio was higher as compared to the ratio obtained after injection of radiolabelled DOTATOC [44].

Figure 10B:
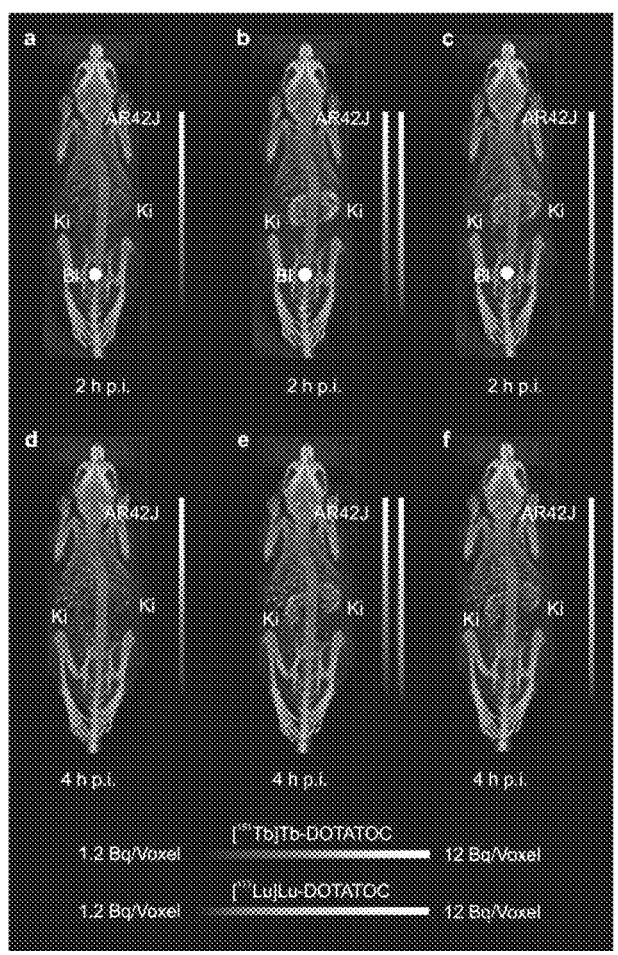
FIG. 10B shows dual-isotope SPECT/CT images of blocking studies carried out in AR42J tumor-bearing mice. Images are shown as maximum intensity projections (MIPs) 2 h and 4 h p.i. of [$^{161}$Tb]Tb-DOTATOC (15 MBq, 0.5 nmol/mouse) and [$^{177}$Lu]Lu-DOTATOC (15 MBq, 0.5 nmol/mouse) and excess unlabeled DOTATOC (20 nmol/mouse). (A/B/C) Scans acquired 2 h p.i. of the radiopeptides; (D/E/F) Scans acquired 4 h p.i. of the radiopeptides. (A/D) Reconstructions based on the x-rays and γ-lines of terbium-161; (B/E) Reconstructions based on the X-rays and γ-lines of terbium-161 and the γ-lines of lutetium-177; (C/F) Reconstructions based on the γ-lines of lutetium-177. AR42J=SSTR2-positive tumor xenograft; Ki=kidney; Bl=urinary bladder.
Figure 11A:
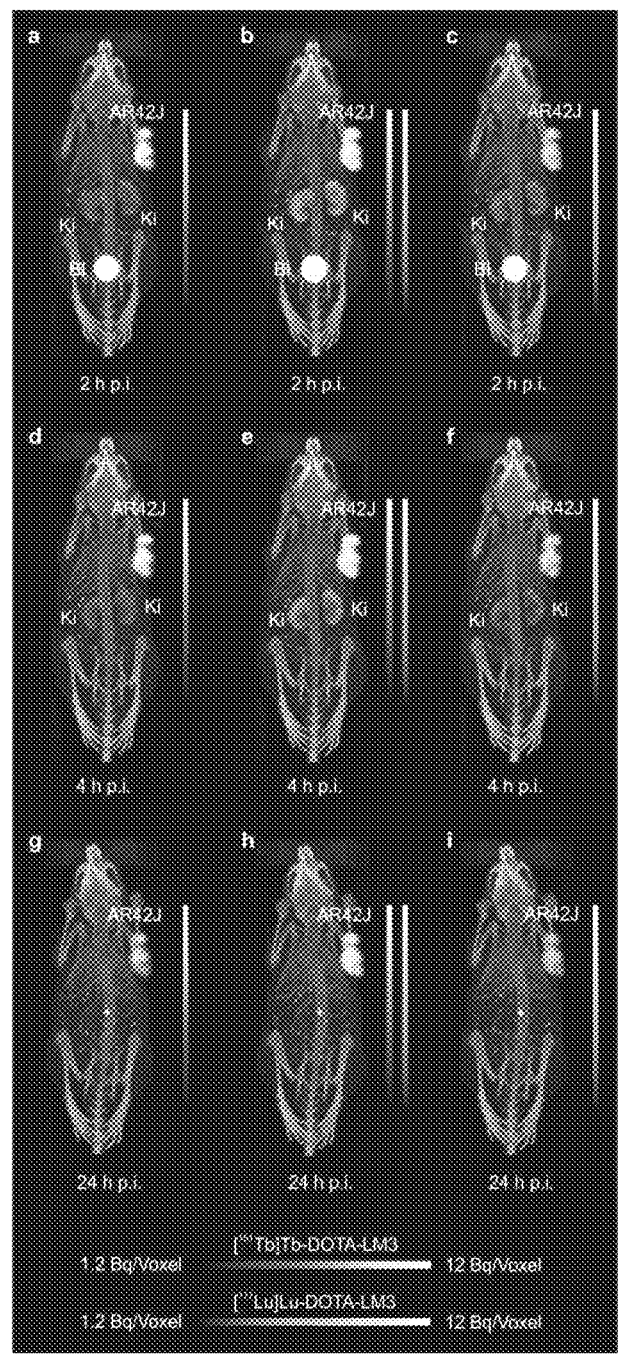
FIG. 11A shows dual-isotope SPECT/CT images of AR42J tumor-bearing mice shown as maximum intensity projections (MIPs) 2 h, 4 h and 24 h after injection of [$^{161}$Tb]Tb-DOTA-LM3 (15 MBq, 0.5 nmol/mouse) and [$^{177}$Lu]Lu-DOTA-LM3 (15 MBq, 0.5 nmol/mouse). (a/b/c) Scans acquired 2 h p.i. of the radiopeptides; (d/e/f) Scans acquired 4 h p.i. of the radiopeptides and (g/h/i) Scans acquired 24 h p.i. of the radiopeptides. (a/d/g) Reconstructions based on the X-rays and γ-lines of terbium-161; (b/e/h) Reconstructions based on the X-rays and γ-lines of terbium-161 and the γ-lines of lutetium-177; (c/f/i) Reconstructions based on the γ-lines of lutetium-177. AR42J=SSTR-positive tumor xenograft; Ki=kidney; Bl=urinary bladder.
Figure 11B:
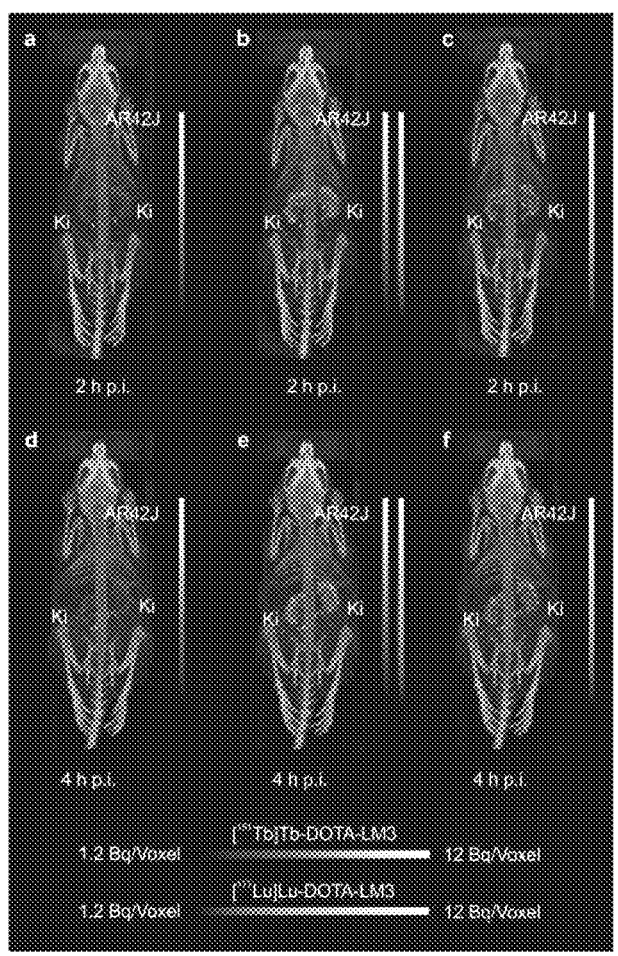
FIG. 11B shows dual-isotope SPECT/CT images of blocking studies carried out in AR42J tumor-bearing mice. Images are shown as maximum intensity projections (MIPs) 2 h and 4 h p.i. of [$^{161}$Tb]Tb-DOTA-LM3 (15 MBq, 0.5 nmol) and [$^{177}$Lu]Lu-DOTA-LM3 (15 MBq, 0.5 nmol) and excess unlabeled DOTA-LM3 (20 nmol/mouse). (A/B/C) Scans acquired 2 h p.i. of the radiopeptides; (D/E/F) Scans acquired 4 h p.i. of the radiopeptides. (A/D) Reconstructions based on the x-rays and γ-lines of terbium-161; (B/E) Reconstructions based on the X-rays and γ-lines of terbium-161 and the γ-lines of lutetium-177; (C/F) Reconstructions based on the γ-lines of lutetium-177. AR42J=SSTR2-positive tumor xenograft; Ki=kidney; Bl=urinary bladder.
Figure 12A:
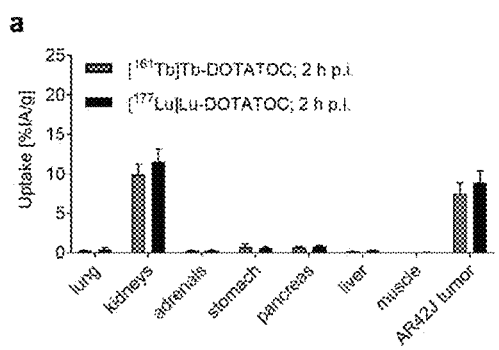
FIGS. 12A-12D show biodistribution data obtained in AR42J tumor-bearing mice.
Figure 12B:
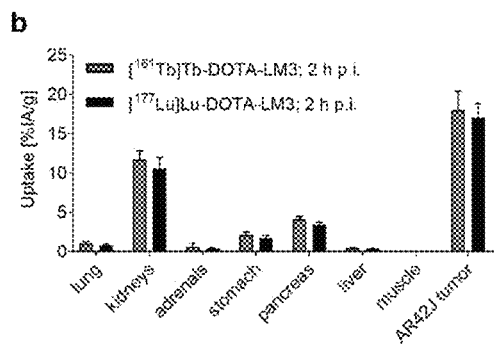
Figure 12C:
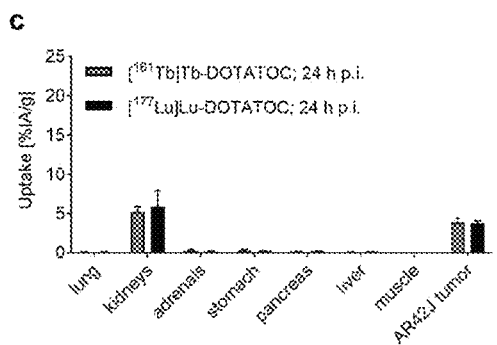
Figure 12D:
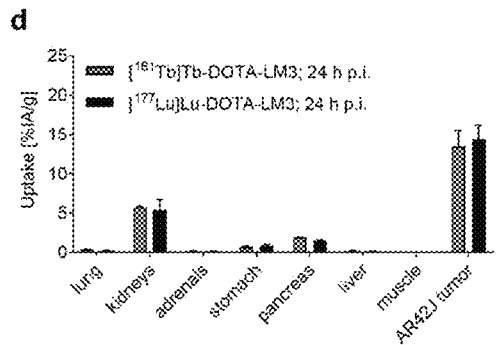
Figure 15A:
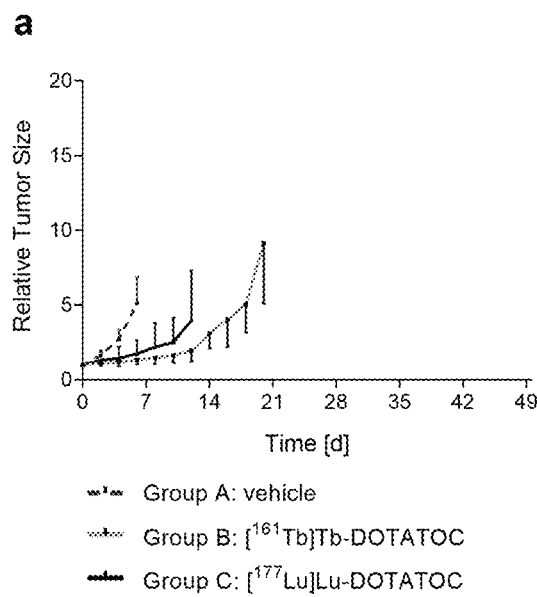
FIGS. 15A-15D show therapy study performed with $^{161}$Tb- and $^{177}$Lu-labeled DOTATOC and DOTA-LM3 in AR42J tumor-bearing mice.
Figure 15B:
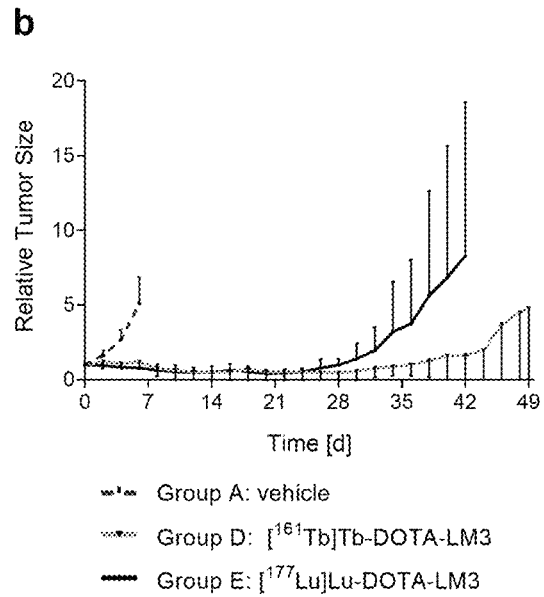
Figure 15C:
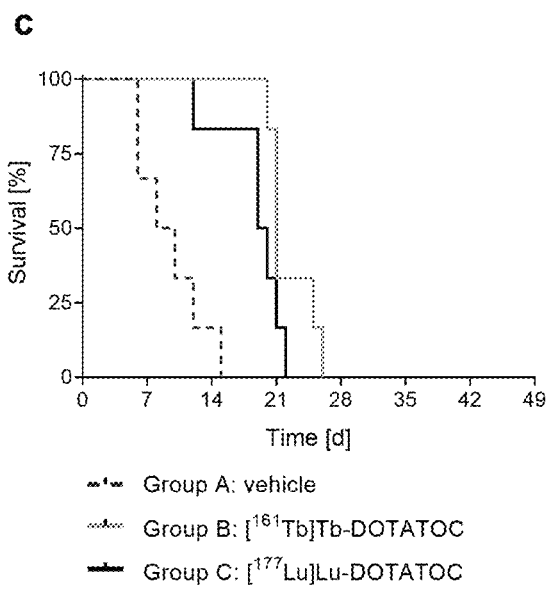
Figure 15D:
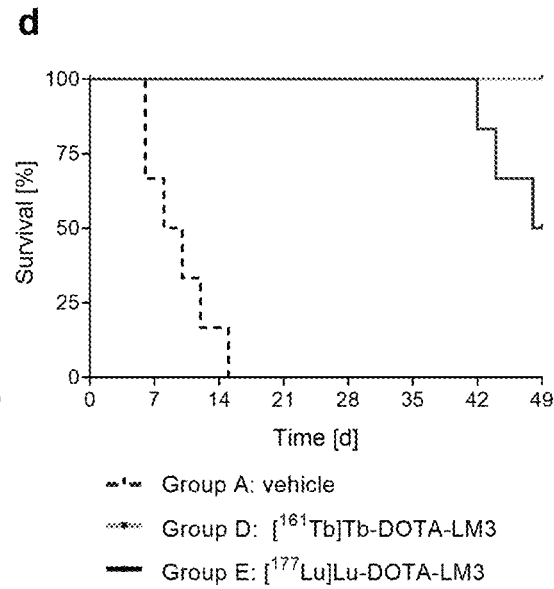

Experiments performed by co-injection of excess of the respective unlabeled peptide resulted in blockade of radiopeptide accumulation in AR42J tumors, proving that the uptake was SSTR-specific are shown in FIGS. 10B and 11B.

B. Biodistribution Studies: Comparison of $^{161}$Tb- and $^{177}$Lu-Labeled Peptides Biodistribution studies were performed to assess quantitatively the tissue distribution of $^{161}$Tb-labeled peptides and compare them with the $^{177}$Lu-labeled counterparts.

Biodistribution studies were performed after intravenous injection of the mice with [$^{161}$Tb]Tb-DOTATOC or [$^{177}$Lu]Lu-DOTATOC (5 MBq; 1 nmol in 100 μL per mouse) diluted in PBS (pH 7.4) containing 0.05% BSA. [$^{161}$Tb]Tb-DOTA-LM3 or [$^{177}$Lu]Lu-DOTA-LM3 were used under the same conditions. The mice were sacrificed at 2 h and 24 h post injection (p.i.). Selected tissues and organs were collected, weighed, and the accumulated activity was counted in a γ-counter. The decay-corrected data were listed as the percentage of the injected activity per gram of tissue mass (% IA/g). The data were analyzed for significance using a two-way ANOVA with Tukey's multiple comparison post-tests. A p-value of <0.05 was considered statistically significant.

The biodistribution of $^{161}$Tb-labeled DOTATOC was comparable to that of $^{177}$Lu-labeled DOTATOC, demonstrated by similar activity accumulation in tissues and organs at both investigated at 2 h and 24 h, respectively (p>0.05). Equal tissue distribution of $^{161}$Tb- and $^{177}$Lu-labeled counterparts was also observed when using DOTA-LM3 (see FIG. 12, Tables A1/A2). These findings confirmed that terbium-161 and lutetium-177 are interchangeable without alteration of the radiopeptide's pharmacokinetic properties as already demonstrated with $^{161}$Tb- and $^{177}$Lu-labeled folate conjugates and PSMA ligands [34, 36].

TABLE A1

Biodistribution data obtained in AR42J tumor-bearing mice at 2 h and 24 h after injection of [$^{161}$Tb]Tb-DOTATOC and [$^{177}$Lu]Lu-DOTATOC, respectively. Decay-corrected data are shown as [% IA/g] values, representing the average ± SD (n = 3-4).

|  | [$^{161}$Tb]Tb-DOTATOC | | [$^{177}$Lu]Lu-DOTATOC | |
| --- | --- | --- | --- | --- |
|  | 2 h p.i. | 24 h p.i. | 2 h p.i. | 24 h p.i. |
| Blood | ≤0.10 | ≤0.10 | ≤0.10 | ≤0.10 |
| Heart | ≤0.10 | ≤0.10 | ≤0.10 | ≤0.10 |
| Lung | 0.27 ± 0.03 | 0.11 ± 0.01 | 0.37 ± 0.06 | 0.12 ± 0.03 |
| Spleen | 0.11 ± 0.02 | ≤0.10 | 0.15 ± 0.03 | ≤0.10 |
| Kidneys | 9.9 ± 1.3 | 5.2 ± 0.6 | 11 ± 1 | 5.9 ± 2.1 |
| Adrenals | 0.25 ± 0.06 | 0.23 ± 0.20 | 0.28 ± 0.08 | 0.18 ± 0.08 |
| Stomach | 0.74 ± 0.38 | 0.29 ± 0.11 | 0.65 ± 0.11 | 0.24 ± 0.04 |
| Pancreas | 0.71 ± 0.07 | 0.18 ± 0.01 | 0.80 ± 0.13 | 0.21 ± 0.04 |
| Intestines | 0.21 ± 0.13 | ≤0.10 | 0.20 ± 0.05 | ≤0.10 |
| Liver | 0.17 ± 0.01 | ≤0.10 | 0.26 ± 0.07 | 0.13 ± 0.02 |
| Muscle | ≤0.10 | ≤0.10 | ≤0.10 | ≤0.10 |
| Femur | ≤0.10 | ≤0.10 | ≤0.10 | ≤0.10 |
| AR42J Tumor | 8.2 ± 0.2 | 3.8 ± 0.6 | 8.9 ± 1.5 | 3.8 ± 0.3 |
| Tumor-to-blood | 260 ± 13 | 433 ± 71 | 146 ± 16 | 456 ± 118 |
| Tumor-to-liver | 49 ± 1 | 41 ± 7 | 36 ± 7 | 31 ± 6 |
| Tumor-to-kidney | 0.84 ± 0.12 | 0.73 ± 0.10 | 0.73 ± 0.07 | 0.72 ± 0.34 |

TABLE A2

Biodistribution data obtained in AR42J tumor-bearing mice at 2 h and 24 h after injection of [$^{161}$Tb]Tb-DOTA-LM3 and [$^{177}$Lu]Lu-DOTA-LM3, respectively. Decay-corrected data are shown as [% IA/g] values, representing the average ± SD (n = 3-4).

|  | [$^{161}$Tb]Tb-DOTA-LM3 | | [$^{177}$Lu]Lu-DOTA-LM3 | |
| --- | --- | --- | --- | --- |
|  | 2 h p.i. | 24 h p.i. | 2 h p.i. | 24 h p.i. |
| Blood | ≤0.10 | ≤0.10 | ≤0.10 | ≤0.10 |
| Heart | 0.11 ± 0.02 | ≤0.10 | ≤0.10 | ≤0.10 |
| Lung | 1.0 ± 0.2 | 0.36 ± 0.06 | 0.83 ± 0.14 | 0.28 ± 0.02 |
| Spleen | 0.27 ± 0.06 | 0.13 ± 0.03 | 0.23 ± 0.06 | ≤0.10 |
| Kidneys | 12 ± 2 | 5.8 ± 0.1 | 11 ± 1 | 5.4 ± 1.3 |
| Adrenals | 0.44 ± 0.06 | 0.18 ± 0.05 | 0.37 ± 0.10 | 0.17 ± 0.04 |
| Stomach | 2.2 ± 0.3 | 0.69 ± 0.14 | 1.7 ± 0.4 | 0.86 ± 0.13 |
| Pancreas | 4.2 ± 0.3 | 1.9 ± 0.1 | 3.4 ± 0.3 | 1.5 ± 0.1 |
| Intestines | 0.43 ± 0.23 | 0.11 ± 0.01 | 0.31 ± 0.14 | 0.14 ± 0.03 |
| Liver | 0.45 ± 0.05 | 0.22 ± 0.05 | 0.35 ± 0.08 | 0.15 ± 0.03 |
| Muscle | ≤0.10 | ≤0.10 | ≤0.10 | ≤0.10 |
| Femur | 0.20 ± 0.05 | 0.11 ± 0.02 | 0.17 ± 0.04 | ≤0.10 |
| AR42J Tumor | 18 ± 2 | 14 ± 2 | 17 ± 2 | 14 ± 2 |
| Tumor-to-blood | 200 ± 38 | >1000 | 270 ± 92 | >1000 |
| Tumor-to-liver | 38 ± 7 | 63 ± 18 | 51 ± 7 | 95 ± 16 |
| Tumor-to-kidney | 1.4 ± 0.2 | 2.4 ± 0.5 | 1.9 ± 0.2 | 2.9 ± 0.9 |

C. Biodistribution Studies: Assessment of the Optimum Injected Molar Amount

The aim was to assess the impact of the injected amount of peptide on the biodistribution of $^{161}$Tb- and $^{177}$Lu-labeled DOTATOC and DOTA-LM3.

The mice (n=3 per group) were intravenously injected with the radiolabeled DOTATOC or DOTA-LM3 (3 MBq, 0.04 nmol/mouse; 5 MBq, 0.2 nmol/mouse; 5 MBq, 1.0 nmol/mouse) in 100 µL PBS (pH 7.4) containing 0.05% BSA. The mice were sacrificed at 2 h p.i, selected tissues and organs were collected, weighed, and the accumulated activity was counted using a γ-counter (Perkin Elmer). The decay-corrected data were listed as % IA/g. The data were analyzed for significance using a two-way ANOVA with Tukey's multiple comparison post-tests. A p-value of <0.05 was considered statistically significant.

In agreement with previous studies [53], the amount of injected peptide had a significant impact on the accumulated activity in different organs and tissues (see FIG. 13, Tables A3/A4).

TABLE A3

Biodistribution data obtained in AR42J tumor-bearing mice at 2 h after injection of [$^{161}$Tb]Tb-DOTATOC or [$^{177}$Lu]Lu-DOTATOC. Decay-corrected data are shown as % IA/g tissue, representing the average ± SD.

|  | [$^{161}$Tb]Tb-DOTATOC 2 h p.i. | | | [$^{177}$Lu]Lu-DOTATOC 2 h p.i. | | |
| --- | --- | --- | --- | --- | --- | --- |
|  | 0.040 nmol | 0.20 nmol | 1.0 nmol* | 0.040 nmol | 0.20 nmol | 1.0 nmol* |
| Blood | ≤0.10 | ≤0.10 | ≤0.10 | ≤0.10 | ≤0.10 | ≤0.10 |
| Heart | ≤0.10 | ≤0.10 | ≤0.10 | ≤0.10 | ≤0.10 | ≤0.10 |
| Lung | 1.2 ± 0.1 | 0.47 ± 0.05 | 0.27 ± 0.03 | 1.1 ± 0.2 | 0.63 ± 0.03 | 0.37 ± 0.06 |
| Spleen | 0.50 ± 0.11 | 0.18 ± 0.02 | 0.11 ± 0.02 | 0.39 ± 0.11 | 0.15 ± 0.02 | 0.15 ± 0.03 |
| Kidneys | 9.0 ± 2.0 | 9.4 ± 0.4 | 9.9 ± 1.3 | 10 ± 2 | 10 ± 3 | 11 ± 1 |
| Adrenals | 0.65 ± 0.08 | 0.43 ± 0.11 | 0.25 ± 0.06 | 0.65 ± 0.10 | 0.51 ± 0.35 | 0.28 ± 0.08 |
| Stomach | 2.9 ± 1.1 | 1.2 ± 0.3 | 0.74 ± 0.38 | 1.7 ± 0.3 | 1.1 ± 0.2 | 0.65 ± 0.11 |
| Pancreas | 2.1 ± 0.5 | 1.5 ± 0.2 | 0.71 ± 0.07 | 1.9 ± 0.2 | 1.7 ± 0.5 | 0.80 ± 0.13 |
| Intestines | 0.52 ± 0.15 | 0.24 ± 0.01 | 0.21 ± 0.13 | 0.33 ± 0.05 | 0.40 ± 0.25 | 0.20 ± 0.05 |
| Liver | 0.22 ± 0.02 | 0.19 ± 0.03 | 0.17 ± 0.01 | 0.18 ± 0.02 | 0.15 ± 0.03 | 0.26 ± 0.07 |
| Muscle | ≤0.10 | ≤0.10 | ≤0.10 | ≤0.10 | ≤0.10 | ≤0.10 |
| Femur | 0.23 ± 0.03 | 0.12 ± 0.03 | ≤0.10 | 0.17 ± 0.05 | 0.10 ± 0.01 | ≤0.10 |
| AR42J Tumor | 16 ± 4 | 14 ± 1 | 8.2 ± 0.2 | 18 ± 3 | 17 ± 4 | 8.9 ± 1.5 |
| Tu-to-blood | 187 ± 12 | 221 ± 56 | 260 ± 13 | 213 ± 41 | 235 ± 60 | 146 ± 16 |
| Tu-to-liver | 73 ± 3 | 76 ± 14 | 49 ± 1 | 100 ± 8 | 118 ± 24 | 36 ± 7 |
| Tu-to-kidney | 1.8 ± 0.2 | 1.5 ± 0.1 | 0.84 ± 0.12 | 1.9 ± 0.3 | 1.9 ± 0.4 | 0.73 ± 0.07 |

TABLE A4

Biodistribution data obtained in AR42J tumor-bearing mice at 2 h after injection of [161Tb]Tb-DOTA-LM3 or [177Lu]Lu-DOTA-LM3. Decay-corrected data are shown as % IA/g tissue, representing the average ± SD.

| | [161Tb]Tb-DOTA-LM3 2 h p.i. | | | [177Lu]Lu-DOTA-LM3 2 h p.i. | | |
|---|---|---|---|---|---|---|
| | 0.040 nmol | 0.20 nmol | 1.0 nmol* | 0.040 nmol | 0.20 nmol | 1.0 nmol* |
| Blood | 0.12 ± 0.02 | ≤0.10 | ≤0.10 | 0.11 ± 0.01 | ≤0.10 | ≤0.10 |
| Heart | 0.34 ± 0.06 | 0.13 ± 0.01 | 0.11 ± 0.02 | 0.24 ± 0.04 | 0.14 ± 0.04 | ≤0.10 |
| Lung | 7.8 ± 0.7 | 2.9 ± 0.7 | 1.0 ± 0.2 | 8.2 ± 0.7 | 2.6 ± 0.4 | 0.83 ± 0.14 |
| Spleen | 1.8 ± 1.0 | 0.41 ± 0.08 | 0.27 ± 0.06 | 2.3 ± 1.9 | 0.41 ± 0.13 | 0.23 ± 0.06 |
| Kidneys | 8.8 ± 1.3 | 9.5 ± 1.0 | 12 ± 2 | 7.8 ± 0.5 | 11 ± 3 | 11 ± 1 |
| Adrenals | 5.9 ± 1.2 | 1.5 ± 0.2 | 0.44 ± 0.06 | 3.6 ± 0.6 | 1.4 ± 0.5 | 0.37 ± 0.10 |
| Stomach | 29 ± 7 | 11 ± 1 | 2.2 ± 0.3 | 21 ± 3.4 | 6.0 ± 0.9 | 1.7 ± 0.4 |
| Pancreas | 53 ± 5 | 17 ± 3 | 4.2 ± 0.3 | 49 ± 2.5 | 14 ± 2 | 3.4 ± 0.3 |
| Intestines | 2.0 ± 0.2 | 0.74 ± 0.11 | 0.43 ± 0.23 | 1.4 ± 0.6 | 0.53 ± 0.10 | 0.31 ± 0.14 |
| Liver | 2.6 ± 0.9 | 0.63 ± 0.24 | 0.45 ± 0.05 | 1.2 ± 0.2 | 0.51 ± 0.16 | 0.35 ± 0.08 |
| Muscle | ≤0.10 | ≤0.10 | ≤0.10 | ≤0.10 | ≤0.10 | ≤0.10 |
| Femur | 1.6 ± 0.5 | 0.53 ± 0.19 | 0.20 ± 0.05 | 0.75 ± 0.12 | 0.36 ± 0.05 | 0.17 ± 0.04 |
| AR42J Tumor | 29 ± 6 | 33 ± 6 | 18 ± 2 | 37 ± 11 | 44 ± 7 | 17 ± 2 |
| Tu-to-blood | 259 ± 22 | 461 ± 29 | 200 ± 38 | 289 ± 45 | 492 ± 102 | 270 ± 92 |
| Tu-to-liver | 13 ± 2 | 53 ± 9 | 38 ± 7 | 29 ± 8 | 90 ± 11 | 51 ± 7 |
| Tu-to-kidney | 3.5 ± 0.3 | 3.4 ± 0.1 | 1.4 ± 0.2 | 4.3 ± 1.2 | 4.3 ± 0.4 | 1.9 ± 0.2 |

The tumor uptake of [161Tb]Tb-/[177Lu]Lu-DOTATOC applied at 0.04 nmol and 0.2 nmol per mouse was similar (~17% IA/g and ~15% IA/g, respectively, p>0.05), but significantly higher than when 1.0 nmol were injected (~8% IA/g; p<0.05). The uptake in the stomach was higher after injection of 0.04 nmol compared to the injection of 0.2 nmol or 1.0 nmol (p<0.05). The uptake in pancreas, adrenals and lungs showed a similar trend, but the difference was not significant among the settings (p>0.05). No difference was observed in the kidney uptake (~10%) and liver uptake (~0.2% IA/g) irrespective of the applied setting. [161Tb]Tb-/[177Lu]Lu-DOTA-LM3 showed equally high tumor uptake at 0.040 nmol and 0.20 nmol injected peptide per mouse (~34% and ~38% IA/g, p>0.05). The uptake was lower at 1.0 nmol (~18% IA/g, p<0.05). The uptake in the pancreas, adrenals, lungs and stomach was significantly higher at 0.040 nmol injected peptide than at 0.2 nmol per mouse and the lowest uptake was observed at an injected peptide amount of 1.0 nmol per mouse (p<0.05). The uptake in the liver was slightly, but not significantly elevated at the lowest molar amount injected (p>0.05). The kidney uptake of [161Tb]Tb/[177Lu]Lu-DOTA-LM3 was in the range of 10% IA/g irrespective of the injected amount of peptide. The results are presented in FIG. 13.

As a result of these findings, the tumor-to-organ ratios varied dependent on the amount of injected radiopeptide (Table 3 and 4). Tumor-to-kidney (tu-to-ki) and tumor-to-liver (tu-to-li) ratios were favorable after injection of low molar amounts of peptide (0.04 nmol or 0.2 nmol) in both cases, for DOTATOC and DOTA-LM3. The tumor-to-pancreas (tu-to-panc), tumor-to-adrenals (tu-to-adr), tumor-to-lungs (tu-to-lung) and tumor-to-stomach (tu-to-sto) ratios were higher after injection of 0.2 nmol or 1.0 nmol of [161Tb]Tb/[177Lu]Lu-DOTATOC. These ratios were, however, more favorable after injection of 1.0 nmol peptide of 161Tb- and 177Lu-labeled DOTA-LM3 than after using 0.2 nmol peptide per mouse. The injection of 0.04 nmol peptide per mouse resulted in the least favorable ratios. Considered that the injection of 0.2 nmol peptide per mouse resulted in the highest tumor uptake and in the majority of the cases favorable tumor-to-background ratios, this molar amount of injected peptide was used for further in vivo studies.

TABLE 3

Effect of the amount of injected radiopeptide on the tumor-to-organs ratios of [161Tb]Tb-/[177Lu]Lu-DOTATOC at 2 h p.i. of the radiopeptide.

| | [161Tb]Tb-DOTATOC | | | [177Lu] Lu-DOTATOC | | |
|---|---|---|---|---|---|---|
| | 0.040 nmol | 0.20 nmol | 1.0 nmol | 0.040 nmol | 0.20 nmol | 1.0 nmol |
| Tu-to-ki | 1.8 ± 0.2 | 1.5 ± 0.1 | 0.84 ± 0.12 | 1.9 ± 0.3 | 1.9 ± 0.4 | 0.72 ± 0.34 |
| Tu-to-li | 74 ± 3 | 76 ± 14 | 49 ± 1 | 100 ± 8 | 118 ± 24 | 31 ± 6 |
| Tu-to-panc | 7.8 ± 0.9 | 9.4 ± 1.3 | 12 ± 1 | 9.7 ± 1.8 | 10 ± 2 | 13 ± 1 |
| Tu-to-adr | 24 ± 1 | 34 ± 7 | 36 ± 10 | 28 ± 2 | 47 ± 29 | 29 ± 3 |
| Tu-to-lung | 13 ± 1 | 30 ± 4 | 33 ± 4 | 17 ± 3 | 27 ± 6 | 25 ± 3 |
| Tu-to-sto | 6 ± 2 | 12 ± 3 | 15 ± 2 | 11 ± 2 | 15 ± 4 | 15 ± 5 |

TABLE 4

Effect of the amount of injected radiopeptide on the tumor-to-organs ratios of [$^{161}$Tb]Tb-/[$^{177}$Lu]Lu-DOTA-M3 at 2 h p.i. of the radiopeptide.

| | [$^{161}$Tb]Tb-DOTA-LM3 | | | [$^{177}$Lu]Lu-DOTA-LM3 | | |
|---|---|---|---|---|---|---|
| | 0.040 nmol | 0.20 nmol | 1.0 nmol | 0.040 nmol | 0.20 nmol | 1.0 nmol |
| Tu-to-ki | 3.5 ± 0.3 | 3.4 ± 0.1 | 1.4 ± 0.2 | 4.3 ± 1.2 | 4.3 ± 0.4 | 1.9 ± 0.2 |
| Tu-to-li | 13 ± 2 | 53 ± 9 | 38 ± 7 | 29 ± 8 | 90 ± 11 | 51 ± 7 |
| Tu-to-panc | 0.59 ± 0.05 | 1.9 ± 0.4 | 4.2 ± 0.4 | 0.77 ± 0.20 | 3.2 ± 0.3 | 4.2 ± 0.8 |
| Tu-to-adr | 5.4 ± 1.0 | 22 ± 5 | 36 ± 16 | 11 ± 4 | 34 ± 9.2 | 36 ± 6 |
| Tu-to-lung | 4.0 ± 0.6 | 12 ± 3 | 16 ± 4 | 4.3 ± 1.2 | 17 ± 2 | 18 ± 1 |
| Tu-to-sto | 1.1 ± 0.2 | 3.0 ± 0.3 | 8.5 ± 1.5 | 1.8 ± 0.6 | 7.4 ± 0.6 | 11 ± 2 |

D. Time-Dependent Biodistribution Studies

Time-dependent biodistribution studies were performed to assess the total uptake of the radiopeptides in the tumor as well as in healthy organs and tissues.

The mice (n=3 per group) were intravenously injected with the radiolabeled DOTATOC or DOTA-LM3 (5 MBq, 0.2 nmol/mouse) in 100 μL PBS (pH 7.4) containing 0.05% BSA. The mice were sacrificed at 0.5 h, 2 h, 4 h, 24 h and 48 h p.i, selected tissues and organs were collected, weighed, and the accumulated activity was counted using a γ-counter (Perkin Elmer). The decay-corrected data were listed as % IA/g. The data were analyzed for significance using a two-way ANOVA with Tukey's multiple comparison post-tests. A p-value of <0.05 was considered statistically significant.

[$^{161}$Tb]Tb-DOTATOC reached the highest tumor uptake (15±2%) already 0.5 h after injection. The activity was retained in the tumor tissue up to 4 h but was cleared over the following hours resulting in 6.4±0.5% IA/g and 3.7±0.7% IA/g after 24 h and 48 h p.i. Significant activity accumulation was observed in the lungs, stomach and pancreas, however, it was cleared efficiently resulting in ≤1% IA/g after 4 h p.i. The clearance from kidneys was slow and still ~10% IA/g at 4 h p.i., ~4-5% IA/g and 2-3% after 24 h and 48 h p.i. (see FIG. 14a; Table A5).

TABLE A5

Biodistribution data obtained in AR42J tumor-bearing mice at 0.5, 2, 4, 24 and 48 h after injection of 0.2 nmol of [$^{161}$Tb]Tb-DOTATOC. Decay-corrected data are shown as % IA/g tissue, representing the average ± SD

| | [$^{161}$Tb]Tb-DOTATOC (0.2 nmol/mouse) | | | | |
|---|---|---|---|---|---|
| | 0.5 h | 2 h | 4 h | 24 h | 48 h |
| Blood | 1.0 ± 0.1 | ≤0.10 | ≤0.10 | ≤0.10 | ≤0.10 |
| Heart | 0.45 ± 0.02 | ≤0.10 | ≤0.10 | ≤0.10 | ≤0.10 |
| Lung | 1.5 ± 0.1 | 0.47 ± 0.05 | 0.34 ± 0.06 | 0.15 ± 0.04 | 0.11 ± 0.02 |
| Spleen | 0.40 ± 0.09 | 0.18 ± 0.02 | 0.15 ± 0.00 | ≤0.10 | ≤0.10 |
| Kidneys | 11 ± 1 | 9.4 ± 0.4 | 11 ± 1 | 4.4 ± 0.9 | 1.8 ± 0.3 |
| Adrenals | 0.77 ± 0.18 | 0.43 ± 0.11 | 0.43 ± 0.03 | 0.16 ± 0.02 | 0.22 ± 0.07 |
| Stomach | 2.5 ± 0.3 | 1.2 ± 0.3 | 0.88 ± 0.09 | 0.78 ± 0.62 | 0.29 ± 0.05 |
| Pancreas | 3.8 ± 0.2 | 1.5 0.2 | 1.1 ± 0.1 | 0.40 ± 0.02 | 0.23 ± 0.02 |
| Intestines | 0.47 ± 0.04 | 0.24 ± 0.01 | 0.20 ± 0.03 | 0.22 ± 0.25 | ≤0.10 |
| Liver | 0.41 ± 0.02 | 0.19 ± 0.03 | 0.15 ± 0.01 | ≤0.10 | ≤0.10 |
| Muscle | 0.24 ± 0.02 | ≤0.10 | ≤0.10 | ≤0.10 | ≤0.10 |
| Femur | 0.42 ± 0.04 | 0.12 ± 0.03 | ≤0.10 | ≤0.10 | ≤0.10 |
| AR42J Tumor | 15 ± 1 | 14 ± 1 | 14 ± 1 | 6.3 ± 0.6 | 3.7 ± 0.7 |
| Tumor-to-blood | 15 ± 2 | 221 ± 56 | 329 ± 17 | 490 ± 37 | 622 ± 14 |
| Tumor-to-liver | 37 ± 2 | 76 ± 14 | 89 ± 3 | 67 ± 6 | 53 ± 3 |
| Tumor-to-kidney | 1.4 ± 0.2 | 1.5 ± 0.1 | 1.3 ± 0.1 | 1.5 ± 0.2 | 2.1 ± 0.3 |

Based on the fact that the tissue distribution remains the same irrespective of whether a somatostatin analogue is labeled with terbium-161 or lutetium-177, these results can be extrapolated also to the $^{177}$Lu-labeled counterparts [44]. The tumor uptake of [$^{161}$Tb]Tb-DOTA-LM3 was also fast resulting in 35±7% IA/g at 4 h p.i. After 48 h the activity in the tumor (21±4% IA/g) was still high. In other organs such as the lungs, stomach and pancreas, activity retention was seen over the first 4 h but effectively cleared afterwards. The accumulated activity of [$^{161}$Tb]Tb-DOTA-LM3 in tumor, pancreas and stomach was significantly higher than in the case of [$^{161}$Tb]Tb-DOTATOC ($p<0.05$) at all investigated time points whereas renal uptake was similar as observed for [$^{161}$Tb]Tb-DOTATOC ($p>0.05$) (see FIG. 14b; Table A6).

body weight), (iv) tumor size ($<800$ mm$^3$, $\geq 800$ and $<900$ mm$^3$, $\geq 900$ and $<1000$ mm$^3$, $\geq 1000$ mm$^3$), (v) tumor ulceration. A score $\geq 3$ was due for example to: (i) appearance of wrinkled, translucent skin; (ii) mouse in crouching position and/or apathetic (iii) a body weight loss of $\geq 15\%$ of initial body weight, (iv) a tumor volume of $\geq 1000$ mm$^3$, (v) a combination of a tumor size of $\geq 800$ mm$^3$ and body weight loss of $\geq 10\%$ and/or (vi) ulceration of the tumor.

TABLE A6

Biodistribution data obtained in AR42J tumor-bearing mice at 0.5, 2, 4, 24 and 48 h after injection of 0.2 nmol of [$^{161}$Tb]Tb-DOTA-LM3. Decay-corrected data are shown as % IA/g tissue, representing the average ± SD

| | [$^{161}$Tb]Tb-DOTA-LM3 (0.2 nmol/mouse) | | | | |
|---|---|---|---|---|---|
| | 0.5 h | 2 h | 4 h | 24 h | 48 h |
| Blood | 1.3 ± 0.2 | ≤0.10 | ≤0.10 | ≤0.10 | ≤0.10 |
| Heart | 0.83 ± 0.25 | 0.13 ± 0.01 | ≤0.10 | ≤0.10 | ≤0.10 |
| Lung | 4.4 ± 1.4 | 2.9 ± 0.7 | 2.3 ± 0.4 | 0.94 ± 0.45 | 0.59 ± 0.11 |
| Spleen | 0.77 ± 0.09 | 0.41 ± 0.08 | 0.38 ± 0.02 | 0.18 ± 0.02 | 0.20 ± 0.01 |
| Kidneys | 12 ± 1 | 9.5 ± 1.0 | 9.0 ± 1.2 | 5.9 ± 0.8 | 3.8 ± 0.5 |
| Adrenals | 1.6 ± 0.4 | 1.5 ± 0.2 | 1.6 ± 0.6 | 0.73 ± 0.31 | 0.53 ± 0.08 |
| Stomach | 7.7 ± 2.1 | 11 ± 1 | 8.3 ± 0.3 | 3.8 ± 1.2 | 3.4 ± 0.5 |
| Pancreas | 15 ± 2 | 17 ± 3 | 16 ± 1 | 6.1 ± 0.7 | 3.7 ± 0.5 |
| Intestines | 1.0 ± 0.3 | 0.74 ± 0.11 | 0.81 ± 0.41 | 0.39 ± 0.21 | 0.25 ± 0.07 |
| Liver | 0.93 ± 0.23 | 0.63 ± 0.24 | 0.51 ± 0.08 | 0.29 ± 0.08 | 0.27 ± 0.04 |
| Muscle | 0.32 ± 0.03 | ≤0.10 | ≤0.10 | ≤0.10 | ≤0.10 |
| Femur | 0.92 ± 0.29 | 0.53 ± 0.19 | 0.54 ± 0.06 | 0.29 ± 0.15 | 0.24 ± 0.01 |
| AR42J Tumor | 31 ± 7 | 33 ± 6 | 35 ± 7 | 26 ± 4 | 21 ± 4 |
| Tumor-to-blood | 24 ± 5 | 461 ± 29 | 820 ± 47 | 1371 ± 446 | 1249 ± 97 |
| Tumor-to-liver | 34 ± 7 | 53 ± 9 | 69 ± 2 | 95 ± 30 | 78 ± 10 |
| Tumor-to-kidney | 2.5 ± 0.4 | 3.4 ± 0.1 | 3.9 ± 0.1 | 4.5 ± 1.1 | 5.5 ± 0.8 |

E. Preclinical Therapy Study in AR42J-Tumor-Bearing Mice

The aim of this preclinical study was to evaluate the therapeutic effect and potential early side effects of DOTA-TOC and DOTA-LM3 peptides radiolabeled with either terbium-161 or lutetium-177.

The therapy study was initiated with mice randomly assigned to five groups (n=6) when the AR42J tumors reached an average volume of 99±16 mm3. At Day 0 and Day 7 of the study, the mice were intravenously injected with vehicle only (Group A: PBS with 0.05% BSA; sham-treatment), [$^{161}$Tb]Tb-DOTATOC (Group B: 10 MBq, 0.2 nmol), [$^{177}$Lu]Lu-DOTATOC (Group C: 10 MBq, 0.2 nmol), [$^{161}$Tb]Tb-DOTA-LM3 (Group D: 10 MBq, 0.2 nmol) and [$^{177}$Lu]Lu-DOTA-LM3 (Group E: 10 MBq, 0.2 nmol) (Table 5).

The relative body weight (RBW) and the relative tumor volume (RTV) were defined based on the values at therapy start as previously described [54]. The RBW was defined as [$BW_x/BW_0$], where $BW_x$ is the body weight in gram at a given Day x and $BW_0$ the body weight in gram at Day 0. The tumor dimension was determined by measuring the longest tumor axis (L) and its perpendicular axis (W) with a digital caliper. The tumor volume (TV) was calculated according to the equation [$TV=0.5\times(L\times W^2)$]. The relative tumor volume (RTV) was defined as [$TV_x/TV_0$], where $TV_x$ is the tumor volume in mm$^3$ at a given Day x and $TV_0$ the tumor volume in mm$^3$ at Day 0.

The endpoint criteria were defined according to a scoring system which required euthanasia of mice with a score ≥3. Every second day the following criteria were assessed in the mice assigning a score from 0-3 for each criterion: (i) appearance (general status, skin color, etc.), (ii) behavior (vitality, sociality. crouching etc.), (iii) body weight (stable, loss >5≤10%, loss >10<15%, loss >15% compared to initial The efficacy of the treatment was assessed by comparison of the RTVs, measured every second day, of mice in each group using a two-way ANOVA with Sidak's multiple comparisons post-test. The average tumor growth delay, herein defined as the time during which the tumors did not grow or even decreased in size, was determined for mice of each group. For the subsequent phase, in which the tumors started to regrow, the doubling time of the tumor volume was calculated based on the fitted exponential tumor growth curve. The average±SD of tumor growth delay and of the doubling time of the tumor volume in single mice, respectively, were compared among groups with a one-way ANOVA with Tukey's multiple comparisons post-test. The survival times of mice were presented by Kaplan-Meier curves and analyzed using a log-rank test (Mantel-Cox).

TABLE 5

Design of the therapy study including the average tumor volumes and body weights of mice at therapy start. The mice were injected at Day 0 and Day 7 with the respective radiopeptide at 0.2 nmol peptide amount per mouse (n = 6).

| Group | Treatment | Injected activity | Tumor volume$^2$ (mm$^3$) (average ± SD) Day 0 | Body weight$^3$ (g) (average ± SD) Day 0 |
|---|---|---|---|---|
| A | Vehicle$^1$ | — | 118 ± 90 | 23 ± 2 |
| B | [$^{161}$Tb]Tb-DOTATOC | 2 × 10 MBq | 92 ± 48 | 24 ± 2 |
| C | [$^{177}$Lu]Lu-DOTATOC | 2 × 10 MBq | 102 ± 56 | 24 ± 2 |
| D | [$^{161}$Tb]Tb-DOTA-LM3 | 2 × 10 MBq | 76 ± 32 | 23 ± 1 |

TABLE 5-continued

Design of the therapy study including the average tumor volumes and body weights of mice at therapy start. The mice were injected at Day 0 and Day 7 with the respective radiopeptide at 0.2 nmol peptide amount per mouse (n = 6).

| Group | Treatment | Injected activity | Tumor volume[2] (mm³) (average ± SD) Day 0 | Body weight[3] (g) (average ± SD) Day 0 |
|---|---|---|---|---|
| E | [$^{177}$Lu]Lu-DOTA-LM3 | 2 × 10 MBq | 109 ± 72 | 24 ± 2 |

[1]Vehicle: 0.05% BSA in PBS (pH 7.4);
[2]No significant differences determined between the tumor volumes measured for each group ($p > 0.05$);
[3]No significant differences determined between the body weights measured for each group ($p > 0.05$).

Figures 16A, 16B:
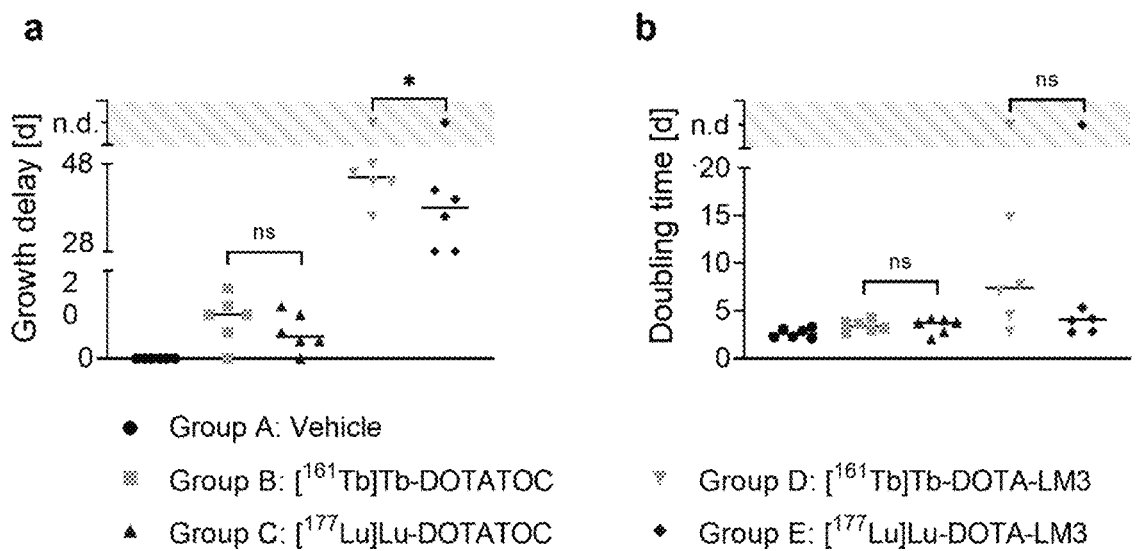
FIGS. 16A and 16B show analysis of the therapy study performed with $^{161}$Tb- and $^{177}$Lu-SST agonist and antagonist (2×10 MBq; 0.2 nmol) in AR42J tumor-bearing mice.

Sham-treated mice of Group A showed an exponential tumor growth so that the endpoint was reached within the first 14 days in all cases. The tumor growth was delayed in treated mice of Groups B-E, resulting in significantly prolonged median survival times as compared to the 9 days in the control group (FIG. 15, Table 6). Mice treated with [$^{161}$Tb]Tb-DOTATOC (Group B) showed a slightly slower tumor growth compared to mice treated with [$^{177}$Lu]Lu-DOTATOC (Group C). After 12 days from the therapy start, the RTV of mice of these two groups were significantly different (2.0±0.7 vs 4.0±3.3, p<0.05). The tumor growth delay and doubling time were higher in Group B (9.0±5.5 days and 3.4±3.6 days, respectively) compared to those of Group C (6.0±4.4 days and 3.4±0.8 days, respectively, p>0.05) (FIG. 16). Mice of Group B were, thus, euthanized at a later stage (Day 20-26) as compared to Group C (Day 12-22). The median survival (21 vs 19.5 days) was, however, comparable between the groups (p>0.05).

The tumor growth delay for mice treated with [$^{161}$Tb]Tb-DOTA-LM3 was 44±5 days, but only 35±7 days in mice treated with [$^{177}$Lu]Lu-DOTA-LM3 (p<0.05). Afterwards, the tumors started to regrow exponentially in 5 out of 6 mice of both groups, however, the doubling time was considerably longer for mice treated with [$^{161}$Tb]Tb-DOTA-LM3 as compared to the tumor growth in mice treated with [$^{177}$Lu]Lu-DOTA-LM3 (7.4±4.6 days vs 3.8±1.1 days, p>0.05) (FIG. 16). All mice treated with [$^{161}$Tb]Tb-DOTA-LM3 survived until the end of the study, while this was the case only for three out of six mice treated with [$^{177}$Lu]Lu-DOTA-LM3.

TABLE 6

Data regarding euthanasia period, median survival and tumor growth delay indices of mice.

| Group | Treatment | Time frame of euthanasia [d] | Median survival [d] |
|---|---|---|---|
| A | vehicle | 6-15 | 9 |
| B | [$^{161}$Tb]Tb-DOTATOC[a] | 20-26 | 21 |
| C | [$^{177}$Lu]Lu-DOTATOC[a] | 12-22 | 19.5 |
| D | [$^{161}$Tb]Tb-DOTA-LM3[a] | end of study[b] | n.d |
| E | [$^{177}$Lu]Lu-DOTA-LM3[a] | 42-48 (n = 3) end of study (n = 3) | 48.5 |

[a]1st injection: 10 MBq, 0.2 nmol at Day 0; 2nd Injection: 10 MBq, 0.2 nmol at Day 7.
[b]end of study = 49 days.
[c] significantly different from group A (p < 0.05)

F. Assessment of Early Side Effects

The aim was to assess signs of early side effects in mice treated with 2×10 MBq of [$^{161}$Tb]Tb-DOTATOC, [$^{177}$Lu]Lu-DOTATOC, [$^{161}$Tb]Tb-DOTA-LM3 or [$^{177}$Lu]Lu-DOTA-LM3.

Early side effects were assessed based on the RBW of each mouse which was monitored every second day. When an endpoint was reached or at the end of the study (after 49 days), relevant organs and tissues were collected, weighed and put into relation to the brain mass and body weight of the respective mouse. This allowed comparison of organ-to-brain and organ-to-body mass weight ratios. In addition, blood plasma parameters from blood collected immediately after euthanasia were measured.

RBW, organ mass and mass ratios at the endpoint: The RBW was monitored every second day. Mice were euthanized when a predefined endpoint criterion was reached or when the study was terminated at Day 49. RBWs, organ masses, organ mass ratios (kidney-to-brain, liver-to-brain and spleen-to-brain) and organ mass to body weight ratios (kidney-to-body mass, liver-to-body mass and spleen-to-body mass) were analyzed for significance using a one-way ANOVA test with a Tukey's multiple comparisons post-test. A p-value of <0.05 was considered as statistically significant.

Blood plasma chemistry: Immediately before euthanasia of the mice that reached the endpoint, blood was sampled from the retrobulbar vein. The values of creatinine (CRE), blood urea nitrogen (BUN), alkaline phosphatase (ALP), total bilirubin (TBIL) and albumin (ALB) were determined in the plasma after centrifugation of the blood using a dry chemistry analyzer (DRI-CHEM 4000i, FUJIFILM, Japan). The average blood plasma parameters of each group were analyzed for significance using a one-way ANOVA test with a Tukey's multiple comparisons post-test. A p-value of <0.05 was considered as statistically significant.

Figures 17A, 17B:
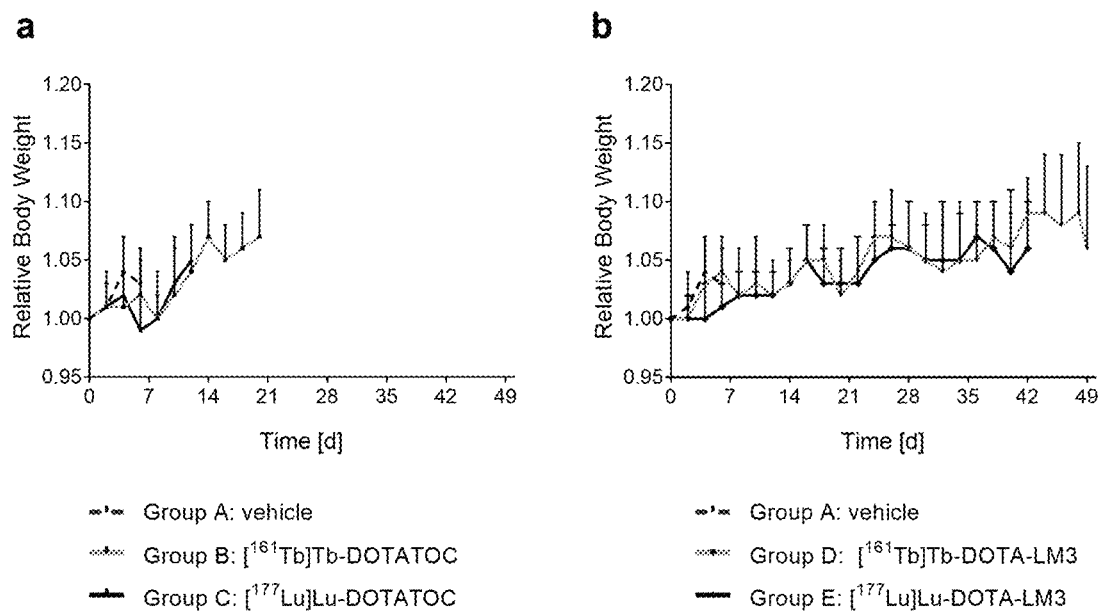
FIGS. 17A and 17B show Relative Body Weights (RBWs) of the therapy mice is depicted.
Figures 18A, 18B, 18C, 18D:
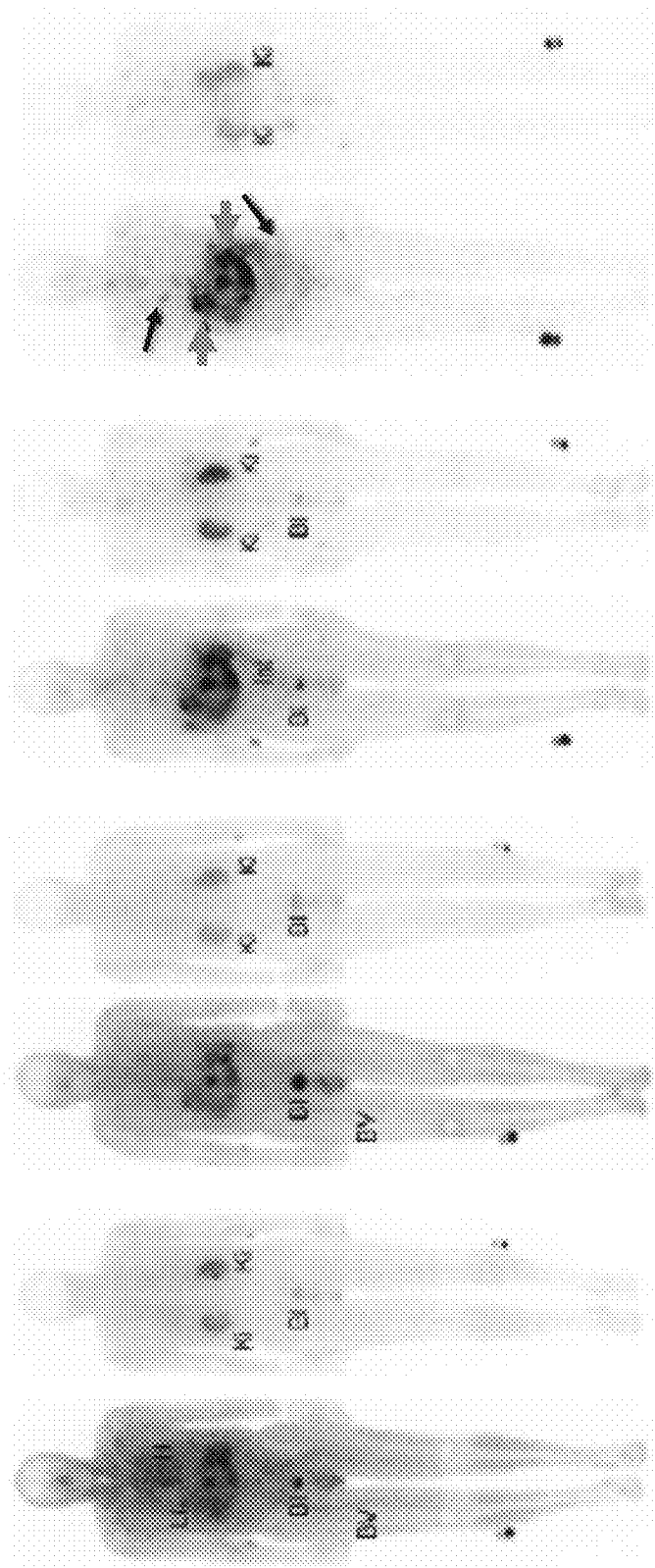
FIGS. 18A, 18B, 18C, and 18D are whole-body scintigraphy images obtained at 0.5 hours post-injection (p.i.) (FIG. 18A), 2.5 hours p.i.

No obvious early side effects were observed in treated mice. The relative body weights increased over the course of the study, a sign of the well-being of the mice (see FIG. 17). No difference in body weights was observed between control mice and treated mice at Day 6, when the first mouse of the control group reached an endpoint (p>0.05) (Table 7). At the time of euthanasia, the organ masses, the organ-to-brain ratios and the organ-to-body mass ratios showed no significant difference between treated mice (Groups B-E) and untreated controls (Group A) (p>0.05) (Tables 8 and 9).

Blood plasma chemistry revealed no difference among treated mice and untreated controls. The BUN levels were in the acceptable range for all mice, however, elevated in mice treated with [$^{161}$Tb]Tb-DOTA-LM3 (9.9±1.5 mmol/L; p<0.05) and [$^{177}$Lu]Lu-DOTA-LM3 (8.2±1.9 mmol/L; p>0.05) as compared to control mice (6.2±0.7 mmol/L) (Table 10)

TABLE 7

Relative body weight of mice at Day 6 and at the endpoint of the therapy study. No significant difference among the groups was observed (p > 0.05).

| Group (n = 6) | Relative body weight at Day 6[1] (average ± SD) | Relative body weight at end-point[2] (average ± SD) |
|---|---|---|
| A | 1.03 ± 0.03 | 1.05 ± 0.03 |
| B | 1.02 ± 0.03 | 1.07 ± 0.02 |
| C | 0.99 ± 0.03 | 1.01 ± 0.07 |

TABLE 7-continued

Relative body weight of mice at Day 6 and at the endpoint of the therapy study. No significant difference among the groups was observed (p > 0.05).

| Group (n = 6) | Relative body weight at Day 6[1] (average ± SD) | Relative body weight at end-point[2] (average ± SD) |
|---|---|---|
| D | 1.04 ± 0.03 | 1.06 ± 0.07 |
| E | 1.01 ± 0.02 | 1.11 ± 0.06 |

[1]Data obtained at Day 6 when the first control mouse reached an endpoint.
[2]Data obtained at the day of euthanasia when an endpoint criterion was reached or at the end of the study.

TABLE 8

Organ mass of mice of the therapy study collected after euthanasia. No significant difference among the groups was observed (p > 0.05).

| Group (n = 6) | Organ mass[1] (mg) (average ± SD) | | | |
|---|---|---|---|---|
| | Kidneys | Liver | Spleen | Brain |
| A | 327 ± 28 | 1096 ± 128 | 90 ± 10 | 429 ± 23 |
| B | 352 ± 27 | 1195 ± 57 | 86 ± 19 | 440 ± 23 |
| C | 342 ± 23 | 1121 ± 123 | 90 ± 17 | 453 ± 31 |
| D | 332 ± 46 | 1275 ± 254 | 85 ± 27 | 465 ± 30 |
| E | 336 ± 13 | 1254 ± 106 | 92 ± 17 | 471 ± 30 |

[1]Data obtained at the day of euthanasia when an endpoint criterion was reached or at the end of the study.

TABLE 9

Organ mass-to-brain mass and organ mass-to-body weight ratios. No significant difference among the groups was observed (p > 0.05).

| Group (n = 6) | Organ mass-to-brain mass ratios (average ± SD) | | |
|---|---|---|---|
| | Kidney-to-brain | Liver-to-brain | Spleen-to-brain |
| A | 0.77 ± 0.09 | 2.6 ± 0.3 | 0.21 ± 0.03 |
| B | 0.80 ± 0.03 | 2.7 ± 0.2 | 0.20 ± 0.05 |
| C | 0.76 ± 0.03 | 2.5 ± 0.2 | 0.20 ± 0.03 |
| D | 0.72 ± 0.12 | 2.8 ± 0.7 | 0.19 ± 0.07 |
| E | 0.72 ± 0.05 | 2.7 ± 0.1 | 0.20 ± 0.04 |

| Group (n = 6) | Organ mass-to-body weight ratios (average ± SD) | | |
|---|---|---|---|
| | Kidney-to-body | Liver-to-body | Spleen-to-body |
| A | 0.013 ± 0.001 | 0.047 ± 0.002 | 0.004 ± 0.000 |
| B | 0.013 ± 0.001 | 0.049 ± 0.004 | 0.003 ± 0.001 |
| C | 0.014 ± 0.001 | 0.050 ± 0.003 | 0.004 ± 0.001 |
| D | 0.014 ± 0.001 | 0.050 ± 0.001 | 0.004 ± 0.001 |
| E | 0.014 ± 0.001 | 0.050 ± 0.003 | 0.003 ± 0.001 |

TABLE 10

Plasma chemistry determined at the endpoint of the therapy (n = 6, if not differently indicated)

| Group | CRE (μmol/L) | BUN (mmol/L) | ALP (U/L) | TBIL (μmol/L) | ALB (g/L) |
|---|---|---|---|---|---|
| A | <18 (n = 6) | 6.2 ± 0.7 | 71 ± 15 | <3 (n = 2) 3 ± 1 (n = 4) | 22 ± 2 |
| B | <18 (n = 6) | 5.8 ± 1.0 | 76 ± 21 | <3 (n = 4) 4 ± 1 (n = 2) | 23 ± 2 |
| C | <18 (n = 5) | 6.3 ± 0.9 | 77 ± 8 | <3 (n = 3) 4 ± 1 (n = 3) | 24 ± 5 |
| D | <18 (n = 5) 18 (n = 1) | 9.1 ± 1.5* | 65 ± 15 | <3 (n = 5) 3 (n = 1) | 22 ± 1 |
| E | <18 (n = 5) 19 (n = 1) | 8.2 ± 1.8** | 66 ± 5 | <3 (n = 4) 4 ± 1 (n = 2) | 23 ± 1 |

*Significantly different (p < 0.05) from the value of Group A, B, C.
**Significantly different (p < 0.05) from the value of Group B.

First-In-Man Application of 161Tb-DOTATOC

Radiolabeling of DOTATOC with 161Tb was performed at the Klinikum Bad Berka in Germany (Prof. R. Baum). A 70-year-old male patient with a metastatic functional neuroendocrine neoplasm of the pancreatic tail was injected with 161TbDOTATOC. Scintigraphy and SPECT were recorded. The image quality was comparable to the 177Lu-labeled counterpart. FIGS. 18A, 18B, 18C, and 18D show whole-body images obtained at 0.5 hours post-injection (p.i.) (FIG. 18A), 2.5 hours p.i. (FIG. 18B), 20 hours p.i. (FIG. 18C), and 113 hours p.i. (FIG. 18D) of 161Tb-DOTATOC. Early blood-pool activity was noticed in the heart (H) and blood vessels (BV). Physiological uptake was seen in the soft tissues, liver (Li), kidneys (Ki), and the bladder (Bl). Pathological uptake was demonstrated in the bilobar liver (thick gray arrows) and multifocal osseous metastases (black arrows).

Figures 19A, 19B, 19C:
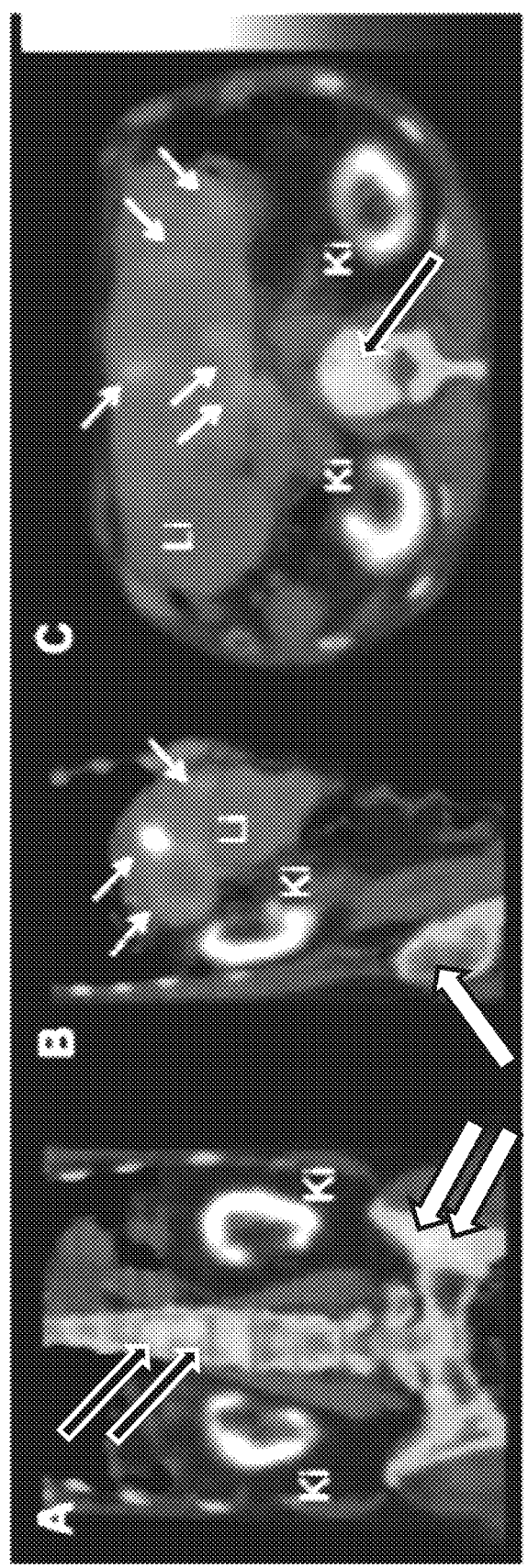
FIGS. 19A, 19B, and 19C show SPECT/CT images obtained at 19 hours after injection of 161Tb-DOTATOC.

FIGS. 19A, 19B, and 19C show SPECT/CT images obtained at 19 hours after injection of 161Tb-DOTATOC. (FIG. 19A) Coronal section, (FIG. 19B) sagittal section, and (FIG. 19C) transverse section. Uptake of 161-DOTATOC was seen in bilobar hepatic metastases (white arrows), as well as multiple osteoblastic skeletal metastases in the vertebral column (black-filled arrows and the pelvis (thick white arrows).

REFERENCES

All documents cited herein are incorporated by reference.
1. Cives M, Strosberg J. Radionuclide therapy for neuroendocrine tumors. Curr Oncol Rep. 2017; 19:9. doi:10.1007/s11912-017-0567-8.
2. Yao J C, Hassan M, Phan A, Dagohoy C, Leary C, Mares J E, et al. One hundred years after "carcinoid": epidemiology of and prognostic factors for neuroendocrine tumors in 35,825 cases in the United States. J Clin Oncol. 2008; 26:3063-72. doi:10.1200/JCO.2007.15.4377.
3. Krenning E P, Kooij P P, Bakker W H, Breeman W A, Postema P T, Kwekkeboom D J, et al. Radiotherapy with a radiolabeled somatostatin analogue, [111In-DTPA-D-Phe1]-octreotide. A case history. Ann N Y Acad Sci. 1994; 733:496-506. doi:10.1111/j.1749-6632.1994.tb17300.x.
4. Kwekkeboom D J, Krenning E P. Peptide receptor radionuclide therapy in the treatment of neuroendocrine tumors. Hematol Oncol Clin North Am. 2016; 30:179-91. doi:10.1016/j.hoc.2015.09.009.
5. Valkema R, De Jong M, Bakker W H, Breeman W A, Kooij P P, Lugtenburg P J, et al. Phase I study of peptide receptor radionuclide therapy with [In-DTPA]octreotide: the Rotterdam experience. Semin Nucl Med. 2002; 32:110-22. doi:10.1053/snuc/2002.31025.

6. Anthony L B, Woltering E A, Espenan G D, Cronin M D, Maloney T J, McCarthy K E. Indium-111-pentetreotide prolongs survival in gastroenteropancreatic malignancies. Semin Nucl Med. 2002; 32:123-32. doi:10.1053/snuc.2002.31769.
7. Nisa L, Savelli G, Giubbini R. Yttrium-90 DOTATOC therapy in GEP-NET and other SST2 expressing tumors: a selected review. Ann Nucl Med. 2011; 25:75-85. doi:10.1007/s12149-010-0444-0.
8. Valkema R, Pauwels S A, Kvols L K, Kwekkeboom D J, Jamar F, de Jong M, et al. Long-term follow-up of renal function after peptide receptor radiation therapy with 90Y-DOTA0,Tyr3-octreotide and 177Lu-DOTA0,Tyr3-octreotate. J Nucl Med. 2005; 46 Suppl 1:83S-91S. doi:46/1_suppl/83S [pii].
9. Valkema R, Pauwels S, Kvols L K, Barone R, Jamar F, Bakker W H, et al. Survival and response after peptide receptor radionuclide therapy with [90Y-DOTA0,Tyr3] octreotide in patients with advanced gastroenteropancreatic neuroendocrine tumors. Semin Nucl Med. 2006; 36:147-56. doi:10.1053/j.semnuclmed.2006.01.001.
10. Banerjee S, Pillai M R, Knapp F F. Lutetium-177 therapeutic radiopharmaceuticals: linking chemistry, radiochemistry, and practical applications. Chem Rev. 2015; 115:2934-74. doi:10.1021/cr500171e.
11. Kwekkeboom D J, Bakker W H, Kam B L, Teunissen J J, Kooij P P, de Herder W W, et al. Treatment of patients with gastro-entero-pancreatic (GEP) tumours with the novel radiolabelled somatostatin analogue [177Lu-DOTA0,Tyr3]octreotate. Eur J Nucl Med Mol Imaging. 2003; 30:417-22. doi:10.1007/s00259-002-1050-8.
12. Romer A, Seiler D, Marincek N, Brunner P, Koller M T, Ng Q K, et al. Somatostatin-based radiopeptide therapy with [177Lu-DOTA]-TOC versus [90Y-DOTA]-TOC in neuroendocrine tumours. Eur J Nucl Med Mol Imaging. 2014; 41:214-22. doi:10.1007/s00259-013-2559-8.
13. Strosberg J, El-Haddad G, Wolin E, Hendifar A, Yao J, Chasen B, et al. Phase 3 trial of 177Lu-DOTATATE for Mmidgut neuroendocrine tumors. N Engl J Med. 2017; 376:125-35. doi:10.1056/NEJMoa1607427.
14. Pillai A M, Knapp F F, Jr. Evolving Important role of lutetium-177 for therapeutic nuclear medicine. Curr Radiopharm. 2015; 8:78-85. doi:10.2174/1874471008666150312155959.
15. Baum R P, Kluge A W, Kulkarni H, Schorr-Neufing U, Niepsch K, Bitterlich N, et al. [177Lu-DOTA]0-D-Phe1-Tyr3-Octreotide (177Lu-DOTATOC) for peptide receptor radiotherapy in patients with advanced neuroendocrine tumours: a Phase-II study. Theranostics. 2016; 6:501-10. doi:10.7150/thno.13702.
16. Pouget J P, Lozza C, Deshayes E, Boudousq V, Navarro-Teulon I. Introduction to radiobiology of targeted radionuclide therapy. Front Med (Lausanne). 2015; 2:12. doi:10.3389/fmed.2015.00012.
17. Norenberg J P, Krenning B J, Konings I R, Kusewitt D F, Nayak T K, Anderson T L, et al. 213Bi-[DOTA0, Tyr3]octreotide peptide receptor radionuclide therapy of pancreatic tumors in a preclinical animal model. Clin Cancer Res. 2006; 12:897-903. doi:10.1158/1078-0432.CCR-05-1264.
18. Chan H S, Konijnenberg M W, de Blois E, Koelewijn S, Baum R P, Morgenstern A, et al. Influence of tumour size on the efficacy of targeted alpha therapy with 213Bi-[DOTA(0),Tyr3]-octreotate. EJNMMI Res. 2016; 6:6. doi:10.1186/s13550-016-0162-2.
19. Miederer M, Henriksen G, Alke A, Mossbrugger I, Quintanilla-Martinez L, Senekowitsch-Schmidtke R, et al. Preclinical evaluation of the alpha-particle generator nuclide 225Ac for somatostatin receptor radiotherapy of neuroendocrine tumors. Clin Cancer Res. 2008; 14:3555-61. doi:10.1158/1078-0432.CCR-07-4647.
20. Tafreshi N K, Pandya D N, Tichacek C J, Budzevich M M, Wang Z, Reff J N, et al. Preclinical evaluation of [225Ac]Ac-DOTA-TATE for treatment of lung neuroendocrine neoplasms. Eur J Nucl Med Mol Imaging. 2021. doi:10.1007/s00259-021-05315-1.
21. Kratochwil C, Giesel F L, Bruchertseifer F, Mier W, Apostolidis C, Boll R, et al. 213Bi-DOTATOC receptor-targeted alpha-radionuclide therapy induces remission in neuroendocrine tumours refractory to beta radiation: a first-in-human experience. Eur J Nucl Med Mol Imaging. 2014; 41:2106-19. doi:10.1007/s00259-014-2857-9.
22. Ballal S, Yadav M P, Bal C, Sahoo R K, Tripathi M. Broadening horizons with 225Ac-DOTATATE targeted alpha therapy for gastroenteropancreatic neuroendocrine tumour patients stable or refractory to 177Lu-DOTATATE PRRT: first clinical experience on the efficacy and safety. Eur J Nucl Med Mol Imaging. 2020; 47:934-46. doi:10.1007/s00259-019-04567-2.
23. de Kruijff R M, Wolterbeek H T, Denkova A G. A critical review of alpha radionuclide therapy-how to deal with recoiling daughters? Pharmaceuticals (Basel). 2015; 8:321-36. doi:10.3390/ph8020321.
24. Kratochwil C, Bruchertseifer F, Giesel F L, Weis M, Verburg F A, Mottaghy F, et al. 225Ac-PSMA-617 for PSMA-targeted alpha-radiation therapy of metastatic castration-resistant prostate cancer. J Nucl Med. 2016; 57:1941-4. doi:10.2967/jnumed.116.178673.
25. Morgenstern A, Apostolidis C, Kratochwil C, Sathekge M, Krolicki L, Bruchertseifer F. An overview of targeted alpha therapy with 225Actinium and 213Bismuth. Curr Radiopharm. 2018; 11:200-8. doi:10.2174/1874471011666180502104524.
26. Lehenberger S, Barkhausen C, Cohrs S, Fischer E, Grunberg J, Hohn A, et al. The low-energy beta- and electron emitter 161Tb as an alternative to 177Lu for targeted radionuclide therapy. Nucl Med Biol. 2011; 38:917-24. doi:S0969-8051(11)00044-8 [pii] 10.1016/j.nucmed-bio.2011.02.007.
27. Duran M T, Juget F, Nedjadi Y, Bochud F, Grundler P V, Gracheva N, et al. Determination of 161Tb half-life by three measurement methods. Appl Radiat Isot. 2020; 159:109085. doi:10.1016/j.apradiso.2020.109085.
28. Baum R P, Singh A, Kulkarni H R, Bernhardt P, Ryden T, Schuchardt C, et al. First-in-human application of terbium-161: a feasibility study using 161Tb-DOTATOC. J Nucl Med. 2021. doi:10.2967/jnumed.120.258376.
29. Müller C, Zhernosekov K, Köster U, Johnston K, Dorrer H, Hohn A, et al. A unique matched quadruplet of terbium radioisotopes for PET and SPECT and for a- and b-radionuclide therapy: An in vivo proof-of-concept study with a new receptor-targeted folate derivative. J Nucl Med. 2012; 53:1951-9. doi:10.2967/jnumed.112.107540/jnumed.112.107540 [pii].
34. Müller C, Reber J, Haller S, Dorrer H, Bernhardt P, Zhernosekov K, et al. Direct in vitro and in vivo comparison of 161Tb and 177Lu using a tumour-targeting folate conjugate. Eur J Nucl Med Mol Imaging. 2014; 41:476-85. doi:10.1007/s00259-013-2563-z.
36. Müller C, Umbricht C A, Gracheva N, Tschan V J, Pellegrini G, Bernhardt P, et al. Terbium-161 for PSMA-targeted radionuclide therapy of prostate cancer. Eur J Nucl Med Mol Imaging. 2019; 46:1919-30. doi:10.1007/s00259-019-04345-0.

39. Fani M, Andre J P, Maecke H R. 68Ga-PET: a powerful generator-based alternative to cyclotron-based PET radiopharmaceuticals. Contrast Media Mol Imaging. 2008; 3:67-77. doi:10.1002/cmmi.232.
41. Wang L F, Lin L, Wang M J, Li Y. The therapeutic efficacy of 177Lu-DOTATATE/DOTATOC in advanced neuroendocrine tumors: a meta-analysis. Medicine (Baltimore). 2020; 99:e19304. doi:10.1097/MD.0000000000019304.
42. Fani M, Del Pozzo L, Abiraj K, Mansi R, Tamma M L, Cescato R, et al. PET of somatostatin receptor-positive tumors using 64Cu- and 68Ga-somatostatin antagonists: the chelate makes the difference. J Nucl Med. 2011; 52:1110-8. doi:10.2967/jnumed.111.087999.
43. Gracheva N, Müller C, Talip Z, Heinitz S, Köster U, Zeevaart J R, et al. Production and characterization of no-carrier-added 161Tb as an alternative to the clinically-applied 177Lu for radionuclide therapy. EJNMMI Radiopharm Chem. 2019; 4:12. doi:10.1186/s41181-019-0063-6.
44. Borgna F, Barritt P, Grundler P V, Talip Z, Cohrs S, Zeevaart J R, et al. Simultaneous visualization of 161Tb- and 177Lu-labeled somatostatin analogues using dual-isotope SPECT imaging. Pharmaceutics. 2021; 13. doi: 10.3390/pharmaceutics13040576.
45. Ku A, Facca V J, Cai Z, Reilly R M. Auger electrons for cancer therapy—a review. EJNMMI Radiopharm Chem. 2019; 4:27. doi:10.1186/s41181-019-0075-2.
46. Iori M, Capponi P C, Rubagotti S, Esposizione L R, Seemann J, Pitzschler R, et al. Labelling of 90Y- and 177Lu-DOTA-bioconjugates for targeted radionuclide therapy: a comparison among manual, semiautomated, and fully automated synthesis. Contrast Media Mol Imaging. 2017; 2017:8160134. doi:10.1155/2017/8160134.
47. Müller C, Mindt T L, de Jong M, Schibli R. Evaluation of a novel radiofolate in tumour-bearing mice: promising prospects for folate-based radionuclide therapy. Eur J Nucl Med Mol Imaging. 2009; 36:938-46.
48. Hofsli E, Thommesen L, Norsett K, Falkmer S, Syversen U, Sandvik A, et al. Expression of chromogranin A and somatostatin receptors in pancreatic AR42J cells. Mol Cell Endocrinol. 2002; 194:165-73. doi:10.1016/s0303-7207(02)00131-4.
49. Cescato R, Schulz S, Waser B, Eltschinger V, Rivier J E, Wester H J, et al. Internalization of sst2, sst3, and sst5 receptors: effects of somatostatin agonists and antagonists. J Nucl Med. 2006; 47:502-11.
50. Wadas T J, Eiblmaier M, Zheleznyak A, Sherman C D, Ferdani R, Liang K, et al. Preparation and biological evaluation of 64Cu-CB-TE2A-sst2-ANT, a somatostatin antagonist for PET imaging of somatostatin receptor-positive tumors. J Nucl Med. 2008; 49:1819-27. doi: 10.2967/jnumed.108.054502jnumed.108.054502 [pii].
51. Mosmann T. Rapid colorimetric assay for cellular growth and survival: application to proliferation and cytotoxicity assays. J Immunol Methods. 1983; 65:55-63. doi:10.1016/0022-1759(83)90303-4.
52. Franken N A, Rodermond H M, Stap J, Haveman J, van Bree C. Clonogenic assay of cells in vitro. Nat Protoc. 2006; 1:2315-9. doi:10.1038/nprot.2006.339.
53. Nicolas G P, Mansi R, McDougall L, Kaufmann J, Bouterfa H, Wild D, et al. Biodistribution, pharmacokinetics, and dosimetry of 177Lu-, 90Y-, and 111In-labeled somatostatin receptor antagonist OPS201 in comparison to the agonist 177Lu-DOTATATE: the mass effect. J Nucl Med. 2017; 58:1435-41. doi:10.2967/jnumed.117.191684.
54. Guzik P, Benesova M, Ratz M, Monne Rodriguez J M, Deberle L M, Schibli R, et al. Preclinical evaluation of 5-methyltetrahydrofolate-based radioconjugates-new perspectives for folate receptor-targeted radionuclide therapy. Eur J Nucl Med Mol Imaging. 2021; 48:972-83. doi:10.1007/500259-020-04980-y.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

SEQUENCE LISTING

```
Sequence total quantity: 27
SEQ ID NO: 1            moltype = AA  length = 8
FEATURE                 Location/Qualifiers
source                  1..8
                        mol_type = protein
                        organism = synthetic construct
SITE                    2
                        note = D-cysteine
SITE                    8
                        note = D-tyrosine
SEQUENCE: 1
XCXXKTCY                                                                  8

SEQ ID NO: 2            moltype = AA  length = 8
FEATURE                 Location/Qualifiers
source                  1..8
                        mol_type = protein
                        organism = synthetic construct
MOD_RES                 1
                        note = p-chloro-phenylalanine
SITE                    2
                        note = D-cysteine
MOD_RES                 4
                        note = D-(4-amino-Phe(carbamoyl))
SITE                    8
```

```
                              note = D-tyrosine
SEQUENCE: 2
XCYXKTCY                                                        8

SEQ ID NO: 3         moltype = AA   length = 8
FEATURE              Location/Qualifiers
source               1..8
                     mol_type = protein
                     organism = synthetic construct
MOD_RES              1
                     note = [(S)-4-(Carboxamido)phenylalanine
SITE                 2
                     note = D-cysteine
MOD_RES              3
                     note = 4-amino-L-hydroorotyl-phenylalanine
MOD_RES              4
                     note = D-(4-amino-Phe(carbamoyl))
SITE                 8
                     note = D-tyrosine
SEQUENCE: 3
XCXXKTCY                                                        8

SEQ ID NO: 4         moltype = AA   length = 8
FEATURE              Location/Qualifiers
source               1..8
                     mol_type = protein
                     organism = synthetic construct
MOD_RES              1
                     note = p-nitrophenylalanine
SITE                 2
                     note = D-cysteine
SITE                 4
                     note = D-tryptophan
SITE                 8
                     note = D-tyrosine
SEQUENCE: 4
XCYWKTCY                                                        8

SEQ ID NO: 5         moltype = AA   length = 8
FEATURE              Location/Qualifiers
source               1..8
                     mol_type = protein
                     organism = synthetic construct
MOD_RES              1
                     note = p-nitrophenylalanine
SITE                 2
                     note = D-cysteine
MOD_RES              4
                     note = D-(4-amino-Phe(carbamoyl))
SITE                 8
                     note = D-tryosine
SEQUENCE: 5
XCYXKTCY                                                        8

SEQ ID NO: 6         moltype = AA   length = 8
FEATURE              Location/Qualifiers
source               1..8
                     mol_type = protein
                     organism = synthetic construct
MOD_RES              1
                     note = p-nitrophenylalanine
SITE                 2
                     note = D-cysteine
MOD_RES              4
                     note = D-(4-amino-Phe(carbamoyl))
SITE                 8
                     note = D-tyrosine
SEQUENCE: 6
XCYXKTCX                                                        8

SEQ ID NO: 7         moltype = AA   length = 8
FEATURE              Location/Qualifiers
source               1..8
                     mol_type = protein
                     organism = synthetic construct
MOD_RES              1
                     note = p-nitrophenylalanine
SITE                 2
                     note = D-cysteine
```

| | | |
|---|---|---|
| MOD_RES | 4 | |
| | note = D-(4-amino-Phe(carbamoyl)) | |
| MOD_RES | 8 | |
| | note = 3-(2-naphthyl)alanine | |
| SEQUENCE: 7 | | |
| XCYXKTCX | | 8 |
| | | |
| SEQ ID NO: 8 | moltype = AA  length = 8 | |
| FEATURE | Location/Qualifiers | |
| source | 1..8 | |
| | mol_type = protein | |
| | organism = synthetic construct | |
| MOD_RES | 1 | |
| | note = p-nitrophenylalanine | |
| SITE | 2 | |
| | note = D-cysteine | |
| MOD_RES | 3 | |
| | note = 4-amino-L-hydroorotyl-phenylalanine | |
| MOD_RES | 4 | |
| | note = D-(4-amino-Phe(carbamoyl)) | |
| MOD_RES | 8 | |
| | note = 3-(2-naphthyl)alanine | |
| SEQUENCE: 8 | | |
| XCXXKTCX | | 8 |
| | | |
| SEQ ID NO: 9 | moltype = AA  length = 8 | |
| FEATURE | Location/Qualifiers | |
| source | 1..8 | |
| | mol_type = protein | |
| | organism = synthetic construct | |
| MOD_RES | 1 | |
| | note = 4-Cl-phenylalanine | |
| SITE | 2 | |
| | note = D-cysteine | |
| MOD_RES | 3 | |
| | note = L-aminoglycine(NMe,benzoyl) | |
| SITE | 4 | |
| | note = D-tryptophan | |
| MOD_RES | 8 | |
| | note = 3-(2-naphthyl)alanine | |
| SEQUENCE: 9 | | |
| XCXWKTCX | | 8 |
| | | |
| SEQ ID NO: 10 | moltype = AA  length = 8 | |
| FEATURE | Location/Qualifiers | |
| source | 1..8 | |
| | mol_type = protein | |
| | organism = synthetic construct | |
| MOD_RES | 1 | |
| | note = 4-Cl-phenylalanine | |
| SITE | 2 | |
| | note = D-cysteine | |
| MOD_RES | 3 | |
| | note = L-aminoglycine(NMe,benzoyl) | |
| SITE | 4 | |
| | note = D-tryptophan | |
| MOD_RES | 8 | |
| | note = 3-(2-naphthyl)alanine | |
| SEQUENCE: 10 | | |
| XCXWKTCX | | 8 |
| | | |
| SEQ ID NO: 11 | moltype = AA  length = 8 | |
| FEATURE | Location/Qualifiers | |
| source | 1..8 | |
| | mol_type = protein | |
| | organism = synthetic construct | |
| MOD_RES | 1 | |
| | note = 4-Cl-phenylalanine | |
| SITE | 2 | |
| | note = D-cysteine | |
| SITE | 4 | |
| | note = D-tryptophan | |
| MOD_RES | 8 | |
| | note = 3-(2-naphthyl)alanine | |
| SEQUENCE: 11 | | |
| XCLWKTCX | | 8 |
| | | |
| SEQ ID NO: 12 | moltype = AA  length = 8 | |
| FEATURE | Location/Qualifiers | |

```
source                    1..8
                          mol_type = protein
                          organism = synthetic construct
MOD_RES                   1
                          note = 4-Cl-phenylalanine
SITE                      2
                          note = D-cysteine
MOD_RES                   3
                          note = 4-amino-Phe(carbamoyl)
SITE                      4
                          note = D-tryptophan
MOD_RES                   8
                          note = 3-(2-naphthyl)alanine
SEQUENCE: 12
XCXWKTCX                                                                    8

SEQ ID NO: 13             moltype = AA   length = 8
FEATURE                   Location/Qualifiers
source                    1..8
                          mol_type = protein
                          organism = synthetic construct
MOD_RES                   1
                          note = N-[(4-Chlorophenyl)carbamoyl]-D-phenylalanine
SITE                      2
                          note = D-cysteine
MOD_RES                   3
                          note = 4-amino-Phe(carbamoyl)
SITE                      4
                          note = D-tryptophan
MOD_RES                   8
                          note = 3-(2-naphthyl)alanine
SEQUENCE: 13
XCXWKTCX                                                                    8

SEQ ID NO: 14             moltype = AA   length = 9
FEATURE                   Location/Qualifiers
source                    1..9
                          mol_type = protein
                          organism = synthetic construct
MOD_RES                   1
                          note = [beta]alanine
MOD_RES                   2
                          note = 4-Cl-phenylalanine
SITE                      3
                          note = D-cysteine
MOD_RES                   4
                          note = 4-amino-Phe(carbamoyl)
SITE                      5
                          note = D-tryptophan
MOD_RES                   9
                          note = 3-(2-naphthyl)alanine
SEQUENCE: 14
XXCXWKTCX                                                                   9

SEQ ID NO: 15             moltype = AA   length = 8
FEATURE                   Location/Qualifiers
source                    1..8
                          mol_type = protein
                          organism = synthetic construct
MOD_RES                   1
                          note = 4-Cl-phenylalanine
SITE                      2
                          note = D-cysteine
MOD_RES                   3
                          note = 4-amino-Phe(carbamoyl)
SITE                      4
                          note = D-tryptophan
MOD_RES                   8
                          note = 3-(2-naphthyl)alanine
SEQUENCE: 15
XCXWKRCX                                                                    8

SEQ ID NO: 16             moltype = AA   length = 7
FEATURE                   Location/Qualifiers
source                    1..7
                          mol_type = protein
                          organism = synthetic construct
MOD_RES                   1
                          note = 4-Cl-phenylalanine
```

| | | |
|---|---|---|
| SITE | 2 | |
| | note = D-cysteine | |
| MOD_RES | 3 | |
| | note = 4-amino-Phe(carbamoyl) | |
| SITE | 4 | |
| | note = 4-amino-Phe(carbamoyl) | |
| SEQUENCE: 16 | | |
| XCXWKTC | | 7 |
| | | |
| SEQ ID NO: 17 | moltype = AA  length = 8 | |
| FEATURE | Location/Qualifiers | |
| source | 1..8 | |
| | mol_type = protein | |
| | organism = synthetic construct | |
| MOD_RES | 1 | |
| | note = 4-Cl-phenylalanine | |
| SITE | 2 | |
| | note = D-cysteine | |
| MOD_RES | 3 | |
| | note = 4-amino-Phe(carbamoyl) | |
| SITE | 4 | |
| | note = D-tryptophan | |
| MOD_RES | 8 | |
| | note = 3-cyclohexyl-L-alaninamide | |
| SEQUENCE: 17 | | |
| XCXWKTCX | | 8 |
| | | |
| SEQ ID NO: 18 | moltype = AA  length = 8 | |
| FEATURE | Location/Qualifiers | |
| source | 1..8 | |
| | mol_type = protein | |
| | organism = synthetic construct | |
| MOD_RES | 1 | |
| | note = 4-Cl-phenylalanine | |
| SITE | 2 | |
| | note = D-cysteine | |
| MOD_RES | 3 | |
| | note = 4-amino-Phe(carbamoyl) | |
| SITE | 4 | |
| | note = D-tryptophan | |
| MOD_RES | 8 | |
| | note = 4-amino-L-hydroorotyl-phenylalanine | |
| SEQUENCE: 18 | | |
| XCXWKTCX | | 8 |
| | | |
| SEQ ID NO: 19 | moltype = AA  length = 8 | |
| FEATURE | Location/Qualifiers | |
| source | 1..8 | |
| | mol_type = protein | |
| | organism = synthetic construct | |
| MOD_RES | 1 | |
| | note = 4-Cl-phenylalanine | |
| SITE | 2 | |
| | note = D-cysteine | |
| MOD_RES | 3 | |
| | note = 4-amino-Phe(carbamoyl) | |
| SITE | 4 | |
| | note = D-tryptophan | |
| MOD_RES | 8 | |
| | note = D-4-amino-Phe(carbamoyl) | |
| SEQUENCE: 19 | | |
| XCXWKTCX | | 8 |
| | | |
| SEQ ID NO: 20 | moltype = AA  length = 8 | |
| FEATURE | Location/Qualifiers | |
| source | 1..8 | |
| | mol_type = protein | |
| | organism = synthetic construct | |
| MOD_RES | 1 | |
| | note = 4-Cl-phenylalanine | |
| SITE | 2 | |
| | note = D-cysteine | |
| MOD_RES | 3 | |
| | note = 4-amino-Phe(carbamoyl) | |
| SITE | 4 | |
| | note = D-tryptophan | |
| MOD_RES | 8 | |
| | note = 4-amino-Phe(carbamoyl) | |
| SEQUENCE: 20 | | |

```
XCXWKTCX                                                                        8

SEQ ID NO: 21           moltype = AA  length = 9
FEATURE                 Location/Qualifiers
source                  1..9
                        mol_type = protein
                        organism = synthetic construct
MOD_RES                 1
                        note = 4-Cl-phenylalanine
SITE                    2
                        note = D-cysteine
MOD_RES                 3
                        note = 4-amino-Phe(carbamoyl)
SITE                    4
                        note = D-tryptophan
MOD_RES                 8
                        note = D-4-amino-Phe(carbamoyl)
SEQUENCE: 21
XCXWKTCXX                                                                       9

SEQ ID NO: 22           moltype = AA  length = 8
FEATURE                 Location/Qualifiers
source                  1..8
                        mol_type = protein
                        organism = synthetic construct
MOD_RES                 1
                        note = 4-Cl-phenylalanine
SITE                    2
                        note = D-cysteine
MOD_RES                 3
                        note = 4-amino-Phe(CONH-OCH3)
SITE                    4
                        note = D-tryptophan
MOD_RES                 8
                        note = 3-(2-naphthyl)alanine
SEQUENCE: 22
XCXWKTCX                                                                        8

SEQ ID NO: 23           moltype = AA  length = 8
FEATURE                 Location/Qualifiers
source                  1..8
                        mol_type = protein
                        organism = synthetic construct
MOD_RES                 1
                        note = 4-Cl-phenylalanine
SITE                    2
                        note = D-cysteine
MOD_RES                 3
                        note = 4-amino-Phe(CONH-OH)
SITE                    4
                        note = D-tryptophan
MOD_RES                 8
                        note = 3-(2-naphthyl)alanine
SEQUENCE: 23
XCXWKTCX                                                                        8

SEQ ID NO: 24           moltype = AA  length = 8
FEATURE                 Location/Qualifiers
source                  1..8
                        mol_type = protein
                        organism = synthetic construct
MOD_RES                 1
                        note = 4-Cl-phenylalanine
SITE                    2
                        note = D-cysteine
MOD_RES                 3
                        note = 4-amino-Phe(carbamoyl)
MOD_RES                 3
                        note = 5F-D-Tryptophan
MOD_RES                 8
                        note = 3-(2-naphthyl)alanine
SEQUENCE: 24
XCXWKTCX                                                                        8

SEQ ID NO: 25           moltype = AA  length = 8
FEATURE                 Location/Qualifiers
source                  1..8
                        mol_type = protein
                        organism = synthetic construct
```

```
MOD_RES              1
                     note = 4-Cl-phenylalanine
SITE                 2
                     note = D-cysteine
MOD_RES              3
                     note = 4-amino-Phe(carbamoyl)
MOD_RES              4
                     note = 5F-Tryptophan
MOD_RES              8
                     note = 3-(2-naphthyl)alanine
SEQUENCE: 25
XCXWKTCX                                                                8

SEQ ID NO: 26        moltype = AA  length = 8
FEATURE              Location/Qualifiers
source               1..8
                     mol_type = protein
                     organism = synthetic construct
MOD_RES              1
                     note = 4-Cl-phenylalanine
SITE                 2
                     note = D-cysteine
MOD_RES              4
                     note = D-4-amino-Phe(carbamoyl)
MOD_RES              8
                     note = 3-(2-naphthyl)alanine
SEQUENCE: 26
XCYXKTCX                                                                8

SEQ ID NO: 27        moltype = AA  length = 8
FEATURE              Location/Qualifiers
source               1..8
                     mol_type = protein
                     organism = synthetic construct
MOD_RES              1
                     note = 4-Cl-phenylalanine
SITE                 2
                     note = D-cysteine
MOD_RES              3
                     note = 4-amino-L-hydroorotyl-phenylalanine
MOD_RES              4
                     note = D-4-amino-Phe(carbamoyl)
MOD_RES              8
                     note = 3-(2-naphthyl)alanine
SEQUENCE: 27
XCXXKTCX                                                                8
```

The invention claimed is:

1. A radiopeptide comprising
   (a) a radionuclide, wherein the radionuclide is terbium-161,
   (b) a chelator of terbium-161, and
   (c) LM3 ([p-Cl-Phe-cyclo [D-Cys-Tyr-D-Aph(Cbm)-Lys-Thr-Cys]D-Tyr-NH$_2$]) (SEQ ID NO:2), which is a somatostatin receptor (SSTR) antagonist;
   wherein the somatostatin receptor (SSTR) antagonist is covalently coupled to (b).

2. The radiopeptide of claim 1, wherein the chelator is a cyclic chelator.

3. The radiopeptide of claim 1, wherein the chelator is a tetradentate chelator containing four nitrogen atoms.

4. The radiopeptide of claim 3, wherein the chelator is a 12-membered tetraaza ring system comprising at least one substituent containing at least one carboxy function.

5. The radiopeptide of claim 1, wherein the chelator is DOTA or a DOTA derivative, wherein the DOTA derivative is selected from the group consisting of:

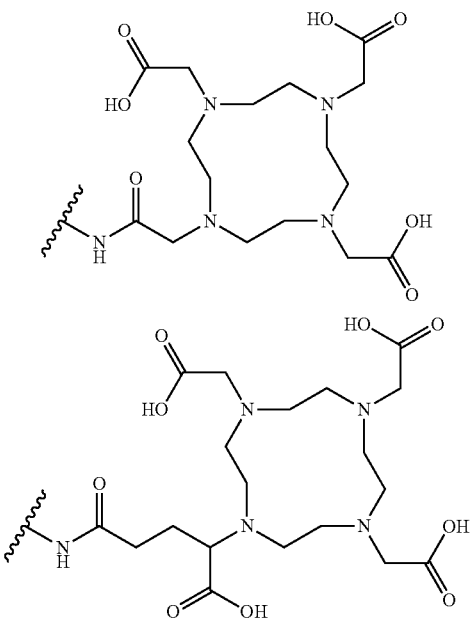

-continued

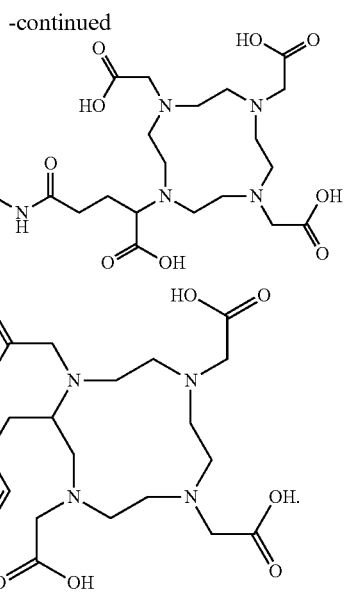

6. The radiopeptide of claim 1, wherein the somatostatin receptor antagonist is covalently coupled to the chelator via an amide linkage.

7. The radiopeptide of claim 1, wherein terbium-161 is produced by neutron irradiation of gadolinium-160.

8. The radiopeptide of claim 1, wherein terbium-161 is a non-carrier-added terbium-161 (n.c.a. terbium-161).

9. The radiopeptide of claim 1, wherein the radiopeptide has the structure of the following formula:

12. The pharmaceutical composition of claim 10, wherein the composition contains at least one of the group consisting of: gentisic acid, ethanol, acetate, NaCl and ascorbate/ascorbic acid.

13. The pharmaceutical composition of claim 12, wherein the composition contains ascorbate.

14. The pharmaceutical composition of claim 13, wherein the composition contains 0.5 mM to 0.5 M ascorbate.

15. The pharmaceutical composition of claim 10, wherein the composition has a pH value in the range from pH 3.5 to pH 6.

16. A method of treating a tumor disease in a subject in need thereof, wherein the tumor disease comprises a tumor characterized by expression of somatostatin receptor (SSTR), comprising:
administering a therapeutically effective amount of the radiopeptide of claim 1 to the subject, thereby treating the tumor disease.

17. The method of claim 16, wherein the subject suffers from a neuroendocrine neoplasm and/or metastases thereof,
wherein the neuroendocrine neoplasm is in the gastropancreatic, bronchopulmonary tract, thyroid, thymus, or pituitary gland.

18. The method of claim 16, wherein the subject suffers from a neuroendocrine neoplasm and/or metastases thereof, wherein the neuroendocrine neoplasm is selected from the group consisting of: gastroenteropancreatic neuroendocrine neoplasm, neuroendocrine tumor of the lung, neuroendocrine carcinoma of the lung, thymic neuroendocrine tumor, paraganglioma, pheochromocytoma, meningioma, medullary thyroid cancer, thyroid cancer, breast cancer, renal cell carcinoma, prostate cancer, non-Hodgkin lymphoma, and a pancreatic tumor.

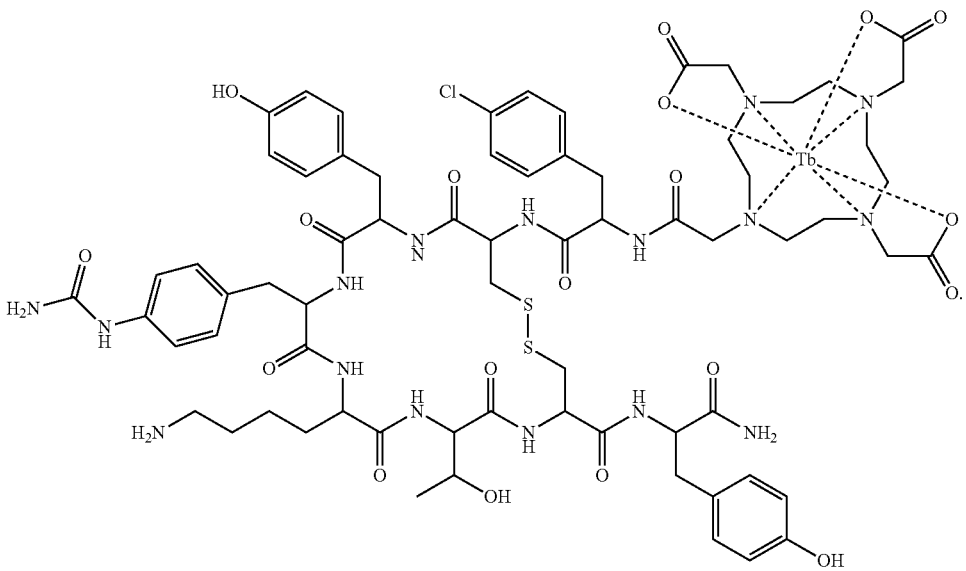

10. A pharmaceutical composition, comprising the radiopeptide of claim 1 and at least one pharmaceutically acceptable excipient.

11. The pharmaceutical composition of claim 10, wherein the composition comprises 0.001 to 1 mg/ml of the radiopeptide.

19. The method of claim 17, wherein the neuroendocrine neoplasm is stable or refractory to a therapy by Lutetium ($^{177}$Lu)-Oxodotreotid or other radiolabelled somatostatin analogues.

20. The method of claim 16, wherein the radiopeptide is administered systemically.

* * * * *